US012757632B2

(12) United States Patent
Kim et al.

(10) Patent No.: US 12,757,632 B2
(45) Date of Patent: Oct. 6, 2026

(54) ORGANIC LIGHT-EMITTING DEVICE AND APPARATUS INCLUDING THE SAME

(71) Applicant: Samsung Display Co., Ltd., Yongin-si (KR)

(72) Inventors: Minkyung Kim, Yongin-si (KR); Heejoo Ko, Yongin-si (KR); Jonghyeon Lee, Yongin-si (KR); Hangeul Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 776 days.

(21) Appl. No.: 16/987,332

(22) Filed: Aug. 6, 2020

(65) Prior Publication Data

US 2021/0184135 A1 Jun. 17, 2021

(30) Foreign Application Priority Data

Dec. 12, 2019 (KR) ........................ 10-2019-0165995

(51) Int. Cl.
*H10K 85/60* (2023.01)
*C07D 409/14* (2006.01)
(Continued)

(52) U.S. Cl.
CPC ....... *H10K 85/6572* (2023.02); *C07D 409/14* (2013.01); *C07D 495/04* (2013.01);
(Continued)

(58) Field of Classification Search
CPC ............. H10K 85/6572; H10K 59/123; H10K 85/342; H10K 85/346; H10K 85/657;
(Continued)

(56) References Cited

U.S. PATENT DOCUMENTS 6,312,836 B1 11/2001 Bulovic et al.
7,652,287 B2 * 1/2010 Jeong ................. H01L 29/7869 257/E29.151
(Continued)

FOREIGN PATENT DOCUMENTS

JP 2004273190 A * 9/2004
JP 2012-113976 6/2012
(Continued)

OTHER PUBLICATIONS

Auxiliary, Vocabulary.com, 2023 (Year: 2023).*
(Continued)

*Primary Examiner* — Braelyn R Watson
(74) *Attorney, Agent, or Firm* — Womble Bond Dickinson (US) LLP

(57) ABSTRACT

An organic light-emitting device includes: a first electrode; a second electrode; and an organic layer between the first electrode and the second electrode, the organic layer having a first emission layer, a second emission layer between the first emission layer and the second electrode, and at least one auxiliary layer, having a first host or a second host, the first emission layer may include a first host, a second host, and a first dopant; and the second emission layer may include a first host, a second host, and a second dopant; wherein the second host may include at least one of an electron transport host and a bipolar host; the first dopant and the second dopant, each may include, independently from one another, at least one of a phosphorescent organometallic compound and a thermally activated delayed fluorescence ("TADF") compound satisfying Equation 1 as defined herein.

15 Claims, 2 Drawing Sheets

(51) Int. Cl.

| | |
|---|---|
| ***C07D 495/04*** | (2006.01) |
| ***C07F 15/00*** | (2006.01) |
| ***C09K 11/06*** | (2006.01) |
| ***H10K 50/11*** | (2023.01) |
| ***H10K 59/123*** | (2023.01) |
| ***H10K 85/30*** | (2023.01) |
| ***H10K 101/00*** | (2023.01) |
| ***H10K 101/10*** | (2023.01) |
| ***H10K 101/30*** | (2023.01) |
| *H10K 50/135* | (2023.01) |

(52) U.S. Cl.

CPC .......... *C07F 15/0086* (2013.01); *C09K 11/06* (2013.01); *H10K 59/123* (2023.02); *H10K 85/342* (2023.02); *H10K 85/346* (2023.02); *H10K 85/657* (2023.02); *H10K 85/6576* (2023.02); *C09K 2211/1018* (2013.01); *C09K 2211/1048* (2013.01); *C09K 2211/185* (2013.01); *H10K 50/11* (2023.02); *H10K 50/135* (2023.02); *H10K 2101/10* (2023.02); *H10K 2101/30* (2023.02); *H10K 2101/90* (2023.02)

(58) Field of Classification Search

CPC .. H10K 85/6576; H10K 50/11; H10K 50/135; H10K 2101/10; H10K 2101/30; H10K 2101/90; H10K 50/13; H10K 50/131; H10K 50/156; H10K 50/166; H10K 2101/20; H10K 85/40; H10K 85/654; H10K 85/6574; H10K 50/80; H10K 85/322; H10K 85/633; H10K 50/12; C07D 409/14; C07D 495/04; C07F 15/0086; C09K 11/06; C09K 2211/1018; C09K 2211/1048; C09K 2211/185; H01L 51/504; H01L 2251/5384

See application file for complete search history.

(56) References Cited

U.S. PATENT DOCUMENTS

| | | | | |
|---|---|---|---|---|
| 7,851,579 | B2 | 12/2010 | Ye et al. | |
| 8,585,659 | B2 | 11/2013 | Shay | |
| 8,653,548 | B2 | 2/2014 | Krummacher et al. | |
| 8,928,976 | B2 | 1/2015 | Kang et al. | |
| 8,957,236 | B2 | 2/2015 | Zhang et al. | |
| 8,993,129 | B2 | 3/2015 | Endo et al. | |
| 9,024,026 | B2 | 5/2015 | Yersin et al. | |
| 9,059,460 | B2 | 6/2015 | Hattori et al. | |
| 9,093,650 | B2 | 7/2015 | Kim et al. | |
| 9,099,658 | B2 | 8/2015 | Kawamura et al. | |
| 9,101,447 | B2 | 8/2015 | Sramek | |
| 9,153,788 | B2 | 10/2015 | Adachi et al. | |
| 9,266,906 | B2 | 2/2016 | Baumann et al. | |
| 9,312,496 | B2 | 4/2016 | Sawada et al. | |
| 9,357,217 | B2 | 5/2016 | Kirchhoffer et al. | |
| 9,431,625 | B2 | 8/2016 | Moon et al. | |
| 9,476,782 | B2 | 10/2016 | Suzuki et al. | |
| 9,481,980 | B2 | 11/2016 | Bang | |
| 9,496,516 | B2 | 11/2016 | Sakuma et al. | |
| 9,502,668 | B2 | 11/2016 | Adachi et al. | |
| 9,537,117 | B2 | 1/2017 | Yersin et al. | |
| 9,559,324 | B2 | 1/2017 | Seo et al. | |
| 9,564,598 | B2 | 2/2017 | Ito et al. | |
| 9,604,928 | B2 | 3/2017 | Shitagaki et al. | |
| 9,614,166 | B2 | 4/2017 | Kai et al. | |
| 9,615,461 | B2 | 4/2017 | Nakamura et al. | |
| 9,634,262 | B2 | 4/2017 | Adachi et al. | |
| 9,647,218 | B2 | 5/2017 | Kwong et al. | |
| 9,660,199 | B2 | 5/2017 | Shizu et al. | |
| 9,685,615 | B2 | 6/2017 | Numata et al. | |
| 9,793,492 | B2 | 10/2017 | Sagara et al. | |
| 9,957,260 | B2 | 5/2018 | Sakai et al. | |
| 9,966,541 | B2 | 5/2018 | Yamamoto et al. | |
| 10,062,867 | B2 | 8/2018 | Seo et al. | |
| 10,290,826 | B2 | 5/2019 | Kim et al. | |
| 10,326,111 | B2 | 6/2019 | Yoo et al. | |
| 10,361,388 | B2 | 7/2019 | Mitsumori et al. | |
| 10,418,573 | B2 | 9/2019 | Kim et al. | |
| 10,454,038 | B2 | 10/2019 | Nakagawa et al. | |
| 10,461,261 | B2 | 10/2019 | Li et al. | |
| 10,510,806 | B2 | 12/2019 | Yamaoka et al. | |
| 10,573,822 | B2 | 2/2020 | Kim et al. | |
| 10,651,394 | B2 | 5/2020 | Danz | |
| 2005/0260440 | A1 | 11/2005 | Seo et al. | |
| 2009/0017331 | A1* | 1/2009 | Iwakuma ........... | H10K 85/6574 548/440 |
| 2011/0304262 | A1 | 12/2011 | Kwong | |
| 2012/0217869 | A1 | 8/2012 | Adachi et al. | |
| 2012/0241725 | A1* | 9/2012 | Sawabe .................. | H10K 50/11 257/40 |
| 2012/0248421 | A1* | 10/2012 | Yamazaki .......... | H10K 85/6576 257/E51.024 |
| 2012/0256173 | A1* | 10/2012 | Kitamura .............. | C09B 57/007 257/E51.026 |
| 2013/0062599 | A1 | 3/2013 | Holmes et al. | |
| 2014/0027734 | A1 | 1/2014 | Kwong | |
| 2014/0138627 | A1 | 5/2014 | Kwong et al. | |
| 2014/0145149 | A1 | 5/2014 | Lin et al. | |
| 2014/0145151 | A1 | 5/2014 | Xia et al. | |
| 2014/0158992 | A1 | 6/2014 | Xia et al. | |
| 2014/0179585 | A1 | 6/2014 | Souter et al. | |
| 2014/0291647 | A1 | 10/2014 | Suzuki et al. | |
| 2014/0332758 | A1 | 11/2014 | Kwong et al. | |
| 2015/0021555 | A1 | 1/2015 | Kwong et al. | |
| 2015/0132831 | A1 | 5/2015 | Olinski et al. | |
| 2015/0141642 | A1 | 5/2015 | Adachi et al. | |
| 2015/0170847 | A1 | 6/2015 | Wrede | |
| 2015/0218191 | A1 | 8/2015 | Sannomiya et al. | |
| 2015/0318510 | A1 | 11/2015 | Ito et al. | |
| 2015/0340618 | A1* | 11/2015 | Lee ...................... | C07D 213/06 544/294 |
| 2016/0072082 | A1* | 3/2016 | Brooks ................ | C07D 471/16 546/4 |
| 2016/0164035 | A1* | 6/2016 | Seo ........................ | C09K 11/06 257/40 |
| 2016/0197286 | A1 | 7/2016 | Kawamura et al. | |
| 2016/0232265 | A1 | 8/2016 | Thompson et al. | |
| 2016/0285015 | A1 | 9/2016 | Li et al. | |
| 2016/0372683 | A1 | 12/2016 | Tanimoto et al. | |
| 2017/0018600 | A1 | 1/2017 | Ito et al. | |
| 2017/0047533 | A1* | 2/2017 | Li ........................ | H10K 85/346 |
| 2017/0117488 | A1* | 4/2017 | Ahn ..................... | H10K 85/654 |
| 2017/0162817 | A1 | 6/2017 | Ogiwara et al. | |
| 2017/0179419 | A1* | 6/2017 | Lee .......................... | B60Q 1/24 |
| 2017/0200899 | A1 | 7/2017 | Kim et al. | |
| 2017/0271597 | A1 | 9/2017 | Miyata et al. | |
| 2017/0352829 | A1 | 12/2017 | Seo et al. | |
| 2017/0373255 | A1* | 12/2017 | Lee ...................... | C07D 251/24 |
| 2017/0373260 | A1* | 12/2017 | Li .......................... | C09K 11/06 |
| 2018/0166646 | A1* | 6/2018 | Tang .................... | H10K 50/181 |
| 2018/0182980 | A1 | 6/2018 | Lennartz et al. | |
| 2018/0301511 | A1* | 10/2018 | Liao ....................... | H10K 50/17 |
| 2018/0351124 | A1 | 12/2018 | Yoneda et al. | |
| 2018/0375035 | A1 | 12/2018 | Ji et al. | |
| 2019/0036055 | A1 | 1/2019 | Lin et al. | |
| 2019/0058144 | A1 | 2/2019 | Lee et al. | |
| 2019/0203114 | A1 | 7/2019 | Ihn et al. | |
| 2019/0372055 | A1 | 12/2019 | Wu et al. | |
| 2020/0203652 | A1 | 6/2020 | Duan et al. | |
| 2021/0066617 | A1* | 3/2021 | Shin ..................... | C07D 209/88 |

FOREIGN PATENT DOCUMENTS

| | | |
|---|---|---|
| JP | 2013-008806 | 1/2013 |
| JP | 2014-043541 | 3/2014 |
| JP | 2014-521856 | 8/2014 |
| JP | 5594750 | 9/2014 |
| JP | 5679496 | 3/2015 |
| JP | 5789439 | 10/2015 |

(56) References Cited

FOREIGN PATENT DOCUMENTS

| | | | | | |
|---|---|---|---|---|---|
| JP | 2016-036025 | | | 3/2016 | |
| JP | 5875011 | | | 3/2016 | |
| JP | 2016-210728 | | | 12/2016 | |
| JP | 6169078 | | | 7/2017 | |
| JP | 6305391 | | | 4/2018 | |
| JP | 2018-092932 | | | 6/2018 | |
| JP | 2018-207030 | | | 12/2018 | |
| JP | 6439791 | | | 12/2018 | |
| JP | 6542122 | | | 7/2019 | |
| JP | 6756614 | | | 9/2020 | |
| KR | 10-0669776 | | | 1/2007 | |
| KR | 10-2010-0037607 | | | 4/2010 | |
| KR | 10-2012-0112517 | | | 10/2012 | |
| KR | 10-2014-0010359 | | | 1/2014 | |
| KR | 10-2014-0044904 | | | 4/2014 | |
| KR | 10-2014-0068027 | | | 6/2014 | |
| KR | 10-2015-0010862 | | | 1/2015 | |
| KR | 10-2015-0056046 | | | 5/2015 | |
| KR | 10-2015-0126527 | | | 11/2015 | |
| KR | 20160039492 | A | * | 4/2016 | ........... C07D 209/82 |
| KR | 10-2016-0101519 | | | 8/2016 | |
| KR | 10-1680934 | | | 11/2016 | |
| KR | 10-2017-0026075 | | | 3/2017 | |
| KR | 10-2017-0031362 | | | 3/2017 | |
| KR | 10-2017-0059980 | | | 5/2017 | |
| KR | 10-1742359 | | | 5/2017 | |
| KR | 10-1844434 | | | 4/2018 | |
| KR | 20180056938 | A | * | 5/2018 | ........... C07D 251/24 |
| KR | 2018072251 | A | * | 6/2018 | ......... H01L 51/0004 |
| KR | 10-1908385 | | | 10/2018 | |
| KR | 10-2019-0011754 | | | 2/2019 | |
| KR | 10-2019-0012117 | | | 2/2019 | |
| KR | 10-2019-0012679 | | | 2/2019 | |
| KR | 10-2000980 | | | 7/2019 | |
| WO | 2012050003 | | | 4/2012 | |
| WO | 2012-073888 | | | 6/2012 | |
| WO | 2013-161437 | | | 10/2013 | |
| WO | 2013-180241 | | | 12/2013 | |
| WO | 2014-050904 | | | 4/2014 | |
| WO | WO-2014050417 | A1 | * | 4/2014 | ........... C07D 209/86 |
| WO | 2014103724 | | | 7/2014 | |
| WO | 2014-126200 | | | 8/2014 | |
| WO | 2014-157268 | | | 10/2014 | |
| WO | 2015-002213 | | | 1/2015 | |
| WO | 2015-008580 | | | 1/2015 | |
| WO | 2015-022835 | | | 2/2015 | |
| WO | 2015-118035 | | | 8/2015 | |
| WO | 2015-158692 | | | 10/2015 | |
| WO | 2016-017514 | | | 2/2016 | |
| WO | 2016-017684 | | | 2/2016 | |
| WO | 2016-017741 | | | 2/2016 | |
| WO | 2016-091887 | | | 6/2016 | |
| WO | 2016-096851 | | | 6/2016 | |

OTHER PUBLICATIONS

English translation of KR20180056938A obtained from Espacenet (Year: 2018).*

English translation of KR20160039492A obtained from Espacenet (Year: 2016).*

English translation of WO 2014050417 A1 obtained from Global Dossier (Year: 2014).*

Hang, Xiao-Chun, et al. "Highly efficient blue-emitting cyclometalated platinum (II) complexes by judicious molecular design." Angewandte Chemie 125.26 (2013) (Year: 2013).*

English translation of JP 2004273190 obtained from JPlatPat (Year: 2004).*

Gong, Shaolong, et al. "Simple CBP isomers with high triplet energies for highly efficient blue electrophosphorescence." Journal of Materials Chemistry 22.7 (2012): 2894-2899. (Year: 2012).*

English translation of KR 2018072251 A obtained from Espacenet (Year: 2018).*

Cai, Minghan, et al. "Investigation on two triphenylene based electron transport materials." Science China Chemistry 62.6 (2019): 775-783. (Year: 2019).*

Non-Final Office Action dated Jan. 12, 2023, issued in U.S. Appl. No. 17/009,286.

U.S. Appl. No. 17/035,448, filed Sep. 28, 2020.

U.S. Appl. No. 17/030,365, filed Sep. 23, 2020.

U.S. Appl. No. 17/009,286, filed Sep. 1, 2020.

Jeong-Hwan Lee et al., "An Exciplex Forming Host for Highly Efficient Blue Organic Light Emitting Diodes with Low Driving Voltage," Advanced Functional Materials, 2014, vol. 25, pp. 1-6.

"EQE Optimization for a TOP-Emitting OLED", Jul. 28, 2020, available at www.fluxim.com/high-eqe-toled, 7 pages.

L. Penninck et al., "Determining emissive dipole orientation in organic light emitting devices by decay time measurement," Organic Electronics 2012, 13, pp. 3079-3084.

www.spiedigitallibrary.org, no later than Aug. 4, 2020, 1 page.

A. Graf et al., "Correlating the transition dipole moment orientation of phosphorescent emitter molecules in OLEDs to basic material properties," J. Mater. Chem. C, 2012, 2(48), pp. 10298-10304.

Alessia Senes et al., "Increasing the horizontal orientation of transition dipole moments in solution processed small molecular emitters," J. Mater. Chem. C, 2017, 5(26), 6555-6562.

Malika Ibrahim-Ouali et al., "Recent Advances on Metal-Based Near-Infrared and Infrared Emitting OLEDs, Molecules," 2019, 24(7), 1412, 39 pages.

U.S. Appl. No. 17/098,455, filed Nov. 16, 2020.

U.S. Appl. No. 17/035,448.

U.S. Appl. No. 17/030,365.

U.S. Appl. No. 17/009,286.

U.S. Appl. No. 17/098,455.

* cited by examiner

ORGANIC LIGHT-EMITTING DEVICE AND APPARATUS INCLUDING THE SAME

CROSS-REFERENCE TO RELATED APPLICATIONS

This application claims priority from and the benefit of Korean Patent Application No. 10-2019-0165995, filed on Dec. 12, 2019, which is hereby incorporated by reference for all purposes as if fully set forth herein.

BACKGROUND

Field

Exemplary implementations of the invention relate generally to organic light-emitting device and, more specifically, to an apparatus including the same.

Discussion of the Background

Organic light-emitting devices are self-emission devices that produce full-color images, and also have wide viewing angles, high contrast ratios, short response times, as well as excellent characteristics in terms of brightness, driving voltage, and response speed.

An example of the organic light-emitting devices may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, recombine in the emission layer to produce excitons. These excitons transit from an excited state to a ground state, thereby generating light.

The above information disclosed in this Background section is only for understanding of the background of the inventive concepts, and, therefore, it may contain information that does not constitute prior art.

SUMMARY

According to one aspect of the invention, an organic light-emitting device includes: a first electrode; a second electrode; and an organic layer disposed between the first electrode and the second electrode, the organic layer having a first emission layer, a second emission layer disposed between the first emission layer and the second electrode, and at least one auxiliary layer, wherein the at least one auxiliary layer includes at least one of a first auxiliary layer having a first host or a second host disposed between the first electrode and the first emission layer and directly contacting the first emission layer, a second auxiliary layer having a first host or a second host disposed between the second emission layer and the second electrode and directly contacting the second emission layer, and a third auxiliary layer having a first host or a second host disposed between the first emission layer and the second emission layer; the first emission layer includes a first host, a second host, and a first dopant; and the second emission layer includes a first host, a second host, and a second dopant; wherein the first host is a hole transport host, and the second host includes at least one of an electron transport host and a bipolar host; the first dopant and the second dopant, each includes, independently from one another, at least one of a phosphorescent organometallic compound and a thermally activated delayed fluorescence ("TADF") compound satisfying Equation 1 below, and the first dopant and the second dopant are different from each other:

$$\Delta E_{ST} = S1 - T1 \leq 0.3\ \text{eV}$$ <Equation 1> wherein, in Equation 1, S1 is a lowest excitation singlet energy level (eV) of the TADF compound, and T1 is a lowest excitation triplet energy level (eV) of the TADF compound.

The first host may be a compound that may include a π electron-deficient nitrogen-free cyclic group and may not include a π electron-deficient nitrogen-containing cyclic group.

The first host may be a carbazole-containing compound that may include a π electron-deficient nitrogen-free cyclic group and may not include a π electron-deficient nitrogen-containing cyclic group.

The first host may include at least one of a compound of Formula 1-1 and a compound of Formula 1-2:

<Formula 1-1>

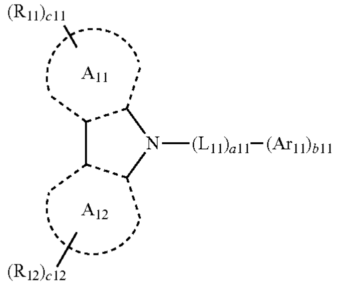

<Formula 1-2> wherein, in Formulae 1-1 and 1-2, the variables are defined herein.

The electron transport host may include at least one electron withdrawing group, and the bipolar host may include at least one electron withdrawing group and at least one electron donating group.

The electron withdrawing group may be: —F, —$CFH_2$, —$CF_2H$, —$CF_3$, —CN, or —$NO_2$; a $C_1$-$C_{60}$ alkyl group substituted with at least one of —F, —$CFH_2$, —$CF_2H$, —$CF_3$, —CN, and —$NO_2$; or a substituted or unsubstituted π electron-deficient nitrogen-containing cyclic group; and the electron donating group may be a substituted or unsubstituted carbazole group, a substituted or unsubstituted dibenzofuran group, a substituted or unsubstituted dibenzothiophene group, a substituted or unsubstituted indolocarbazole group, a substituted or unsubstituted benzofurocarbazole group, a substituted or unsubstituted benzothienocarbazole group, a substituted or unsubstituted acridine group, a substituted or unsubstituted phenoxazine group, a substituted or unsubstituted phenothiazine group, a substituted or unsubstituted phenazine group, or —$N(Q_1)(Q_2)$; wherein $Q_1$ and $Q_2$ may each, independently from one another, be hydrogen, deuterium, a $C_1$-$C_{60}$ alkyl group, a $C_2$-$C_{60}$ alkenyl group, a $C_2$-$C_{60}$ alkynyl group, a $C_1$-$C_{60}$ alkoxy group, a π electron-deficient nitrogen-free cyclic group, a biphenyl group, or a terphenyl group.

The second host may include at least one of compound of Formulae 2-1, 2-2, and 2-3:

<Formula 2-1>

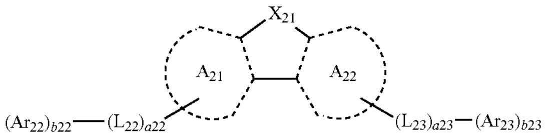

<Formula 2-2>

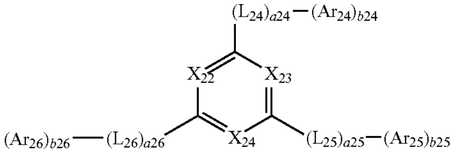

<Formula 2-3>

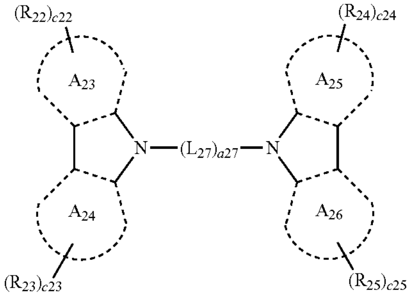

wherein, in Formulae 2-1 to 2-3, the variables are defined herein.

The phosphorescent organometallic compound may be a compound of Formula 3:

$M_{31}(L_{31})_{n31}(L_{32})_{n32}$ <Formula 3> wherein, in Formula 3, the variables are defined herein.

The TADF compound may include at least one of compounds of Formulae 4-1 to 4-8:

<Formula 4-1>

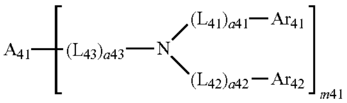

<Formula 4-2>

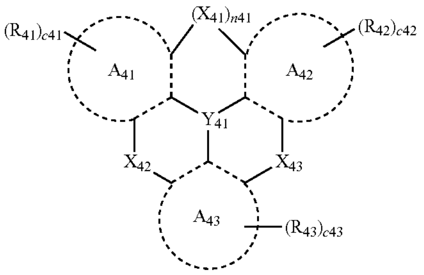

-continued

<Formula 4-3>

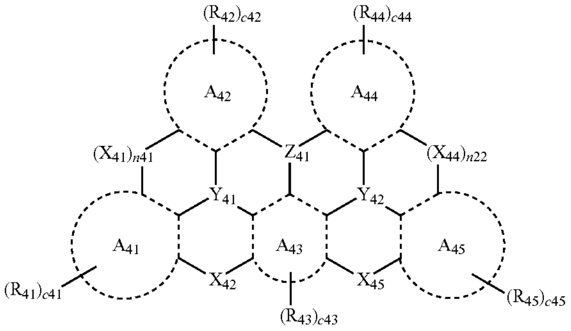

<Formula 4-4>

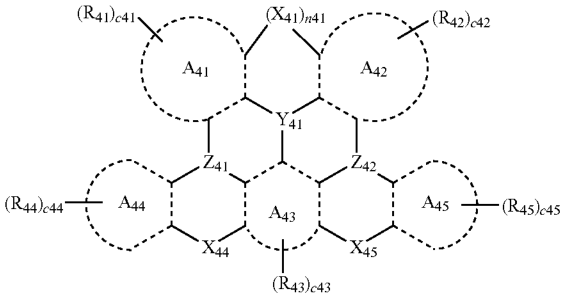

<Formula 4-5>

$(EDG)_{b41}—[(L_{44})_{a44}—(EWG)_{t42}]_{s41}$

<Formula 4-6>

$(EWG)_{t42}—[(L_{44})_{a44}—(EDG)_{b41}]_{s42}$

<Formula 4-7>

$(EDG)_{b411}—(L_{44})_{a44}—(EWG)_{t42}—(L_{45})_{a45}—(EDG)_{b412}$

<Formula 4-8>

$(EWG)_{t421}—(L_{44})_{a44}—(EDG)_{b41}—(L_{45})_{a45}—(EWG)_{t422}$ wherein in the formulas, the variables are defined herein.

The first host may be a compound of Compounds 1-1 to 1-22; the second host may be a compound of Compounds 2-1 to 2-30: the phosphorescent organometallic complex may be a compound of Compounds 3-11 to 3-18; and the TADF compound may be one of Compounds 4-1 to 4-13, as disclosed herein.

The at least one auxiliary layer may include a first auxiliary layer disposed is between the first electrode and the first emission layer and directly contacting the first emission layer; the first auxiliary layer may include a first host; and a first host included in the first auxiliary layer and a first host included in the first emission layer may be identical to or different from each other.

The first auxiliary layer may consist of the first host.

The at least one auxiliary layer may include a second auxiliary layer disposed between the second emission layer and the second electrode and directly contacting the second emission layer; the second auxiliary layer may include a second host; and a second host included in the second auxiliary layer and a second host included in the second emission layer may be identical to or different from each other.

The second auxiliary layer may consist of the second host.

The at least one auxiliary layer may include a third auxiliary layer disposed between the first emission layer and the second emission layer; the third auxiliary layer may include a first host or a second host; when the third auxiliary layer may include a first host, a first host included in the third auxiliary layer and a first host included in the first emission layer may be identical to or different from each other, and a first host included in the third auxiliary layer and a first host included in the second emission layer may be identical to or different from each other; and when the third auxiliary layer may include a second host, a second host included in the third auxiliary layer and a second host included in the first emission layer may be identical to or different from each other, and a second host included in the third auxiliary layer and a second host included in the second emission layer may be identical to or different from each other.

The first dopant and the second dopant may each, independently from one another, be a phosphorescent organometallic compound.

The first dopant may have a first maximum emission wavelength and the second dopant may have a second maximum emission wavelength different from the first maximum emission wavelength.

The first emission layer may satisfy Equations 2 and 3:

$$|HOMO(D1)-HOMO(EML1(H1))| \leq \text{about } 0.3 \text{ eV} \quad \text{<Equation 2>}$$

$$|HOMO(D1)-HOMO(EML1(H2))| \leq \text{about } 0.3 \text{ eV} \quad \text{<Equation 3>}$$

wherein, in Equations 2 and 3,

HOMO(D1) is a highest occupied molecular orbital (HOMO) energy level (eV) of the first dopant, HOMO (EML1(H1)) is a HOMO energy level (eV) of a first host included in the first emission layer, and HOMO(EML1(H2)) is a HOMO energy level (eV) of a second host included in the first emission layer.

The second emission layer may satisfy Equations 4 and 5:

$$|LUMO(D2)-LUMO(EML2(H1))| \leq \text{about } 0.3 \text{ eV} \quad \text{<Equation 4>}$$

$$|LUMO(D2)-LUMO(EML2(H2))| \leq \text{about } 0.3 \text{ eV} \quad \text{<Equation 5>}$$

wherein, in Equations 4 and 5,

LUMO(D2) is a lowest unoccupied molecular orbital (LUMO) energy level (eV) of the second dopant, LUMO(EML2(H1)) is a LUMO energy level (eV) of a first host included in the second emission layer, and LUMO(EML2(H2)) is a LUMO energy level (eV) of a second host included in the second emission layer.

An apparatus may include a thin-film transistor having a source electrode, a drain electrode, and an activation layer; and an organic light-emitting device as described above wherein the first electrode of the organic light-emitting device may be electrically connected to one of the source electrode and the drain electrode of the thin-film transistor.

Additional features of the inventive concepts will be set forth in the description which follows, and in part will be apparent from the description, or may be learned by practice of the inventive concepts.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
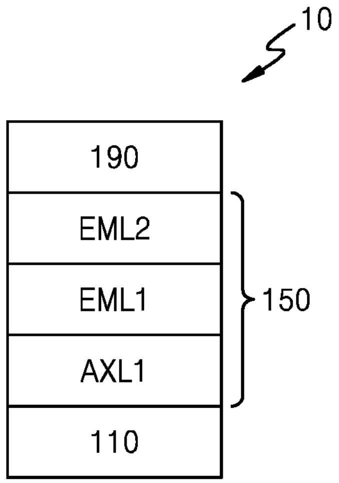
FIG. 1 is a schematic cross-sectional diagram of an exemplary embodiment of an organic light-emitting device constructed according to principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

The term "an organic layer" as used herein refers to a single layer and/or a plurality of layers disposed between the first electrode and the second electrode of an organic light-emitting device. A material included in the "organic layer" is not limited to an organic material.

The expression "(an organic layer) includes a compound of or represented by Formula 1" as used herein may include a case in which "(an organic layer) includes one compound of Formula 1 or two or more different compounds of Formula 1".

According to some exemplary embodiments of the invention, an organic light-emitting device includes: a first electrode; a second electrode; and an organic layer between the first electrode and the second electrode,

- the organic layer includes a first emission layer, a second emission layer disposed between the first emission layer and the second electrode, and at least one auxiliary layer,
- the at least one auxiliary layer includes at least one of a first auxiliary layer disposed between the first electrode and the first emission layer and directly contacting the first emission layer, a second auxiliary layer disposed between the second emission layer and the second electrode and directly contacting the second emission layer, and a third auxiliary layer disposed between the first emission layer and the second emission layer,
- the first emission layer includes a first host, a second host, and a first dopant,
- the second emission layer includes a first host, a second host, and a second dopant,
- the at least one auxiliary layer each independently includes a first host or a second host,
- the first host is a hole transport host,
- the second host includes at least one selected from an electron transport host and a bipolar host,
- the first dopant and the second dopant each independently include at least one of a phosphorescent organometallic compound and a thermally activated delayed fluorescence (TADF) compound satisfying Equation 1 below, and
- the first dopant and the second dopant are different from each other:

$$\Delta E_{ST}=S1-T1\leq 0.3\text{ eV} \quad \text{<Equation 1>}$$

In Equation 1, S1 is a lowest excitation singlet energy level (eV) of the TADF compound, and T1 is a lowest excitation triplet energy level (eV) of the TADF compound.

A first host included in the first emission layer and a first host included in the second emission layer may be identical to or different from each other, and a second host included in the first emission layer and a second host included in the second emission layer may be identical to or different from each other.

The organic light-emitting device may include at least one auxiliary layer selected from a first auxiliary layer adjacent to the first emission layer, a second auxiliary layer adjacent to the second emission layer, and a third emission layer between the first emission layer and the second emission layer. In addition, by including a first host or a second host in the at least one auxiliary layer, compared to an organic light-emitting device that does not include an auxiliary layer, the injection of holes and electrons into the emission layer may increase, thereby reducing accumulation of holes and electrons at an interface between a common layer and the emission layer. Accordingly, the problem that holes and/or electrons accumulated without participating in exciton formation deteriorate a material for a common layer and/or a material for an emission layer may be minimized. Thus, the organic light-emitting device may have improved lifespan.

FIG. 1 is a schematic cross-sectional diagram of an exemplary embodiment of an organic light-emitting device constructed according to principles of the invention.

FIG. 1 is a schematic view of an organic light-emitting device 10 according to an exemplary embodiment. The organic light-emitting device 10 includes a first electrode 110, an organic layer 150, and a second electrode 190. The organic layer 150 includes a first emission layer EML1, a second emission layer EML2 disposed between the first emission layer EML1 and the second electrode 190, and at least one auxiliary layer such as a first auxiliary layer AXL1 disposed between the first emission layer 110 and the first emission layer EML1 and directly contacting the first emission layer EML1.

Direct contact between the first auxiliary layer AXL1 and the first emission layer EML1 indicates that the no other layers are disposed between the first auxiliary layer AXL1 and the first emission layer EML1.

In some exemplary embodiments, the first auxiliary layer AXL1 may include a first host. A first host included in the first auxiliary layer AXL1 and a first host included in the first emission layer EML1 may be identical to or different from each other.

For example, the first host included in the first auxiliary layer AXL1 may be a hole transport host, and the first host included in the first auxiliary layer AXL1 and the first host included in the first emission layer EML1 may be identical to or different from each other. For example, the first auxiliary layer AXL1 and the first emission layer EML1 may include identical or different hole transport hosts.

The first auxiliary layer AXL1 does not include a dopant. Accordingly, In some exemplary embodiments, the first auxiliary layer AXL1 may consist of the first host, but the exemplary embodiments are not limited thereto.

Figure 2:
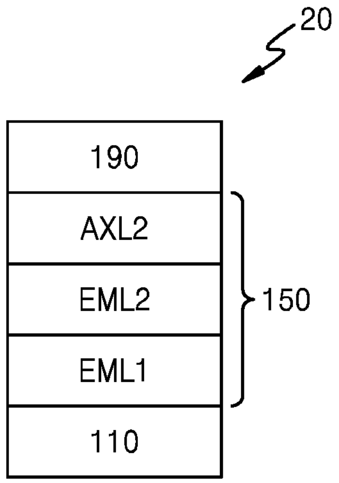
FIG. 2 is a schematic cross-sectional diagram of another exemplary embodiment of an organic light-emitting device constructed according to principles of the invention.

FIG. 2 is a schematic cross-sectional diagram of another exemplary embodiment of an organic light-emitting device constructed according to principles of the invention.

As illustrated in FIG. 2, an organic light-emitting device 20 according to another exemplary embodiment may include the at least one auxiliary layer such as a second auxiliary layer AXL2 disposed between the second emission layer EML2 and the second electrode 190 and directly contacting the second emission layer EML2.

In some exemplary embodiments, the second auxiliary layer AXL2 may include a second host. A second host included in the second auxiliary layer AXL2 and a second host included in the second emission layer EML2 may be identical to or different from each other. For example, the second host included in the second auxiliary layer AXL2 may include one selected from an electron transport host and a bipolar host, and the second host included in the second auxiliary layer AXL2 and the second host included in the second emission layer EML2 may be identical to or different from each other.

The second auxiliary layer AXL2 does not include a dopant. Accordingly, In some exemplary embodiments, the second auxiliary layer AXL2 may consist of the second host, but the exemplary embodiments are not limited thereto.

Figure 3:
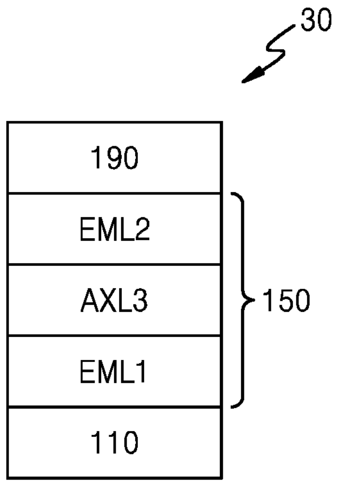
FIG. 3 is a schematic cross-sectional diagram of yet another exemplary embodiment of an organic light-emitting device constructed according to principles of the invention.

FIG. 3 is a schematic cross-sectional diagram of yet another exemplary embodiment of an organic light-emitting device constructed according to principles of the invention.

In one or more exemplary embodiments, as illustrated in FIG. 3, an organic light-emitting device 30 may include the at least one auxiliary layer such as a third auxiliary layer AXL3 disposed between the first emission layer EML1 and the second emission layer EML2.

In some exemplary embodiments, the third auxiliary layer AXL3 may include a first host or a second host. When the third auxiliary layer AXL3 includes a first host, a first host included in the third auxiliary layer AXL3 and a first host included in the first emission layer EML1 may be identical to or different from each other, and a first host included in the third auxiliary layer AXL3 and a first host included in the second emission layer EML2 may be identical to or different from each other. When the third auxiliary layer AXL3 includes a second host, a second host included in the third auxiliary layer AXL3 and a second host included in the first emission layer EML1 may be identical to or different from each other, and a second host included in the third auxiliary layer AXL3 and a second host included in the second emission layer EML2 may be identical to or different from each other.

In some exemplary embodiments, a first host included in the third auxiliary layer AXL3 may be a hole transport host, and a second host included in the third auxiliary layer AXL3 may be selected from an electron transport host and a bipolar host.

An organic light-emitting device according to some exemplary embodiments may include at least two of the first auxiliary layer AXL1, the second auxiliary layer AXL2, and the third auxiliary layer AXL3.

The hole transport host may be a compound including a hole transport group, and the electron transport host may be a compound including an electron transport group.

In an organic light-emitting device according to some exemplary embodiments, an emission layer includes a mixed host of a hole transport host and an electron transport host. Thus, a charge balance of an emission layer may be optimized to expand an emission zone in an emission, and thus emission efficiency and lifespan may be improved.

Although an organic light-emitting device may include double emission layers that are a first emission layer and a second emission layer and include at least one auxiliary layer adjacent to at least one of the double emission layers, when each of the emission layers does not include a mixed host of a first host (hole transport host) and a second host (an electron transport host or a bipolar host), the injection of holes or electrons into an emission layer may be delayed, and thus an emission zone may be formed at an interface between a common layer and an emission layer. Accordingly, since degradation of the light-emitting device may be promoted, characteristics of the device may be degraded.

In some exemplary embodiments, the first host may be a compound that includes a π electron-deficient nitrogen-free cyclic group and does not include a π electron-deficient nitrogen-containing cyclic group.

The "π electron-deficient nitrogen-containing cyclic group" as used herein indicates a $C_1$-$C_{60}$ heterocyclic group having at least one *—N=*' moiety as a ring-forming moiety. For example, the π electron-deficient nitrogen-containing cyclic group may be an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, and an azadibenzosilole group, and a fused cyclic group in which at least one of aforementioned groups and any cyclic group are condensed with each other.

The "π electron-deficient nitrogen-free cyclic group" may include a $C_5$-$C_{60}$ carbocyclic group and a π electron-deficient nitrogen-free $C_5$-$C_{60}$ heterocyclic group. The R electron-deficient nitrogen-free cyclic group may be, for example, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group, but the exemplary embodiments are not limited thereto.

In some exemplary embodiments, the first host may be a carbazole-containing compound that includes a π electron-deficient nitrogen-free cyclic group and does not include a π electron-deficient nitrogen-containing cyclic group.

In some exemplary embodiments, the first host may include at least one of a compound represented by Formula 1-1 and a compound represented by Formula 1-2:

<Formula 1-1>

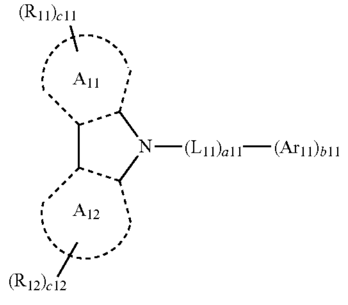

-continued

<Formula 1-2>

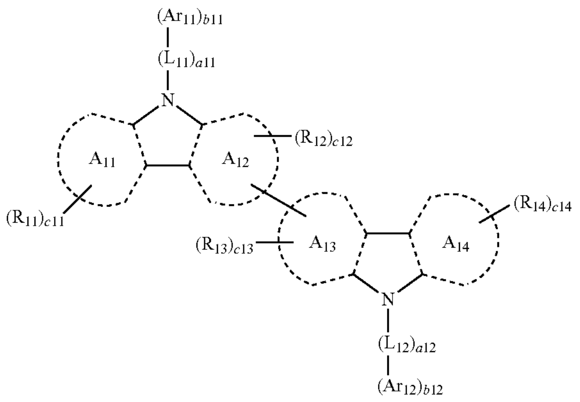

In Formulae 1-1 and 1-2, A11 to A14 may each independently be selected from benzene, naphthalene, anthracene, phenanthrene, fluoranthene, triphenylene, pyrene, chrysene, indene, fluorene, spiro-bifluorene, benzofluorene, dibenzofluorene, carbazole, benzocarbazole, dibenzocarbazole, dibenzofuran, and a dibenzothiophene.

For example, A11 to A14 may each independently be selected from benzene, naphthalene, phenanthrene, fluorene, carbazole, dibenzofuran, and dibenzothiophene.

In Formulae 1-1 and 1-2, R11 to R14 may each independently be selected from a group represented by *-(L13)a13-(Ar13)b13, hydrogen, deuterium, —F, —Cl, —Br, —I, a hydroxyl group, a cyano group, a nitro group, an amidino group, a hydrazine group, a hydrazone group, a C1-C60 alkyl group, a C2-C60 alkenyl group, a C2-C60 alkynyl group, a C1-C60 alkoxy group, a C3-C10 cycloalkyl group, a C1-C10 heterocycloalkyl group, a C3-C10 cycloalkenyl group, a C1-C10 heterocycloalkenyl group, a π electron-deficient nitrogen-free cyclic group, —Si(Q1)(Q2)(Q3), —N(Q1)(Q2), and —B(Q1)(Q2), wherein Q1 to Q3 may each independently be selected from hydrogen, deuterium, a C1-C60 alkyl group, a C2-C60 alkenyl group, a C2-C60 alkynyl group, a C1-C60 alkoxy group, a π electron-deficient nitrogen-free cyclic group, a biphenyl group, and a terphenyl group.

For example, Q1 to Q3 may each independently be selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, and a terphenyl group.

c11 to c14 indicate the numbers of R11 to R14, respectively, and may each independently be an integer from 1 to 8. When c11 is 2 or more, two or more R11(s) may be identical to or different from each other, when c12 is 2 or more, two or more R12(s) may be identical to or different from each other, when c13 is 2 or more, two or more R13(s) may be identical to or different from each other, and when c14 is 2 or more, two or more R14(s) may be identical to or different from each other.

In Formulae 1-1 and 1-2, L11 to L13 may each independently be selected from:

a single bond and a π electron-deficient nitrogen-free cyclic group; and a π electron-deficient nitrogen-free cyclic group substituted with at least one selected from deuterium, a cyano group, a C1-C60 alkyl group, a C1-C60 alkoxy group, and a π electron-deficient nitrogen-free cyclic group.

For example, L11 to L13 may each independently be selected from:

a single bond, a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group; and a benzene group, a heptalene group, an indene group, a naphthalene group, an azulene group, a heptalene group, an indacene group, an acenaphthylene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentacene group, a hexacene group, a pentaphene group, a rubicene group, a coronene group, an ovalene group, a pyrrole group, an isoindole group, an indole group, a furan group, a thiophene group, a benzofuran group, a benzothiophene group, a benzosilole group, a benzocarbazole group, a dibenzocarbazole group, a dibenzofuran group, a dibenzothiophene group, a dibenzothiophene sulfone group, a carbazole group, a dibenzosilole group, an indenocarbazole group, an indolocarbazole group, a benzofurocarbazole group, a benzothienocarbazole group, a benzosilolocarbazole group, a triindolobenzene group, an acridine group, or a dihydroacridine group, each substituted with at least one selected from deuterium, a C1-C10 alkyl group, a C1-C10 alkoxy group, a phenyl group, a naphthyl group, a fluorenyl group, a carbazolyl group, a dibenzofuranyl group, a dibenzothiophenyl group, a triphenylenyl group, a biphenyl group, and a terphenyl group.

a11 to a13 indicate the numbers of L11 to L13, respectively, and may each independently be an integer from 1 to 3. When a11 is 2 or more, two or more L11(s) may be identical to or different from each other, when a12 is 2 or more, two or more L12(s) may be identical to or different from each other, and when a13 is 2 or more, two or more L13(s) may be identical to or different from each other. However, when each of L11 to L13 is a single bond, each of a11 to a13 is 1.

In Formulae 1-1 and 1-2, Ar11 to Ar13 may each independently be selected from:

a π electron-deficient nitrogen-free cyclic group;

a π electron-deficient nitrogen-free cyclic group substituted with at least one selected from deuterium, a cyano group, a C1-C60 alkyl group, a C1-C60 alkoxy group, and a π electron-deficient nitrogen-free cyclic group; and —Si(Q1)(Q2)(Q3) and —N(Q1)(Q2), wherein Q1 to Q3 may each independently be selected from hydrogen, deuterium, a C1-C60 alkyl group, a C2-C60 alkenyl group, a C2-C60 alkynyl group, a C1-C60 alkoxy group, a π electron-deficient nitrogen-free cyclic group, a biphenyl group, and a terphenyl group.

For example, Ar11 to Ar13 may each independently be selected from:

a phenyl group, a biphenyl group, a terphenyl group, a tetraphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, an isoindolyl group, an indolyl group, a furanyl group, a thiophenyl group, a benzofuranyl group, a benzothiophenyl group, a benzosilolyl group, a dibenzofuranyl group, a dibenzothiophenyl group, a carbazolyl group, a benzocarbazolyl group, a dibenzocarbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group and dihydroacridinyl group;

a phenyl group, a biphenyl group, a terphenyl group, a tetraphenyl group, a naphthyl group, a fluorenyl group, a spiro-bifluorenyl group, a benzofluorenyl group, a dibenzofluorenyl group, a phenanthrenyl group, an anthracenyl group, a triphenylenyl group, a pyrenyl group, a chrysenyl group, a pyrrolyl group, an isoindolyl group, an indolyl group, a furanyl group, a thiophenyl group, a benzofuranyl group, a benzothiophenyl group, a benzosilolyl group, a dibenzofuranyl group, a dibenzothiophenyl group, a carbazolyl group, a benzocarbazolyl group, a dibenzocarbazolyl group, a dibenzosilolyl group, an indenocarbazolyl group, an indolocarbazolyl group, a benzofurocarbazolyl group, a benzothienocarbazolyl group, a benzosilolocarbazolyl group, an acridinyl group and dihydroacridinyl group, each substituted with at least one selected from deuterium, a C1-C10 alkyl group, a C1-C10 alkoxy group, a phenyl group, a naphthyl group, a fluorenyl group, a carbazolyl group, a dibenzofuranyl group, a dibenzothiophenyl group, a triphenylenyl group, a biphenyl group, and a terphenyl group;

—Si(Q1)(Q2)(Q3) and —N(Q1)(Q2), wherein Q1 to Q3 may each independently be selected from hydrogen, deuterium, a C1-C10 alkyl group, a C1-C10 alkoxy group, a phenyl group, a naphthyl group, a fluorenyl group, a carbazolyl group, a dibenzofuranyl group, a dibenzothiophenyl group, a triphenylenyl group, a biphenyl group, and a terphenyl group.

b11 to b13 indicate the numbers of Ar11 to Ar13, respectively, and may each independently be an integer from 1 to 5. When b11 is 2 or more, two or more Ar11(s) may be identical to or different from each other, when b12 is 2 or more, two or more Ar12(s) may be identical to or different from each other, and when b13 is 2 or more, two or more Ar13(s) may be identical to or different from each other.

In some exemplary embodiments, the first host may be selected from Compounds 1-1 to 1-22, but the exemplary embodiments are not limited thereto:

-continued
1-1
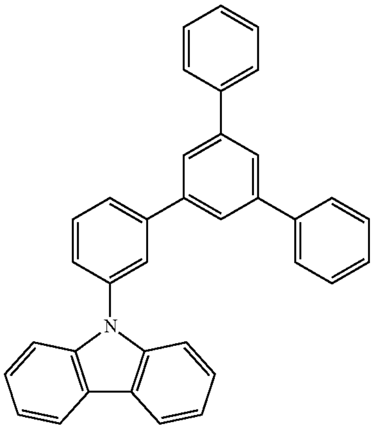
1-2
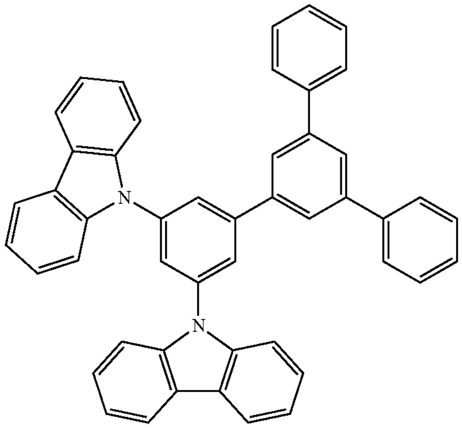
1-3
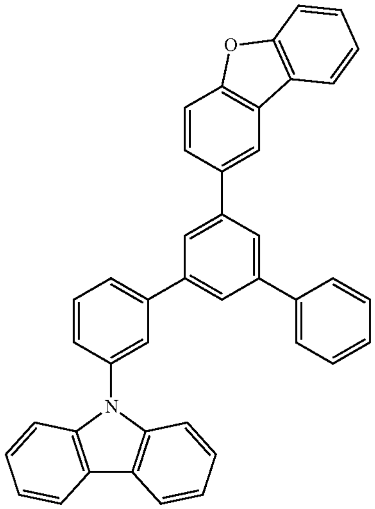
1-4
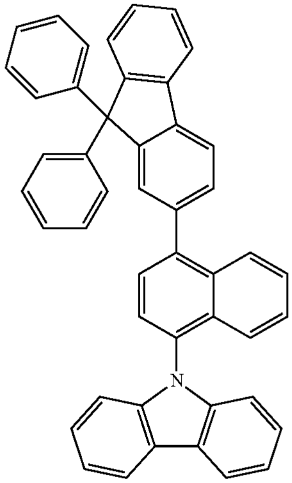
1-5
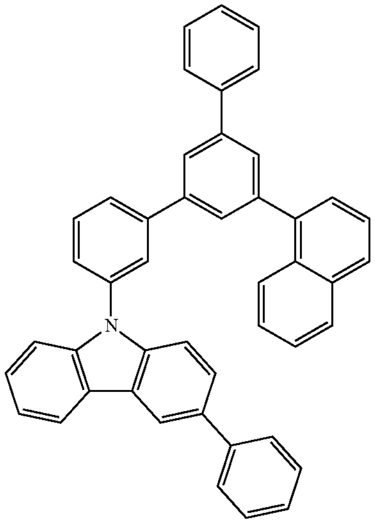
1-6
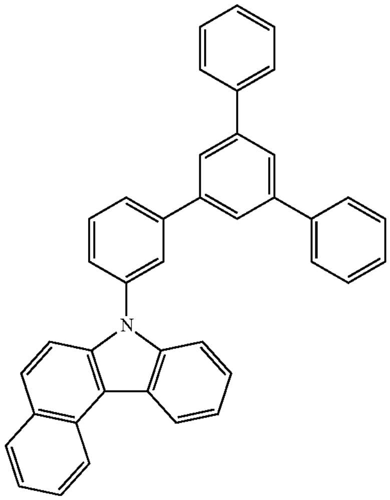

-continued
1-7
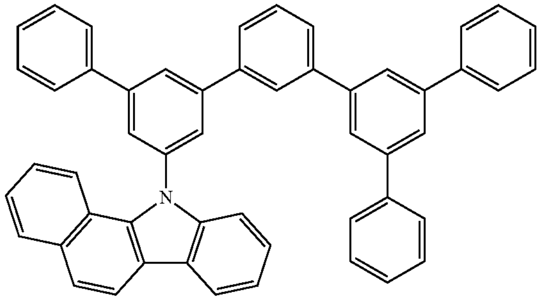
1-8
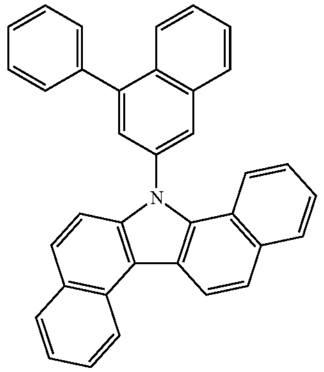
1-9
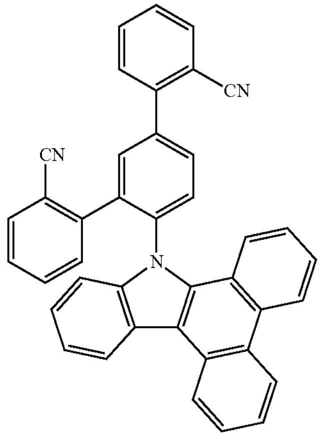
1-10
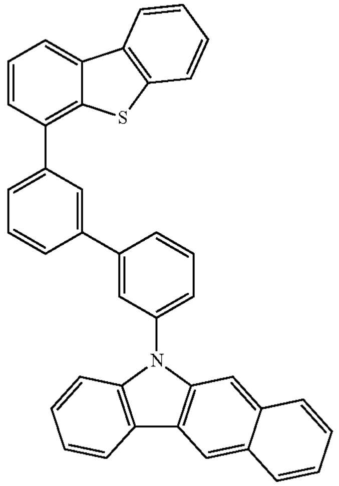
-continued
1-11
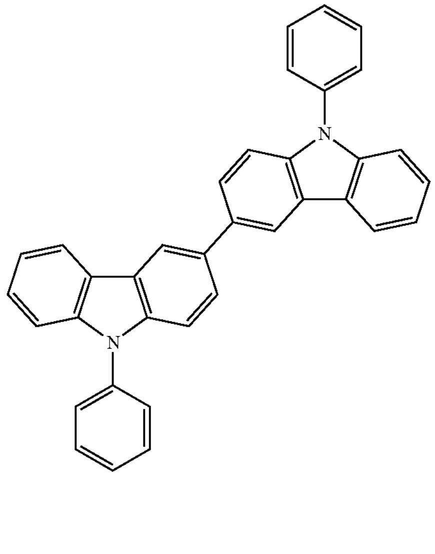
1-12
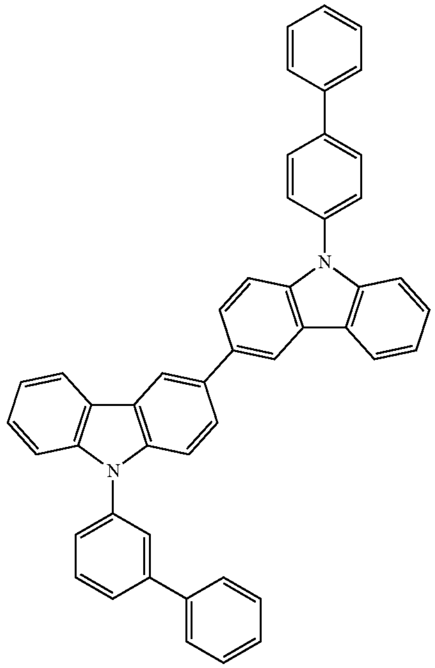

-continued
1-13
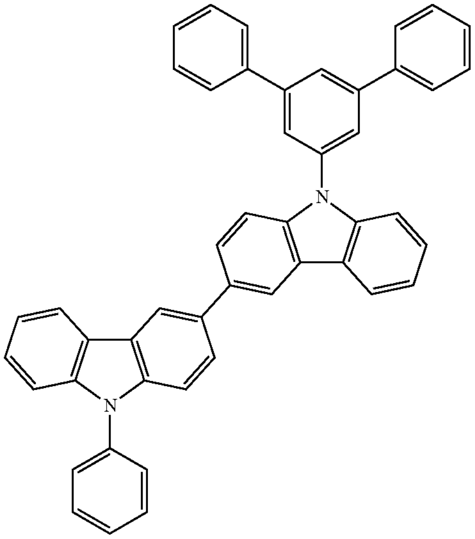
1-14
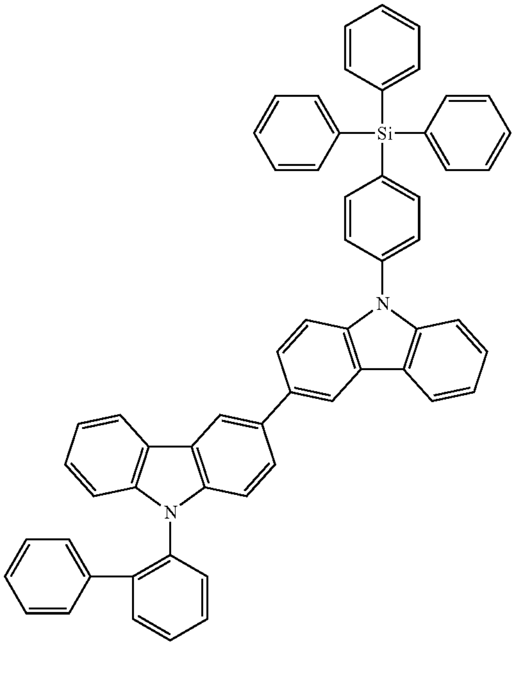
-continued
1-15
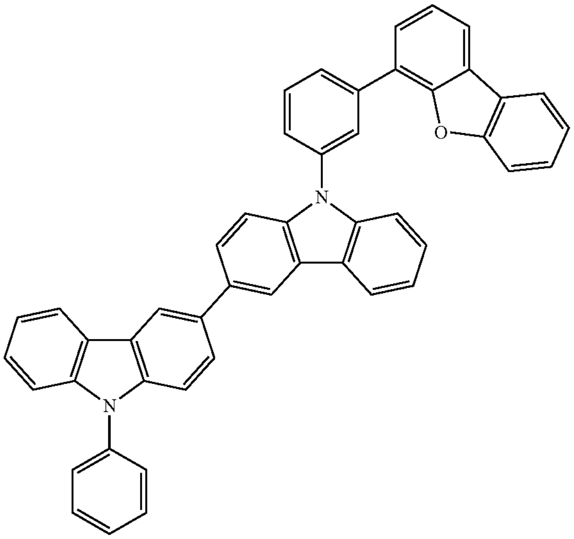
1-16
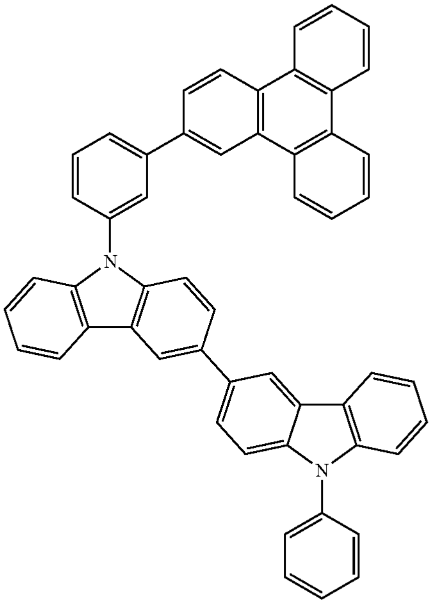
1-17
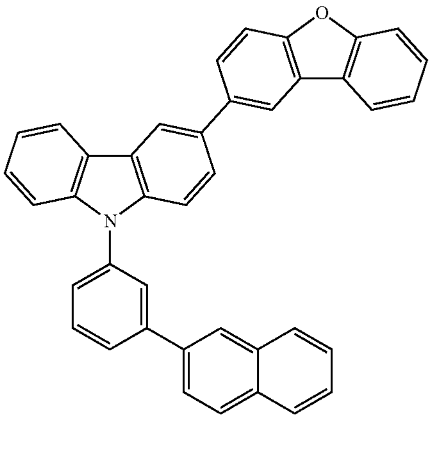

-continued 1-18

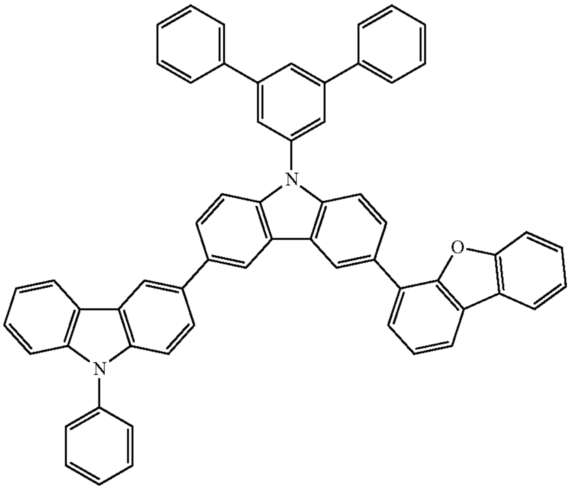

1-19

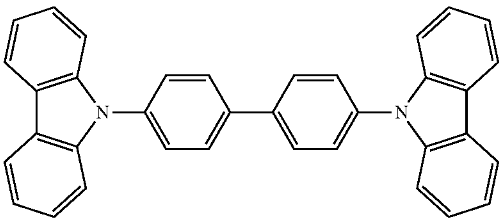

1-20

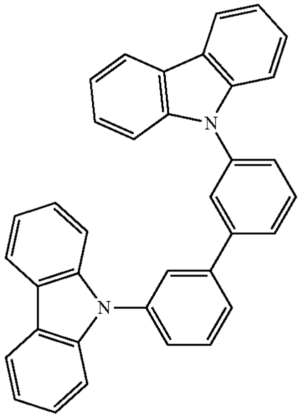

1-21

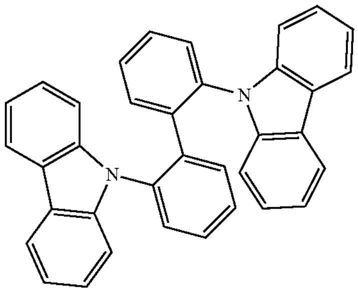

-continued 1-22

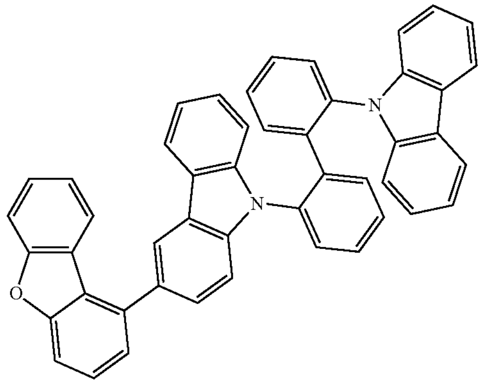

In some exemplary embodiments, the electron transport host may include at least one electron withdrawing group, and the bipolar host may include at least one electron withdrawing group and at least one electron donating group.

In some exemplary embodiments, the electron withdrawing group may be selected from:

—F, —$CFH_2$, —$CF_2H$, —$CF_3$, —CN, and —$NO_2$;

a $C_1$-$C_{60}$ alkyl group substituted with at least one selected from —F, —$CFH_2$, —$CF_2H$, —$CF_3$, —CN, and —$NO_2$; and a substituted or unsubstituted π electron-deficient nitrogen-containing cyclic group.

In some exemplary embodiments, the electron donating group may be selected from a substituted or unsubstituted carbazole group, a substituted or unsubstituted dibenzofuran group, a substituted or unsubstituted dibenzothiophene group, a substituted or unsubstituted indolocarbazole group, a substituted or unsubstituted benzofurocarbazole group, a substituted or unsubstituted benzothienocarbazole group, a substituted or unsubstituted acridine group, a substituted or unsubstituted phenoxazine group, a substituted or unsubstituted phenothiazine group, a substituted or unsubstituted phenazine group, and —$N(Q_1)(Q_2)$, wherein $Q_1$ and $Q_2$ may each independently be selected from hydrogen, deuterium, a $C_1$-$C_{60}$ alkyl group, a $C_2$-$C_{60}$ alkenyl group, a $C_2$-$C_{60}$ alkynyl group, a $C_1$-$C_{60}$ alkoxy group, a π electron-deficient nitrogen-free cyclic group, a biphenyl group, and a terphenyl group.

In some exemplary embodiments, the second host may include at least one of compounds represented by Formulae 2-1, 2-2, and 2-3.

<Formula 2-1>

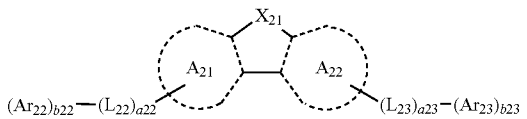

<Formula 2-2>

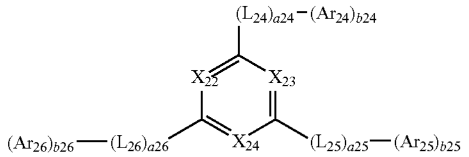

-continued

<Formula 2-3>

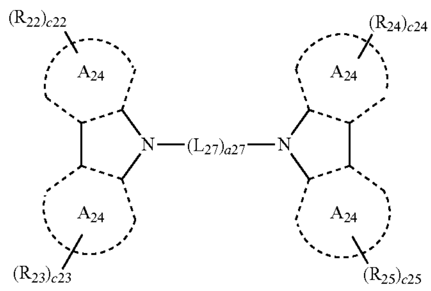

In Formulae 2-1 to 2-3,

A21 to A26 may each independently be selected from a $C_5$-C60 carbocyclic group and a C1-C60 heterocyclic group, X21 may be N-[(L21)a21-(Ar21)b21], O, or S, X22 to X24 may each independently be selected from N and C(R21), wherein at least one of X22 to X24 may be N, L21 to L27 may each independently be selected from a single bond, a substituted or unsubstituted C5-C60 carbocyclic group, and a substituted or unsubstituted C1-C60 heterocyclic group, a21 to a27 may each independently be selected from integer from 1 to 3, Ar21 to Ar26 and R21 to R25 may each independently be selected from hydrogen, deuterium, —F, —Cl, —Br, —I, a hydroxyl group, a cyano group, a nitro group, an amidino group, a hydrazine group, a hydrazone group, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C1-C10 heterocycloalkyl group, a substituted or unsubstituted C3-C10 cycloalkenyl group, a substituted or unsubstituted C1-C10 heterocycloalkenyl group, a substituted or unsubstituted C6-C60 aryl group, a substituted or unsubstituted C6-C60 aryloxy group, a substituted or unsubstituted C6-C60 arylthio group, a substituted or unsubstituted C1-C60 heteroaryl group, a substituted or unsubstituted monovalent non-aromatic condensed polycyclic group, a substituted or unsubstituted monovalent non-aromatic condensed heteropolycyclic group, —Si(Q1)(Q2)(Q3), —N(Q1)(Q2), —B(Q1)(Q2), —C(=O)(Q1), —S(=O)2(Q1), and —P(=O)(Q1)(Q2), b21 to b26 may each independently be an integer from 1 to 5, c22 to c25 may each independently be an integer from 1 to 8, in Formula 2-1, at least one of A21, A22, L21 to L23, and Ar2 to Ar23 may include a π electron-deficient nitrogen-containing cyclic group, in Formula 2-3, at least one of R22 to R25 may include an electron withdrawing group, and at least one substituent of the substituted $C_5$-C60 carbocyclic group, the substituted C1-C60 heterocyclic group, the substituted C1-C60 alkyl group, the substituted C2-C60 alkenyl group, the substituted C2-C60 alkynyl group, the substituted C1-C60 alkoxy group, the substituted C3-C10 cycloalkyl group, the substituted C1-C10 heterocycloalkyl group, the substituted C3-C10 cycloalkenyl group, the substituted C1-C10 heterocycloalkenyl group, the substituted C6-C60 aryl group, the substituted C6-C60 aryloxy group, the substituted C6-C60 arylthio group, the substituted C1-C60 heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a C1-C60 alkyl group, a C2-C60 alkenyl group, a C2-C60 alkynyl group, and a C1-C60 alkoxy group;

a C1-C60 alkyl group, a C2-C60 alkenyl group, a C2-C60 alkynyl group, and a C1-C60 alkoxy group, each substituted with at least one selected from deuterium, —F, —Cl, —Br, —I, a hydroxyl group, a cyano group, a nitro group, an amidino group, a hydrazino group, a hydrazono group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic condensed polycyclic group, a monovalent non-aromatic condensed heteropolycyclic group, —Si(Q11)(Q12)(Q13), —N(Q11)(Q12), —B(Q11)(Q12), —C(=O)(Q11), —S(=O)2(Q11), and —P(=O)(Q11)(Q12);

a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic condensed polycyclic group, and a monovalent non-aromatic condensed heteropolycyclic group;

a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a C1-C60 alkyl group, a C2-C60 alkenyl group, a C2-C60 alkynyl group, a C1-C60 alkoxy group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic condensed polycyclic group, a monovalent non-aromatic condensed heteropolycyclic group, —Si(Q21)(Q22)(Q23), —N(Q21)(Q22), —B(Q21)(Q22), —C(=O)(Q21), —S(=O)2(Q21), and —P(=O)(Q21)(Q22); and —Si(Q31)(Q32)(Q33), —N(Q31)(Q32), —B(Q31)(Q32), —C(=O)(Q31), —S(=O)2(Q31), and —P(=O)(Q31)(Q32), wherein Q1 to Q3, Q11 to Q13, Q21 to Q23, and Q31 to Q33 may each independently be selected from hydrogen, deuterium, —F, —Cl, —Br, —I, a hydroxyl group, a cyano group, a nitro group, an amidino group, a hydrazino group, a hydrazono group, a C1-C60 alkyl group, a C2-C60 alkenyl group, a C2-C60 alkynyl group, a C1-C60 alkoxy group, a C3-C10 cycloalkyl group, a C1-C10 heterocycloalkyl group, a C3-C10 cycloalkenyl group, a C1-C10 heterocycloalkenyl group, a C6-C60 aryl group, a C6-C60 aryloxy group, a C6-C60 arylthio group, a C1-C60 heteroaryl group, a monovalent non-aromatic condensed polycyclic group, a monovalent non-aromatic condensed heteropolycyclic group, a biphenyl group, and a terphenyl group.

In some exemplary embodiments, in Formulae 2-1 and 2-3, A21 to A26 may each independently be selected from a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, and an azadibenzosilole group.

In some exemplary embodiments, in Formulae 2-1 to 2-3, L21 to L27 may each independently be selected from: a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, and an azadibenzosilole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, and an azadibenzosilole group, each substituted with at least one of deuterium, —F, —Cl, —Br, —I, a hydroxyl group, a cyano group, a nitro group, an amidino group, a hydrazine group, a hydrazone group, a C1-C20 alkyl group, a C1-C20 alkoxy group, a phenyl group, a naphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a dibenzofuranyl group, a dibenzothiophenyl group, a carbazolyl group, an imidazolyl group, a pyrazolyl group, a thiazolyl group, an isothiazolyl group, an oxazolyl group, an isoxazolyl group, a pyridinyl group, a pyrazinyl group, a pyridazinyl group, a pyrimidinyl group, an indazolyl group, a purinyl group, a quinolinyl group, an isoquinolinyl group, a benzoquinolinyl group, a benzoisoquinolinyl group, a phthalazinyl group, a naphthyridinyl group, a quinoxalinyl group, a benzoquinoxalinyl group, a quinazolinyl group, a cinnolinyl group, a phenanthridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an oxadiazolyl group, a triazinyl group, a thiadiazolyl group, an imidazopyridinyl group, an imidazopyrimidinyl group, an azaindenyl group, an azaindolyl group, an azabenzofuranyl group, an azabenzothiophenyl group, an azabenzosilolyl group, an azafluorenyl group, an azacarbazolyl group, an azadibenzofuranyl group, an azadibenzothiophenyl group, and an azadibenzosilolyl group, —Si(Q31)(Q32)(Q33), —N(Q31)(Q32), —B(Q31)(Q32), —C(=O)(Q31), —S(=O)2(Q31), and —P(=O)(Q31)(Q32), wherein Q31 to Q33 may each independently be selected from a C1-C10 alkyl group, a C1-C10 alkoxy group, a phenyl group, a phenyl group substituted with a C1-C10 alkyl group, a biphenyl group, a terphenyl group, and a naphthyl group.

In some exemplary embodiments, in Formula 2-1, at least one of A21, A22, L21 to L23, and Ar21 to Ar23 may be selected from an imidazole group, a pyrazole group, a thiazole group, an isothiazole group, an oxazole group, an isoxazole group, a pyridine group, a pyrazine group, a pyridazine group, a pyrimidine group, an indazole group, a purine group, a quinoline group, an isoquinoline group, a benzoquinoline group, a benzoisoquinoline group, a phthalazine group, a naphthyridine group, a quinoxaline group, a benzoquinoxaline group, a quinazoline group, a cinnoline group, a phenanthridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, an azaindene group, an azaindole group, an azabenzofuran group, an azabenzothiophene group, an azabenzosilole group, an azafluorene group, an azacarbazole group, an azadibenzofuran group, an azadibenzothiophene group, and an azadibenzosilole group.

For example, when at least one of L21 to L23 includes a π electron-deficient nitrogen-containing cyclic group, the at least one of L21 to L23 may include a divalent, trivalent, or tetravalent group of the aforementioned group. For example, when at least one of Ar21 to Ar23 includes a π electron-deficient nitrogen-containing cyclic group, the at least one of Ar21 to Ar23 may include a monovalent group of the aforementioned group.

In some exemplary embodiments, in Formula 2-3, at least one of R22 to R25 may be selected from:

—F, —CFH2, —CF2H, —CF3, —CN, and —NO2;

a C1-C60 alkyl group substituted with at least one selected from —F, —CFH2, —CF2H, —CF3, —CN, and —NO2;

a substituted or unsubstituted electron-deficient nitrogen-containing cyclic group.

In some exemplary embodiments, the second host may be selected from Compounds 2-1 to 2-30, but the exemplary embodiments are not limited thereto:

2-1

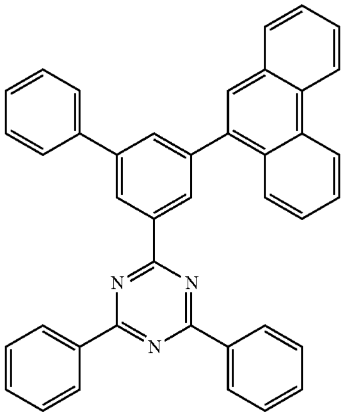

-continued 2-2

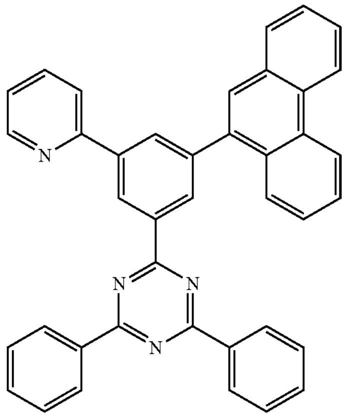

2-3

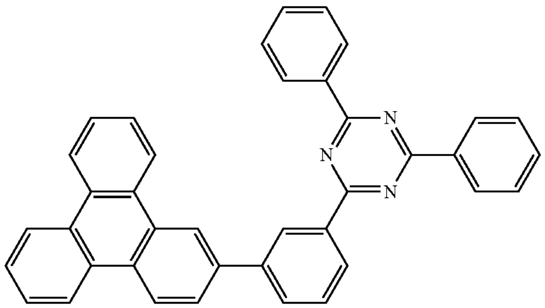

2-4

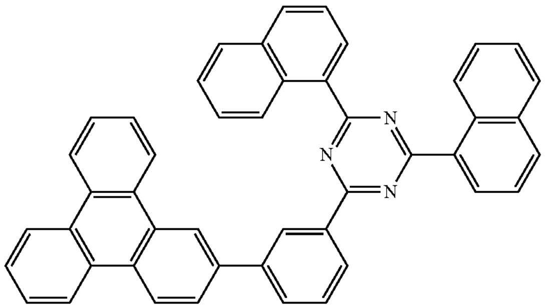

-continued
2-5
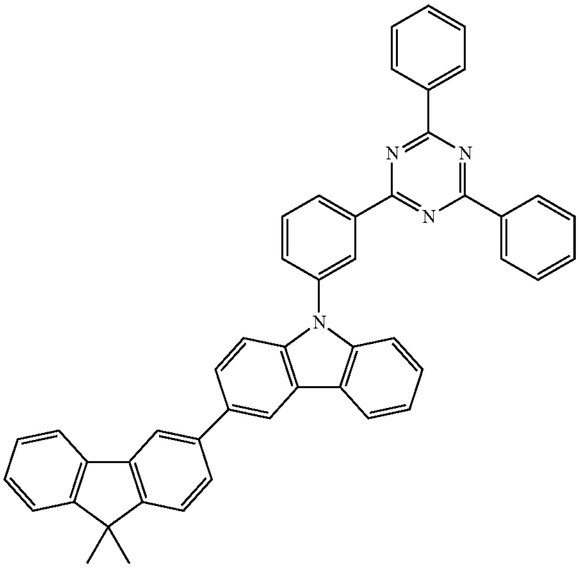
2-6
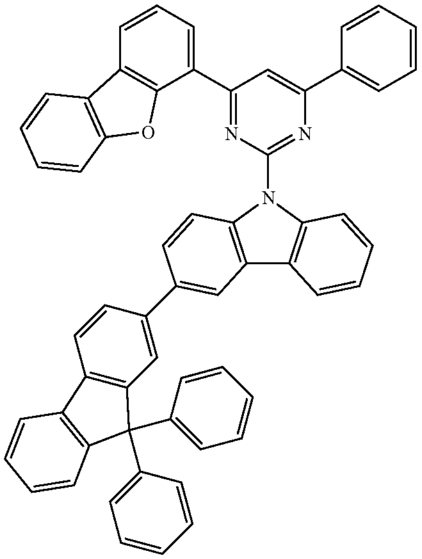
2-7
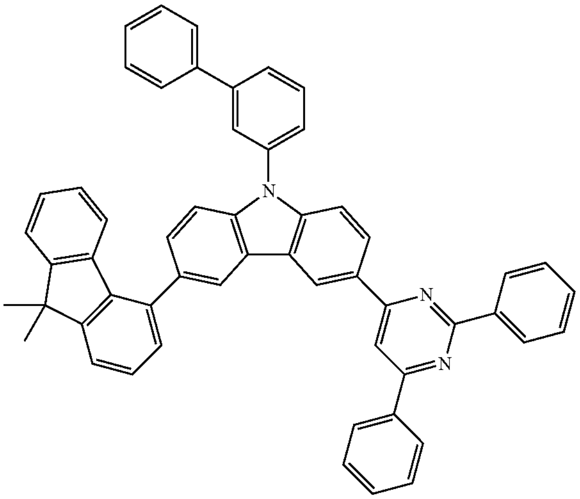
-continued
2-8
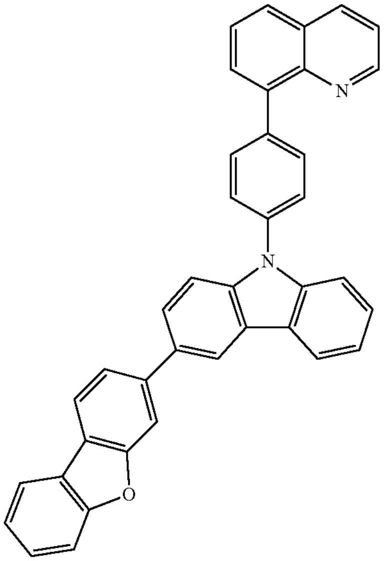
2-9
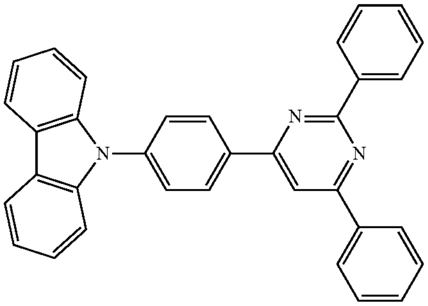
2-10
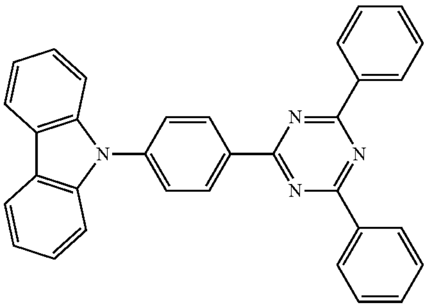
2-11
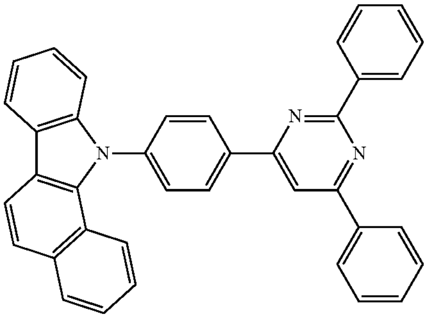

-continued
2-12
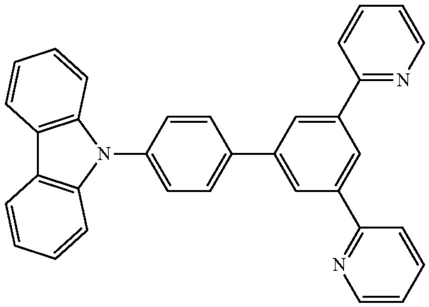
2-13
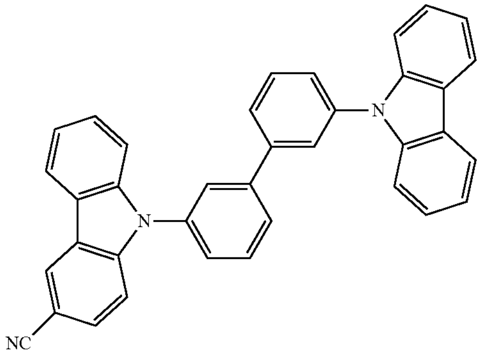
2-14
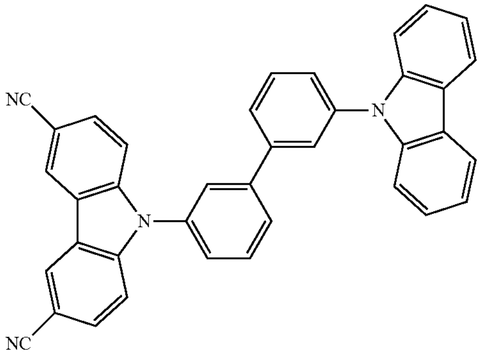
2-15
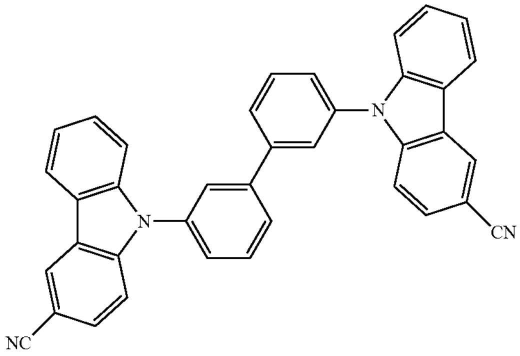
-continued
2-16
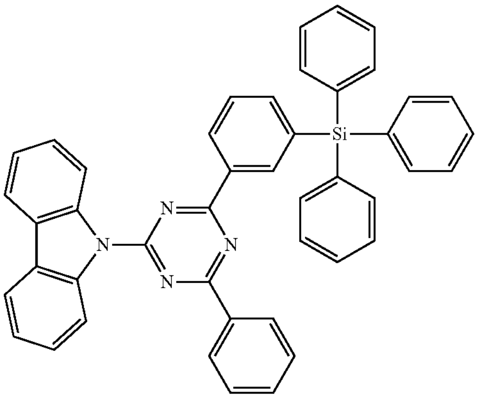
2-17
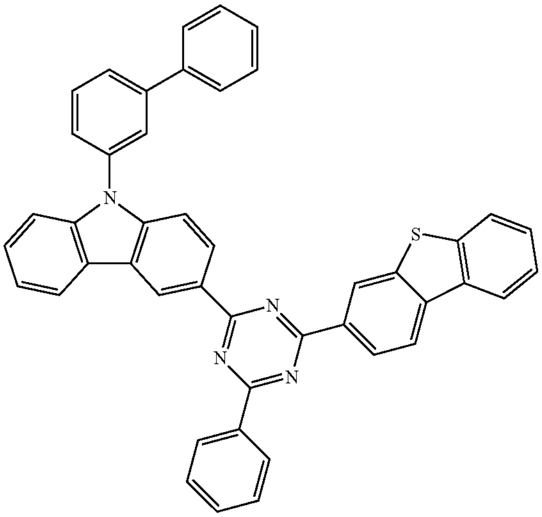
2-18
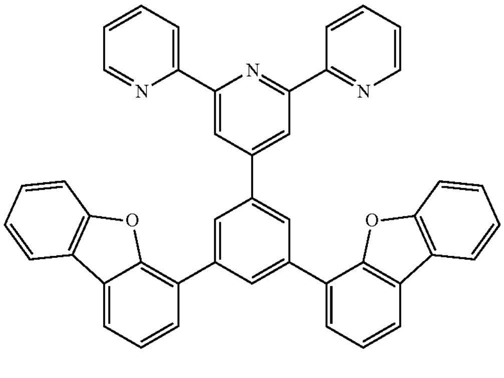

-continued
2-19
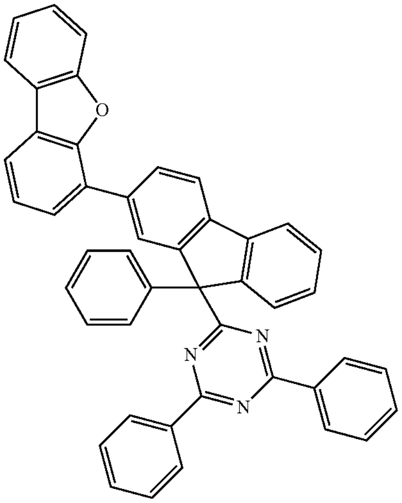
2-20
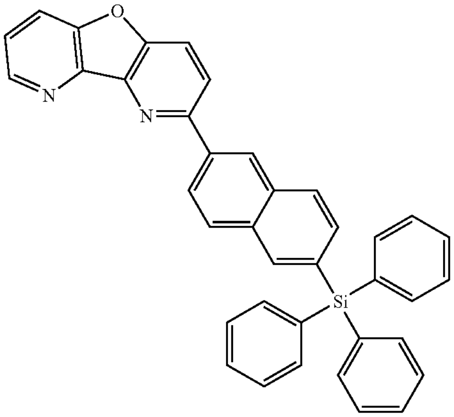
2-21
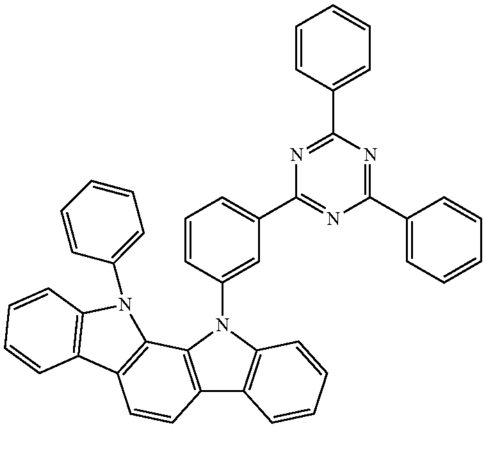
-continued
2-22
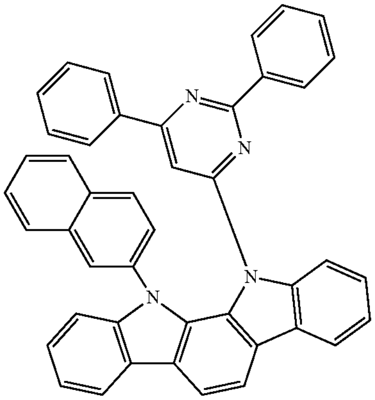
2-23
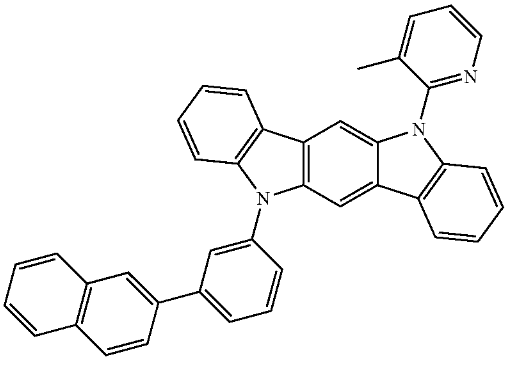
2-24
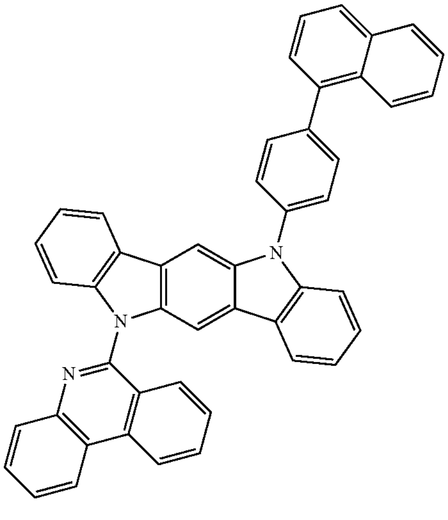

-continued
2-25
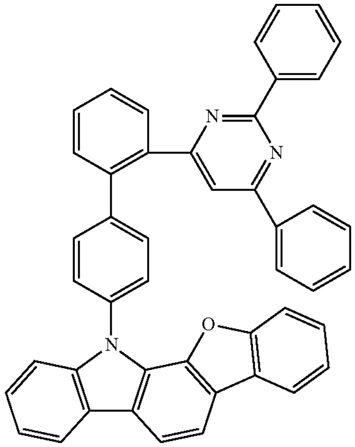
2-26
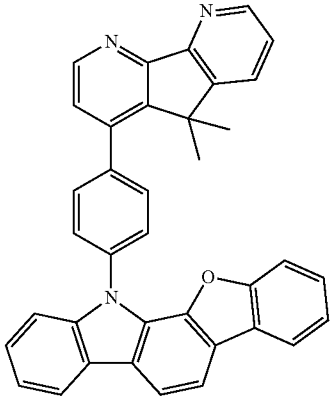
2-27
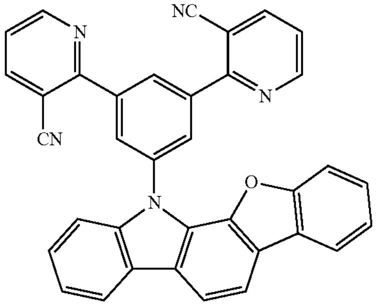
2-28
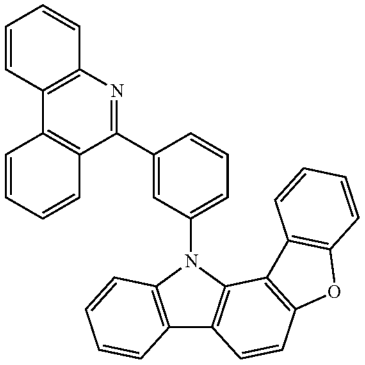
-continued
2-29
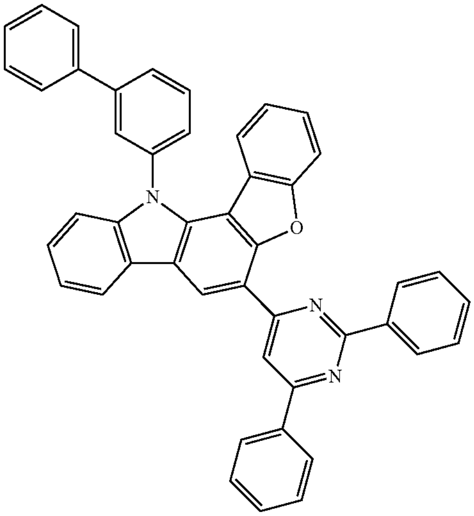
2-30
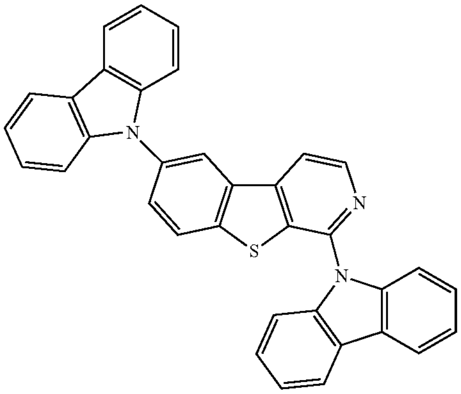
In some exemplary embodiments, the phosphorescent organometallic compound may be a compound represented by Formula 3:
<Formula 3>
$M_{31}(L_{31})_{n31}(L_{32})_{n32}$
<Formula 3A>
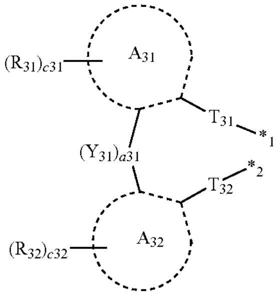

-continued

<Formula 3B>

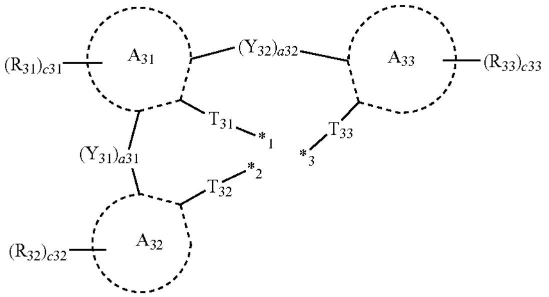

<Formula 3C>

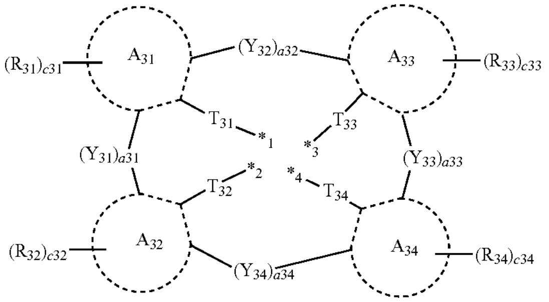

In Formula 3

$M_{31}$ may be selected from a Period 1 transition metal, a Period 2 transition metal, and a Period 3 transition metal, $L_{31}$ may be selected from a ligand represented by Formula 3A, a ligand represented by Formula 3B, and a ligand represented by Formula 3C, $L_{32}$ may be selected from a monodentate ligand, a bidentate ligand, and a tridentate ligand, n31 may be selected from 1 and 2, n32 may be selected from 0, 1, 2, 3, and 4, $A_{31}$ to $A_{34}$ may each independently be selected from a $C_5$-$C_{30}$ carbocyclic group and a $C_1$-$C_{30}$ heterocyclic group, $Y_{31}$ to $Y_{34}$ may each independently be selected from a single bond, a double bond, a substituted or unsubstituted $C_6$-$C_{30}$ arylene group, a substituted or unsubstituted $C_1$-$C_{30}$ heteroarylene group, *—O—*', *—S—*', *—C(=O)—*', *—S(=O)—*', *—C($R_{35}$)($R_{36}$)—*', *—C($R_{35}$)=C($R_{36}$)—*', *—C($R_{35}$)=*', *—Si($R_{35}$)($R_{36}$)—*', *—B($R_{35}$)—*', *—N($R_{35}$)—*', and *—P($R_{35}$)—*', a31 to a33 may each independently be selected from 1, 2, and 3, a34 may be selected from 0, 1, 2, and 3, wherein when a34 is 0, $A_{32}$ and $A_{34}$ may not be linked to each other, $Y_{31}$ to $Y_{34}$ may each independently be selected from a chemical bond, *—O—*', *—S—*', *—B($R_{37}$)—*', *—N($R_{37}$)—*', *—P($R_{37}$)—*', *—C($R_{37}$)($R_{38}$)—*', *—Si($R_{37}$)($R_{35}$)—*', *—Ge($R_{37}$)($R_3$)—*', *—C(=O)—*', and *—C(=S)—*', $*_1$, $*_2$, $*_3$, and $*_4$ each indicate a binding site to $M_{31}$, $R_{31}$ to $R_{38}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{60}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C($Q_1$)($Q_2$)($Q_3$), —Si($Q_1$)($Q_2$)($Q_3$), —B($Q_1$)($Q_2$), —N($Q_1$)($Q_2$), —P($Q_1$)($Q_2$), —C(=O)($Q_1$), —S(=O)($Q_1$), —S(=O)$_2$ ($Q_1$), —P(=O)($Q_1$)($Q_2$), and —P(=S)($Q_1$)($Q_2$), wherein adjacent groups among $R_{31}$ to $R_{38}$ may optionally be linked to each other to form a substituted or unsubstituted $C_5$-$C_{60}$ carbocyclic group or a substituted or unsubstituted $C_1$-$C_{60}$ heterocyclic group, Adjacent groups among $R_{31}$ to $R_{38}$ and $Y_{31}$ to $Y_{34}$ may optionally be linked to each other to form a substituted or unsubstituted $C_5$-$C_{60}$ carbocyclic group or a substituted or unsubstituted $C_1$-$C_{60}$ heterocyclic group, c31 to c34 may each independently be an integer from 0 to 10, and at least one substituent of the substituted $C_6$-$C_{30}$ arylene group, the substituted $C_1$-$C_{30}$ heteroarylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted $C_5$-$C_{60}$ carbocyclic group, and the substituted C1-$C_{60}$ heterocyclic group may be selected from:

deuterium, —F, —Cl, —Br, —I, a hydroxyl group, a cyano group, a nitro group, an amidino group, a hydrazino group, a hydrazono group, a C1-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, $—Si(Q_{21})(Q_{22})(Q_{23})$, $—N(Q_{21})(Q_{22})$, $—B(Q_{21})(Q_{22})$, $—C(=O)(Q_{21})$, $—S(=O)_2(Q_{21})$, and $—P(=O)(Q_{21})(Q_{22})$; and $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group.

In some exemplary embodiments, in Formula 3, $M_{31}$ may be selected from iridium (Ir), platinum (Pt), osmium (Os), ruthenium (Ru), rhodium (Rh), palladium (Pd), copper(Cu), silver (Au), gold (Au), titanium (Ti), zirconium (Zr), hafnium (Hf), europium (Eu), terbium (Tb), and thulium (Tm), but the exemplary embodiments are not limited thereto.

For example, in Formula 3, $M_{31}$ may be selected from Ir and Pt, but the exemplary embodiments are not limited thereto.

In some exemplary embodiments, in Formulae 3A to 3C, $A_{31}$ to $A_{34}$ may each independently be selected from a benzene group, a naphthalene group, an anthracene group, a phenanthrene group, a triphenylene group, a pyrene group, a chrysene group, a cyclopentadiene group, a 1,2,3,4-tetrahydronaphthalene group, a thiophene group, a furan group, a selenophene group, an indole group, a benzoborole group, a benzophosphole group, an indene group, a benzosilole group, a benzogermole group, a benzothiophene group, a benzoselenophene group, a benzofuran group, a carbazole group, a dibenzoborole group, a dibenzophosphole group, a fluorene group, a dibenzosilole group, a dibenzogermole group, a dibenzothiophene group, a dibenzoselenophene group, a dibenzofuran group, a dibenzothiophene 5-oxide group, a 9H-fluorene-9-one group, a dibenzothiophene 5,5-dioxide group, an azaindole group, an azabenzoborole group, an azabenzophosphole group, an azaindene group, an azabenzosilole group, an azabenzogermole group, an azabenzothiophene group, an azabenzoselenophene group, an azabenzofuran group, an azacarbazole group, an azadibenzoborole group, an azadibenzophosphole group, an azafluorene group, an azadibenzosilole group, an azadibenzogermole group, an azadibenzothiophene group, an azadibenzoselenophene group, an azadibenzofuran group, an azadibenzothiophene 5-oxide group, an aza-9H-fluorene-9-one group, an azadibenzothiophene 5,5-dioxide group, a pyridine group, a pyrimidine group, a pyrazine group, a pyridazine group, a triazine group, a quinoline group, an isoquinoline group, a quinoxaline group, a quinazoline group, a phenanthroline group, a pyrrole group, a pyrazole group, an imidazole group, a triazole group, an oxazole group, an isooxazole group, a thiazole group, an isothiazole group, an oxadiazole group, a thiadiazole group, a benzopyrazole group, a benzimidazole group, a benzoxazole group, a benzothiazole group, a benzoxadiazole group, a benzothiadiazole group, a 5,6,7,8-tetrahydroisoquinoline group, and a 5,6,7,8-tetrahydroquinoline group, but the exemplary embodiments are not limited thereto.

In some exemplary embodiments, in Formula 3A to 3C, $Y_{31}$ to $Y_{34}$ may each independently be selected from a single bond, a double bond, *—O—*', *—S—*', *—C($R_{35}$)($R_{36}$)—*', and *—N($R_{35}$)—*'.

In some exemplary embodiments, in Formula 3A to 3C, $R_{31}$ to $R_{38}$ may each independently be selected from:

hydrogen, deuterium, —F, —Cl, —Br, —I, a hydroxyl group, a cyano group, a nitro group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a pyrenyl group, a phenalenyl group, a phenanthrenyl group, an anthracenyl group, a fluoranthenyl group, a triphenylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, —$Si(Q_1)(Q_2)(Q_3)$, —$N(Q_1)(Q_2)$, and —$B(Q_1)(Q_2)$; and a cyclopentyl group, a cyclohexyl group, a cycloheptyl group, a cyclopentenyl group, a cyclohexenyl group, a phenyl group, a biphenyl group, a terphenyl group, a naphthyl group, a fluorenyl group, a spiro-bifluorenyl group, a spiro-fluorene-benzofluorenyl group, a benzofluorenyl group, a dibenzofluorenyl group, a pyrenyl group, a phenalenyl group, a phenanthrenyl group, an anthracenyl group, a fluoranthenyl group, a triphenylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, and an azadibenzosilolyl group, each substituted with at least one selected from deuterium, —F, —Cl, —Br, —I, a hydroxyl group, a cyano group, a nitro group, an amidino group, a hydrazine group, a hydrazone group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a naphthyl group, a fluorenyl group, a spiro-bifluorenyl group, a spiro-fluorene-benzofluorenyl group, a benzofluorenyl group, a dibenzofluorenyl group, a pyrenyl group, a phenalenyl group, a phenanthrenyl group, an anthracenyl group, a fluoranthenyl group, a triphenylenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a dibenzosilolyl group, a carbazolyl group, a benzocarbazolyl group, a dibenzocarbazolyl group, a thiadiazolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, a biphenyl group, and a terphenyl group, wherein $Q_1$ to $Q_3$ may each independently be selected from hydrogen, deuterium, a $C_1$-$C_{10}$ alkyl group, a $C_1$-$C_{10}$ alkoxy group, a phenyl group, a naphthyl group, a fluorenyl group, a carbazolyl group, a dibenzofuranyl group, a dibenzothiophenyl group, a triphenylenyl group, a biphenyl group, a terphenyl group, and a tetraphenyl group.

In some exemplary embodiments, the phosphorescent organometallic compound may include at least one of a compound represented by Formula 3-1 and a compound represented by Formula 3-2:

<Formula 3-1>

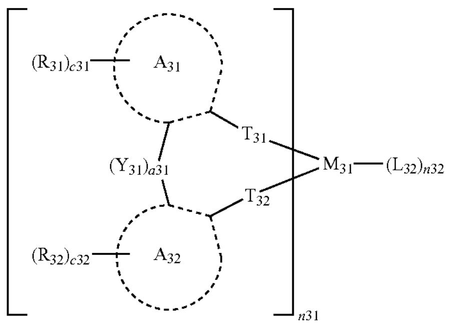

<Formula 3-2>

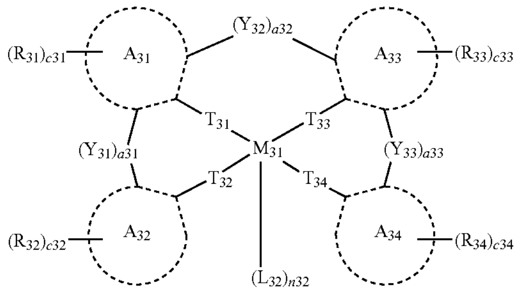

In Formulae 3-1 and 3-2, $M_{31}$, $L_{32}$, n31, n32, $A_{31}$ to $A_{34}$, $Y_{31}$ to $Y_{33}$, a31 to a33, $T_{31}$ to $T_{34}$, $R_{31}$ to $R_{34}$, and c31 to c34 are the same as described above.

In Formula 3-1, $M_{31}$ may be Ir.

In Formula 3-2, $M_{31}$ may be Pt.

In some exemplary embodiments, the phosphorescent organometallic compound may be selected from Compounds 3-11 to 3-18, but the exemplary embodiments are not limited thereto:

-continued 3-11

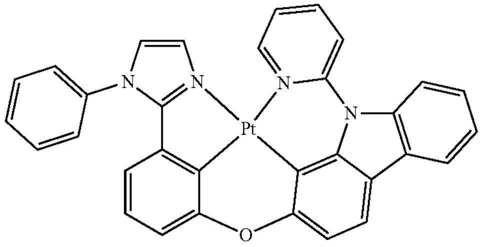

3-12

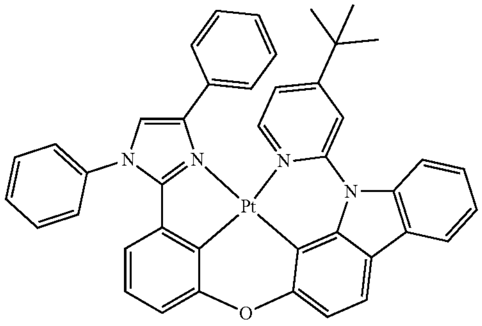

3-13

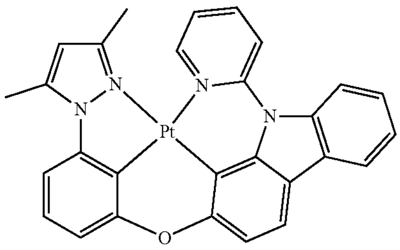

3-14

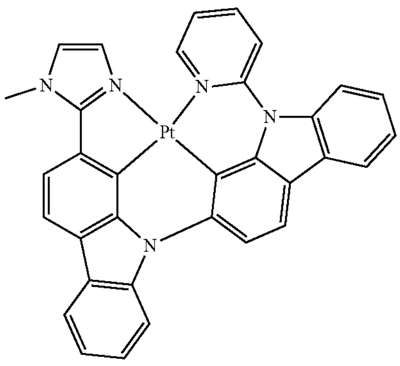

3-15

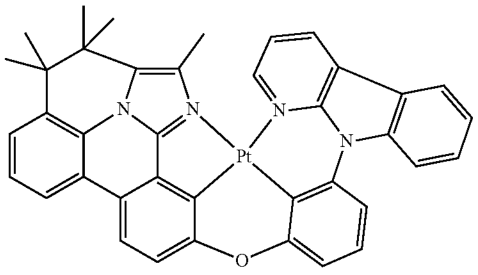

3-16

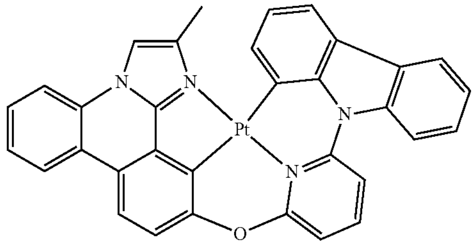

3-17

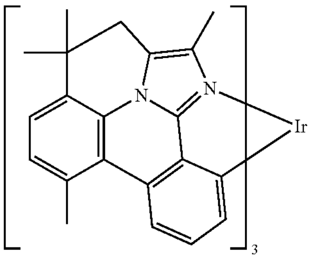

3-18

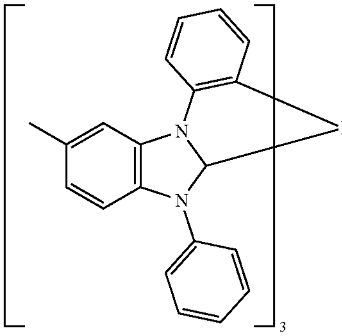

In some exemplary embodiments, the TADF compound may include at least one of compounds represented by Formulae 4-1 to 4-8:

<Formula 4-1>

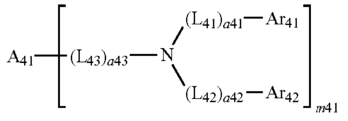

In Formula 4-1, $A_{41}$ may be a substituted or unsubstituted $C_5$-$C_{60}$ carbocyclic group or a substituted or unsubstituted $C_1$-$C_{60}$ heterocyclic group, $L_{41}$ to $L_{43}$ may each independently be selected from a substituted or unsubstituted $C_3$-$C_{10}$ cycloalkylene group, a substituted or unsubstituted C1-$C_{10}$ heterocycloalkylene group, a substituted or unsubstituted $C_3$-$C_{10}$ cycloalkenylene group, a substituted or unsubstituted C1-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a41 to a43 may each independently be an integer from 0 to 3, $Ar_{41}$ and $Ar_{42}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and m41 may be an integer from 1 to 6.

In some exemplary embodiments, in Formula 4-1, $A_{41}$ may be selected from: a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some exemplary embodiments, in Formula 4-1, $L_{41}$ to $L_{43}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In some exemplary embodiments, in Formula 4-1, $Ar_{41}$ and $Ar_{42}$ may ach independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —$Si(Q_{31})(Q_{32})(Q_{33})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

For example, in Formula 4-1, m41 may be 2, but the exemplary embodiments are not limited thereto.

<Formula 4-2>

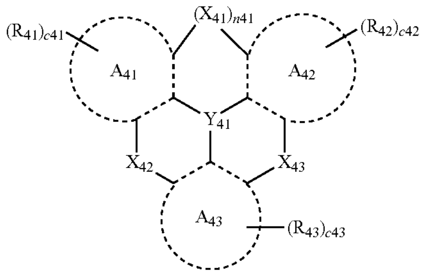

<Formula 4-3>

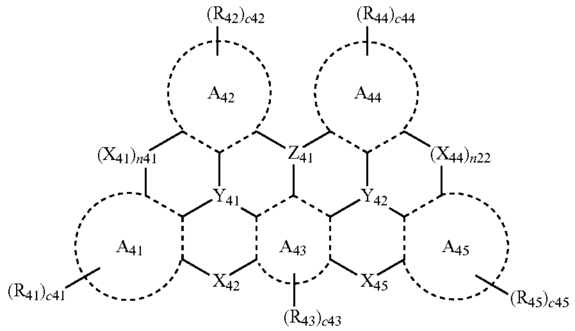

<Formula 4-4>

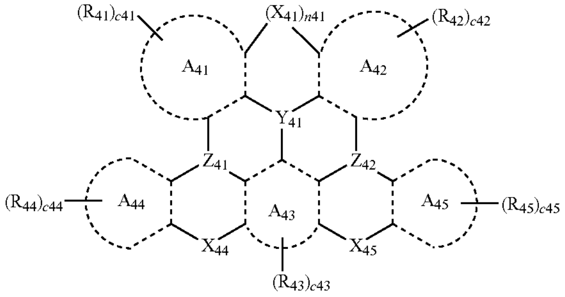

In Formulae 4-2 to 4-4, $X_{41}$ to $X_{47}$ may each independently be a single bond, O, S, $N(R_{46})$, $B(R_{46})$, $C(R_{46})(R_{47})$, or $Si(R_{46})(R_{47})$, n41 and n42 may each independently be 0, 1, or 2, wherein when n41 is 0, $A_{41}$ and $A_{42}$ may not linked to each other, and when n42 is 0, $A_{44}$ and $A_{45}$ may not be linked to each other, $Y_{41}$ and $Y_{42}$ may each independently be N, B, or P, $Z_{41}$ and $Z_{42}$ may each independently be N, $C(R_{46})$, or $S(R_{46})$, $A_{41}$ to $A_{45}$ may each independently be selected from a $C_5$-$C_{30}$ carbocyclic group and a $C_1$-$C_{30}$ heterocyclic group, $R_{41}$ to $R_{47}$ may each independently be selected from hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_6$ alkenyl group, a substituted or unsubstituted $C_2$-$C_{60}$ alkynyl group, a substituted or unsubstituted C1-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $-Si(Q_1)(Q_2)(Q_3)$, $-B(Q_1)(Q_2)$, $-C(=O)(Q_1)$, $-N(Q_1)(Q_2)$, $-P(=O)(Q_1)(Q_2)$, and $-S(=O)_2(Q_1)(Q_2)$, and c41 to c45 may each independently be an integer from 1 to 8.

In some exemplary embodiments, in Formulae 4-2 to 4-4, $X_{41}$ to X45 may each independently be $N(R_{46})$ or $B(R_{46})$, and $Y_{41}$ and $Y_{42}$ may each be B.

In some exemplary embodiments, in Formulae 4-2 to 4-4, n41 and n42 may each be 0.

In some exemplary embodiments, in Formulae 4-2 to 4-4, $Z_{41}$ and $Z_{42}$ may each be N.

$(EDG)_{b41}$-$[(L_{44})_{a44}$-$(EWG)_{t42}]_{s41}$ <Formula 4-5>

$(EWG)_{t42}$-$[(L_{44})_{a44}$-$(EDG)_{b41}]_{s42}$ <Formula 4-6>

$(EDG)_{b411}$d-$(L_{44})_{a44}$-$(EWG)_{t42}$-$(L_{45})_{a45}$-$(EDG)_{b412}$ <Formula 4-7>

$(EWG)_{t421}$-$(L_{44})_{a44}$-$(EDG)_{b41}$-$(L_{45})_{a45}$-$(EWG)_{t422}$ <Formula 4-8>

In Formulae 4-5 to 4-8,

EDG may be an electron donating group, and EWG may be an electron withdrawing group, b41, b411, b412, t42, t421, and t422 may each independently be selected from 1, 2, and 3, $L_{44}$ to $L_{45}$ may each independently be selected from a substituted or unsubstituted $C_3$-$C_{10}$ cycloalkylene group, a substituted or unsubstituted C1-C10 heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, a44 and a45 may each independently be an integer from 0 to 3, and s41 and s42 may each independently be an integer from 1 to 3.

In some exemplary embodiments, in Formulae 4-5 to 4-8, the electron donating group may be selected from a substituted or unsubstituted carbazole group, a substituted or unsubstituted dibenzofuran group, a substituted or unsubstituted dibenzothiophene group, a substituted or unsubstituted indolocarbazole group, a substituted or unsubstituted benzofurocarbazole group, a substituted or unsubstituted benzothienocarbazole group, a substituted or unsubstituted acridine group, a substituted or unsubstituted phenoxazine group, a substituted or unsubstituted penothiazine group, a substituted or unsubstituted phenazine group, and $-N(Q_1)(Q_2)$.

In some exemplary embodiments, in Formulae 4-5 to 4-8, the electron withdrawing group may be selected from:

—F, $-CFH_2$, $-CF_2H$, $-CF_3$, —CN, and $-NO_2$;

a $C_1$-$C_{60}$ alkyl group substituted with at least one selected from —F, $-CFH_2$, $-CF_2H$, $-CF_3$, —CN, and $-NO_2$;

a substituted or unsubstituted π electron-deficient nitrogen-containing cyclic group.

In Formulae 4-1 to 4-8, at least one substituent of the substituted $C_1$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$cycloalkyl group, the substituted $C_1$-$C_{10}$ heterocycloalkyl group, the substituted $C_3$-$C_{10}$cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, the substituted monovalent non-aromatic condensed heteropolycyclic group, the substituted carbazole group, the substituted dibenzofuran group, the substituted dibenzothiophene group, the substituted indolocarbazole group, the substituted benzofurocarbazole group, the substituted benzothienocarbazole group, the substituted acridine group, the substituted phenoxazine group, the substituted penothiazine group, the substituted phenazine group, and the substituted R electron-deficient nitrogen-containing cyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_1$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{11}$ heterocycloalkyl group, a $C_3$-$C_{10}$ cycloalkenyl group, a $C_1$-$C_{11}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), wherein $Q_1$ to $Q_3$, $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, and a terphenyl group.

The TADF compound may be a thermally activated delayed fluorescence emitter.

In some exemplary embodiments, the TADF compound may be selected from Compounds 4-1 to 4-13, but the exemplary embodiments are not limited thereto.

4-1

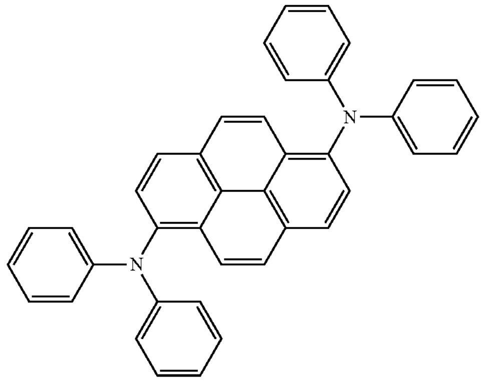

4-2

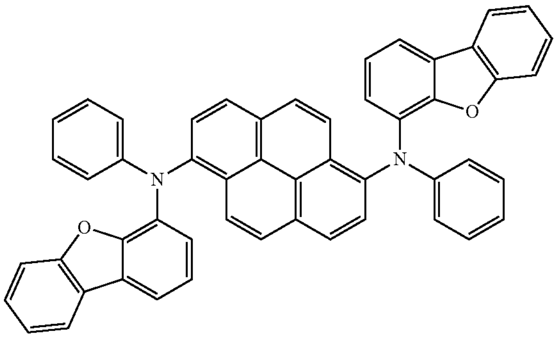

-continued
4-3
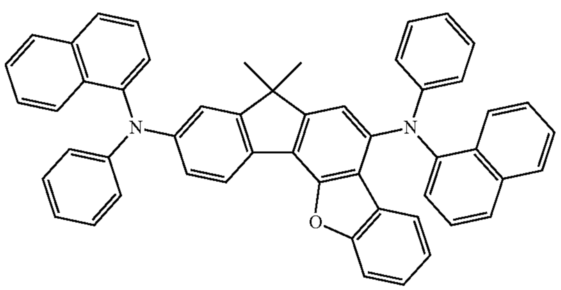
4-4
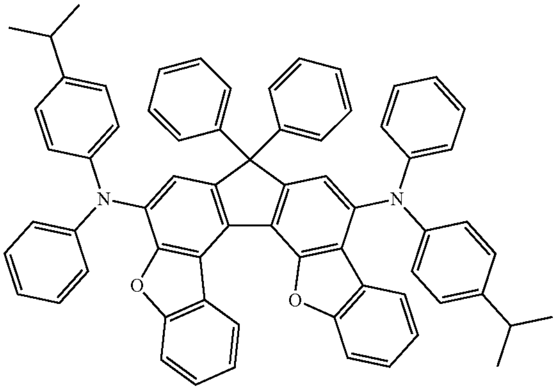
4-5
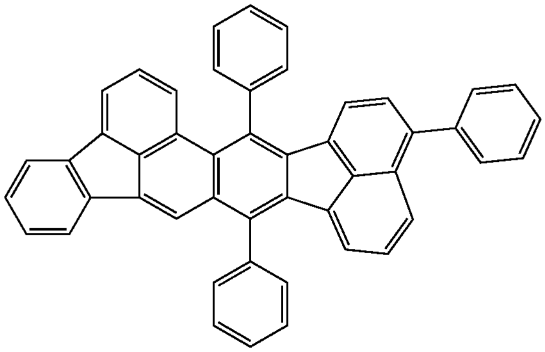
4-6
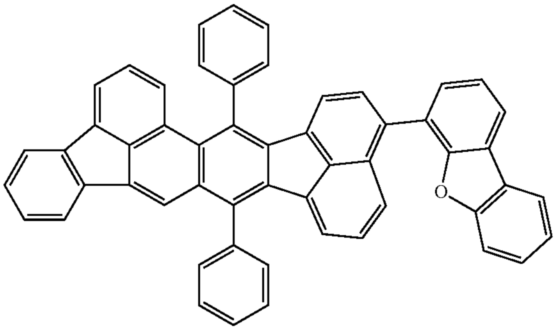
-continued
4-7
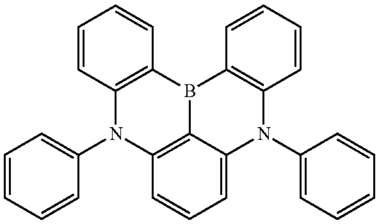
4-8
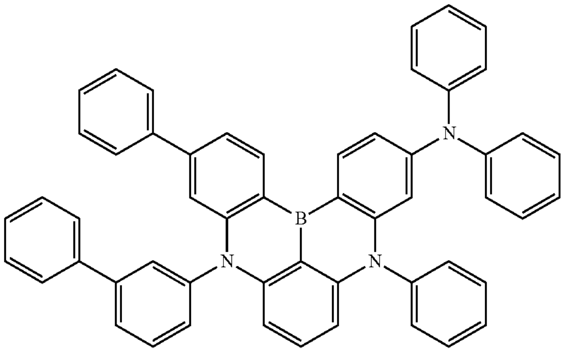
4-9
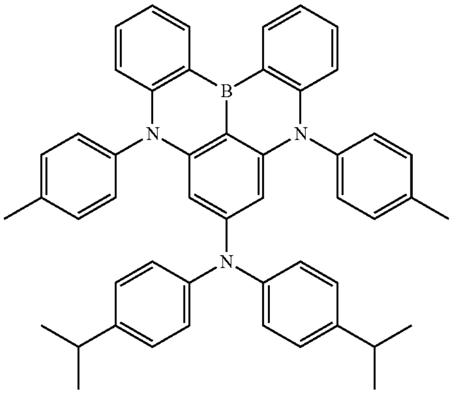
4-10
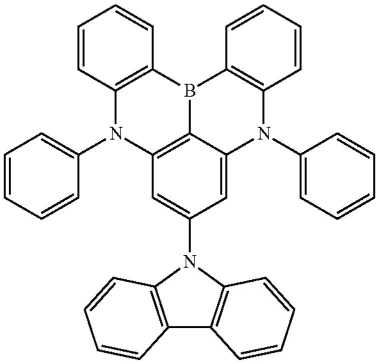

-continued 4-11

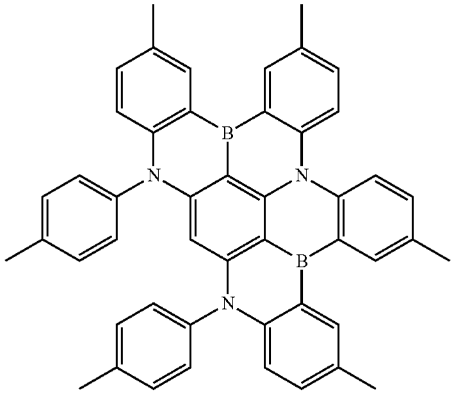

4-12

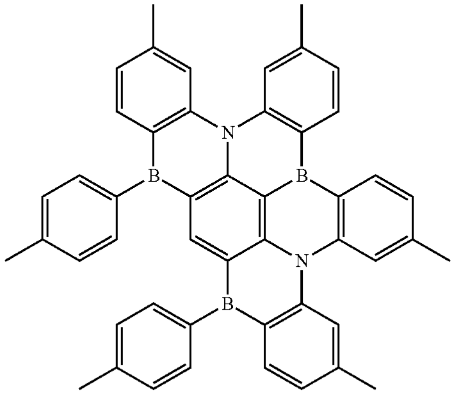

4-13

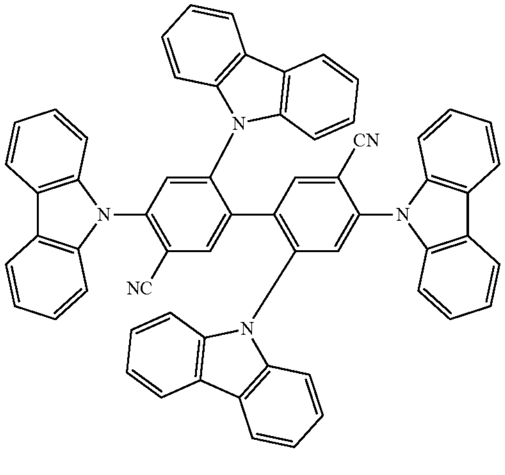

The organic light-emitting device includes a plurality of emission layers including a first emission layer and a second emission layer, and each of the plurality of emission layers includes different dopants (a first dopant, a second dopant). Thus, compared to an organic-light emitting device including different dopants in one emission layer, an emission zone is formed in the center of each of the first emission layer and the second emission layer, thereby reducing degradation of materials at an interface between a common layer and each of emission layer.

In some exemplary embodiments, the first dopant and the second dopant may each independently be a phosphorescent organometallic compound. In this regard, the first dopant and the second dopant are different organometallic compounds.

For example, a maximum emission wavelength of the first dopant and a maximum emission wavelength of the second dopant may be different from each other. Since the first dopant may substantially emit light in the first emission layer, and the second dopant may substantially emit light in the second emission layer, a maximum emission wavelength of light emitted from the first emission layer and a maximum emission wavelength of light emitted from the second emission layer may be different from each other. For example, the first emission layer may emit blue light, and the second emission layer may emit blue light. In this regard, maximum emission wavelengths of blue light respectively emitted from the first emission layer and the second emission layer may be different from each other.

For example, the first dopant and the second dopant may emit blue phosphorescence or blue delayed fluorescence by receiving energy from excitons formed in an emission layer. In this regard, a maximum emission wavelength of blue light emitted from the first dopant and a maximum emission wavelength of blue light emitted from the second dopant may be different from each other.

For example, a maximum emission wavelength of the first dopant may be in a range of about 440 nm to about 470 nm, and a maximum emission wavelength of the second dopant may be in a range of about 440 nm to about 470 nm.

In some exemplary embodiments, the first dopant and the second dopant may have different exciton lifetime ($\tau$). The exciton lifetime refers to measured excited-state lifespan.

In an organic light-emitting device according to an embodiment, a plurality of emission layers each include different dopants (first dopant and second dopant). Thus, compared to an organic light-emitting device including a plurality of dopants in one emission layer, a charge balance in an emission layer may be optimized, and exciton concentration and an emission region of an emission layer may be appropriately adjusted. Accordingly, lifespan of the organic light-emitting device may be improved.

In some exemplary embodiments, the first emission layer of the organic light-emitting device may satisfy Equation 2.

$$|HOMO(D1)-HOMO(EML1(H1))| \leq 0.3 \text{ eV}$$ <Equation 2>

$$|HOMO(D1)-HOMO(EML1(H2))| \leq 0.3 \text{ eV}$$ <Equation 3>

In Equations 2 and 3,

HOMO(D1) is a highest occupied molecular orbital (HOMO) energy level (eV) of the first dopant, HOMO (EML1(H1)) is a HOMO energy level (eV) of a first host included in the first emission layer, and HOMO(EML1(H2)) is a HOMO energy level (eV) of a second host included in the first emission layer.

Each of HOMO(D1), HOMO(EML1(H1)), and HOMO (EML1(H2)) may be calculated using quantum chemical calculation. The structure optimization of the ground state is performed by a density functional theory (DFT) method at B3LYP level, using a Gaussian 09 program sold by Gaussian, Inc., Wallingford CT, 2009, and the value of the HOMO energy level in the optimized structure is calculated. As the basis set, 6-31G(d,p) may be used.

For example, the first dopant may have a deeper HOMO energy level than a first host included in the first emission layer and a second host included in the first emission layer.

In an organic light-emitting device satisfying Equations 2 and 3, hole injection to a first emission layer is facilitated, and thus an emission region may be confined to the inside of the first emission layer or an interface between the first emission layer and the second emission layer.

In some exemplary embodiments, the second emission layer may satisfy Equations 4 and 5.

$$|LUMO(D2)-LUMO(EML2(H1))| \leq 0.3 \text{ eV} \quad \text{<Equation 4>}$$

$$|LUMO(D2)-LUMO(EML2(H2))| \leq 0.3 \text{ eV} \quad \text{<Equation 5>}$$

In Equations 4 and 5,

LUMO(D2) is a lowest unoccupied molecular orbital (LUMO) energy level (eV) of the second dopant, LUMO (EML2(H1)) is a LUMO energy level (eV) of a first host included in the second emission layer, and LUMO(EML2 (H2)) is a LUMO energy level (eV) of a second host included in the second emission layer.

Each of LUMO(D2), LUMO(EML2(H1)), and LUMO (EML2(H2)) may be evaluated by using a DFT method of a Gaussian program structure-optimized at a degree of B3LYP/6-31G(d,p).

For example, the second dopant may have a shallower LUMO energy level than a first host included in the second emission layer and a second host included in the second emission layer.

In an organic light-emitting device satisfying Equations 4 and 5, electron injection to a second emission layer is facilitated, and thus an emission region may be confined to the inside of the second emission layer and an interface between the first emission layer and the second emission layer.

In some exemplary embodiments, the first emission layer of the organic light-emitting device may satisfy Equation 6, and a concentration of the first dopant in the first emission layer may increase from one surface of the first emission layer to the other surface facing the one surface. For example, a concentration of the first dopant may increase from one surface adjacent to a first electrode of the first emission layer to the other surface facing the one surface. Alternatively, a concentration of the first dopant may increase from one surface adjacent to a second electrode of the first emission layer to the other surface facing the one surface.

$$|HOMO(EML1(H1))|-|HOMO(D1)| \leq \text{about } 0.3 \text{ eV} \quad \text{<Equation 6>}$$

In other words, a HOMO energy level of the first dopant is about 0.3 eV or less than a HOMO energy level of the first host in the first emission layer.

When an organic light-emitting device satisfies Equation 6, the first dopant may have a hole trapping characteristic. In this regard, when a first dopant in the first emission layer has a concentration gradient, since hole injection and hole transport characteristics in the first emission layer may be adjusted, a charge balance in the first emission layer may be optimized.

In some exemplary embodiments, the second emission layer of the organic light-emitting device may satisfy Equation 7, and a concentration of the second dopant in the second emission layer may increase from one surface of the second emission layer to the other surface facing the one surface. For example, a concentration of the second dopant may increase from one surface adjacent to a first electrode of the second emission layer to the other surface facing the one surface. Alternatively, a concentration of the second dopant may increase from one surface adjacent to a second electrode of the second emission layer to the other surface facing the one surface.

$$|LUMO(EML2(H2)|-|LUMO(D2)| \leq \text{about } 0.4 \text{ eV} \quad \text{<Equation 7>}$$

In other words, a LUMO energy level of the second dopant is about 0.4 eV or less than a LUMO energy level of the second host in the second emission layer.

When an organic light-emitting device satisfies Equation 7, the second dopant may have an electron trapping characteristic. In this regard, when a second dopant in the second emission layer has a concentration gradient, since electron injection and electron transport characteristics in the second emission layer may be adjusted, a charge balance in the second emission layer may be optimized.

Weight ratios of the first host to the second host may each independently be about 10:90 to about 90:10 in the first emission layer and the second emission layer.

An amount of the first dopant in the first emission layer may be about 0.01 parts by weight to about 30 parts by weight based on 100 parts by weight of the first emission layer, for example, may be about 1 parts by weight to about 20 parts by weight or about 5 parts by weight to about 15 parts by weight, but the exemplary embodiments are not limited thereto.

An amount of the second dopant in the second emission layer may be about 0.01 parts by weight to about 30 parts by weight based on 100 parts by weight of the second emission layer, for example, may be about 1 parts by weight to about 20 parts by weight or about 5 parts by weight to about 15 parts by weight, but the exemplary embodiments are not limited thereto.

Thicknesses of the first auxiliary layer, the second auxiliary layer, and the third auxiliary layer may each independently be in a range of about 10 Å to about 500 Å, for example, about 30 Å to about 100 Å, but the exemplary embodiments are not limited thereto.

In some exemplary embodiments, the first electrode is an anode, the second electrode is a cathode, and the organic layer further includes a hole transport region disposed between the first electrode and the first emission layer or the first auxiliary layer and/or an electron transport region disposed between the second emission layer or the second auxiliary layer and the second electrode, wherein the hole transport region may include a hole injection layer, a hole transport layer, an emission auxiliary layer, an electron blocking layer, or any combination thereof, and the electron transport region may include a buffer layer, a hole blocking layer, an electron control layer, an electron transport layer, an electron injection layer, or any combination thereof, but the exemplary embodiments are not limited thereto. For example, when the organic light-emitting device includes a first auxiliary layer, the hole transport region may be disposed between the first electrode and the first auxiliary layer. When the organic light-emitting device includes a second auxiliary layer, the electron transport region may be disposed between the second auxiliary layer and the second electrode.

The electron transport region may include at least one layer selected from a buffer layer, a hole blocking layer, an electron control layer, an electron transport layer, and an electron injection layer.

In some exemplary embodiments, the electron transport region may include an electron transport layer, and the electron transport layer may include a first electron transport layer and a second electron transport layer.

Hereinafter, the structure of the organic light-emitting device 10 according to an embodiment and a method of manufacturing the organic light-emitting device 10 will be described in connection with FIG. 1.

First Electrode 110

Referring again to FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water resistance.

The first electrode 110 may be formed by depositing or sputtering a material for forming the first electrode 110 on the substrate. When the first electrode 110 is an anode, the material for a first electrode 110 may be selected from materials with a high work function to facilitate hole injection.

The first electrode 110 may be a reflective electrode, a semi-transmissive electrode, or a transmissive electrode. When the first electrode 110 is a transmissive electrode, a material for forming a first electrode may be selected from indium tin oxide (ITO), indium zinc oxide (IZO), tin oxide ($SnO_2$), zinc oxide (ZnO), and any combinations thereof, but the exemplary embodiments are not limited thereto. In one or more exemplary embodiments, when the first electrode 110 is a semi-transmissive electrode or a reflectable electrode, a material for forming a first electrode may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but the exemplary embodiments are not limited thereto.

The first electrode 110 may have a single-layered structure, or a multi-layered structure including two or more layers. For example, the first electrode 110 may have a three-layered structure of ITO/Ag/ITO, but the structure of the first electrode 110 is not limited thereto.

Organic Layer 150

The organic layer 150 may be disposed on the first electrode 110. The organic layer 150 may include a first emission layer EML1, a second emission layer EML2, and a first auxiliary layer AXL1.

The organic layer 150 may further include a hole transport region between the first electrode 110 and the first auxiliary layer AXL1 and an electron transport region between the second emission layer EML2 and the second electrode 190.

Hole Transport Region in Organic Layer 150

The hole transport region may have i) a single-layered structure including a single layer including a single material, ii) a single-layered structure including a single layer including a plurality of different materials, or iii) a multi-layered structure having a plurality of layers including a plurality of different materials.

The hole transport region may include at least one layer selected from a hole injection layer, a hole transport layer, an emission auxiliary layer, and an electron blocking layer.

For example, the hole transport region may have a single-layered structure including a single layer including a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, wherein for each structure, constituting layers are sequentially stacked from the first electrode 110 in this stated order, but the structure of the hole transport region is not limited thereto.

The hole transport region may include at least one compound selected from m-4,4',4"-tris[phenyl(m-tolyl)amino]triphenylamine (MTDATA), 1-N,1-N-bis[4-(diphenylamino)phenyl]-4-N,4-N-diphenylbenzene-1,4-diamine (TDATA,) 4,4',4"-tris[2-naphthyl(phenyl)amino]triphenylamine (2-TNATA), N,N'-di(naphtalene-1-yl)-N,N'-diphenyl-benzidine (NPB or NPD), N4,N4'-di(naphthalen-2-yl)-N4,N4'-diphenyl-[1,1'-biphenyl]-4,4'-diamine (β-NPB), N,N'-bis(3-methylphenyl)-N,N'-diphenyl-[1,1-biphenyl]-4,4'-diamine (TPD), 4(N,N'-bis(3-methylphenyl)-N,N'-diphenyl-9,9-spirobifluorene-2,7-diamine (spiro-TPD), 2,7-bis[N-(1-naphthyl)anilino]-9,9'-spirobi[9H-fluorene] (spiro-NPB), 2,2'-dimethyl-N,N'-di-[(1-naphthyl)-N,N'-diphenyl]-1,1'-biphenyl-4,4'-diamine(methylated-NPB), 4,4'-cyclohexylidene bis[N,N-bis(4-methylphenyl) benzenamine] (TAPC), 4,4'-bis[N,N'-(3-tolyl)amino]-3,3'-dimethylbiphenyl (HMTPD), 4,4',4"-tris(N-carbazolyl) triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), a compound represented by Formula 201, and a compound represented by Formula 202:

m-MTDATA

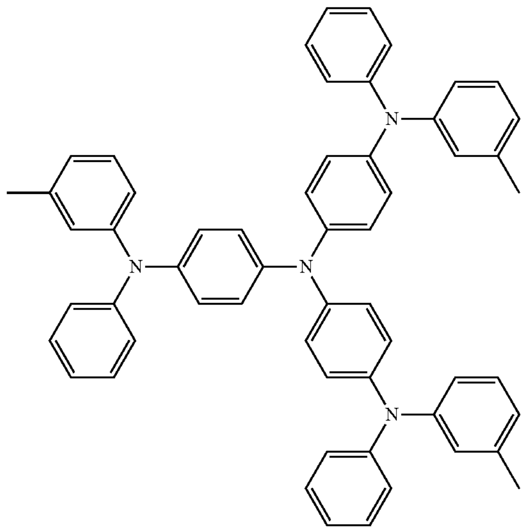

TDATA

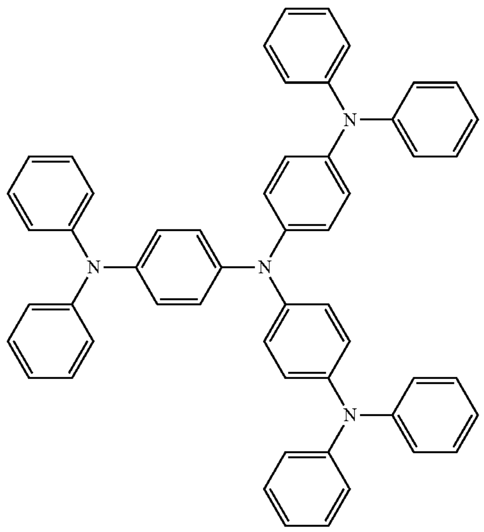

-continued
2-TNATA
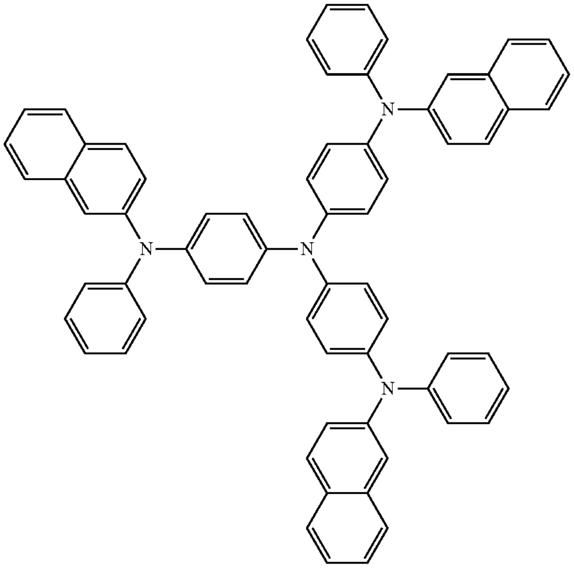
NPB
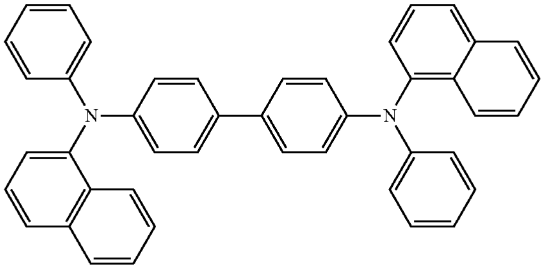
β-NPB
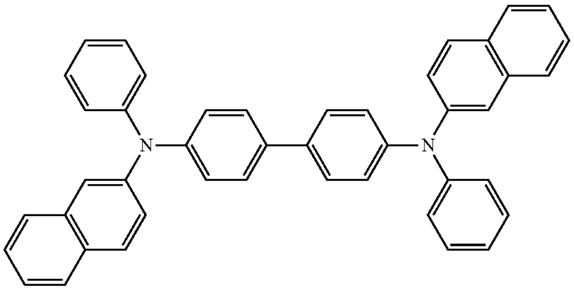
TPD
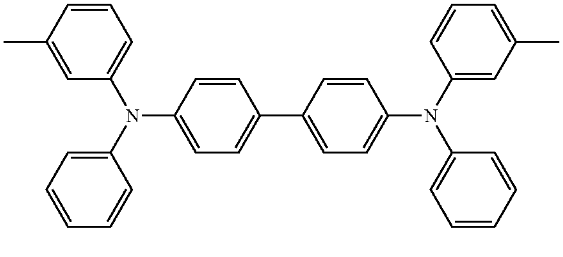
-continued
Spiro-TPD
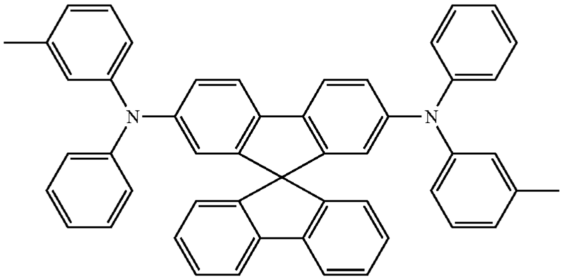
Spiro-NPB
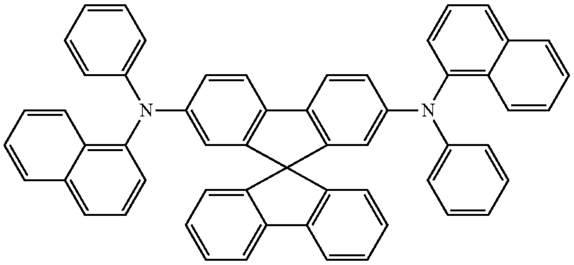
methylated NPB
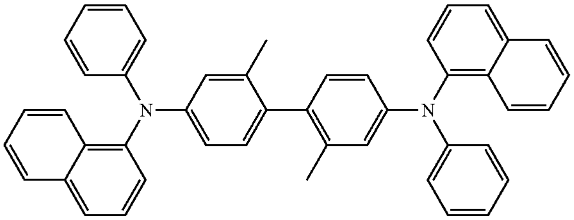
TAPC
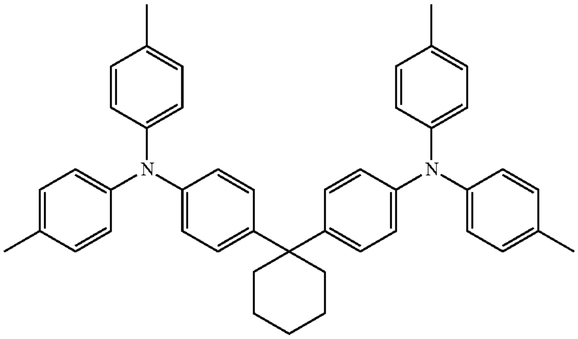
HMTPD
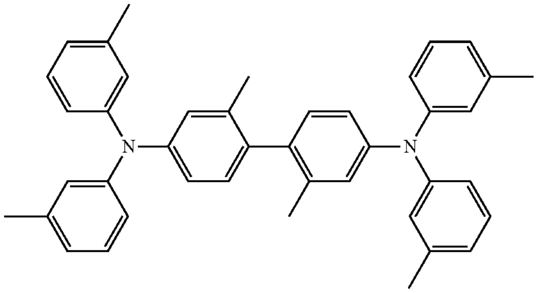
<Formula 201>
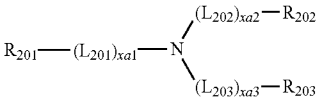

-continued

<Formula 202>

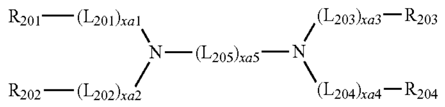

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted C1-$C_{60}$ heteroarylene group, a substituted or unsubstituted divalent non-aromatic condensed polycyclic group, and a substituted or unsubstituted divalent non-aromatic condensed heteropolycyclic group, $L_{205}$ may be selected from *—O—*', *—S—*', *—N($Q_{201}$)—*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, a substituted or unsubstituted C1-C10 heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some exemplary embodiments, in Formula 202, $R_{201}$ and $R_{202}$ may optionally be linked together via a single bond, a dimethyl-methylene group, or a diphenyl-methylene group, and $R_{203}$ and $R_{204}$ may optionally be linked together via a single bond, a dimethyl-methylene group, or a diphenyl-methylene group.

In some exemplary embodiments, in Formulae 201 and 202, $L_{201}$ to $L_{205}$ may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$) and —N($Q_{31}$)($Q_{32}$), wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In one or more exemplary embodiments, xa1 to xa4 may each independently be 0, 1, or 2.

In one or more exemplary embodiments, xa5 may be 1, 2, 3, or 4.

In one or more exemplary embodiments, $R_{201}$ to $R_{204}$ and $Q_{201}$ may each independently be selected from: a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, $—Si(Q_{31})(Q_{32})(Q_{33})$ and $—N(Q_{31})(Q_{32})$, wherein $Q_{31}$ to $Q_{33}$ are the same as described above.

In one or more exemplary embodiments, at least one selected from $R_{201}$ to $R_{203}$ in Formula 201 may each independently be selected from:

a fluorenyl group, a spiro-bifluorenyl group, a carbazolyl group, a dibenzofuranyl group, and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a C1-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a C1-C10 alkyl group, a phenyl group substituted with —F, a naphthyl group, a fluorenyl group, a spiro-bifluorenyl group, a carbazolyl group, a dibenzofuranyl group, and a dibenzothiophenyl group, but the exemplary embodiments are not limited thereto.

In one or more exemplary embodiments, in Formula 202, i) $R_{201}$ and $R_{202}$ may be linked via a single bond, and/or ii) $R_{203}$ and $R_{204}$ may be linked together via a single bond.

In one or more exemplary embodiments, $R_{201}$ to $R_{204}$ in Formula 202 may be selected from:

a carbazolyl group; and a carbazolyl group substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the exemplary embodiments are not limited thereto.

The compound represented by Formula 201 may be represented by Formula 201-1 below:

<Formula 201-1>

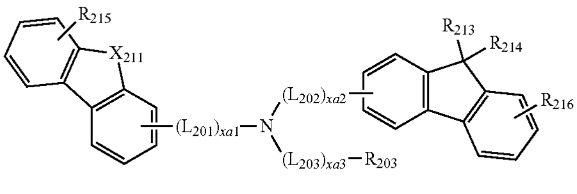

In some exemplary embodiments, the compound represented by Formula 201 may be represented by Formula 201-2 below, but the exemplary embodiments are not limited thereto:

<Formula 201-2>

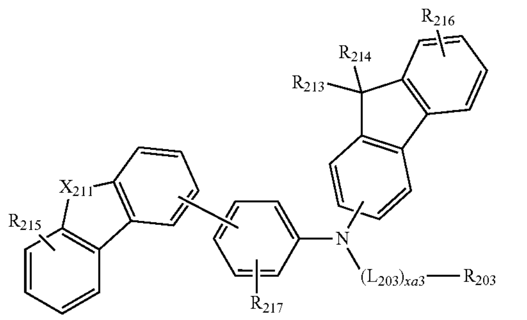

In one or more exemplary embodiments, the compound represented by Formula 201 may be represented by Formula 201-2(1) below, but the exemplary embodiments are not limited thereto:

<Formula 201-2(1)>

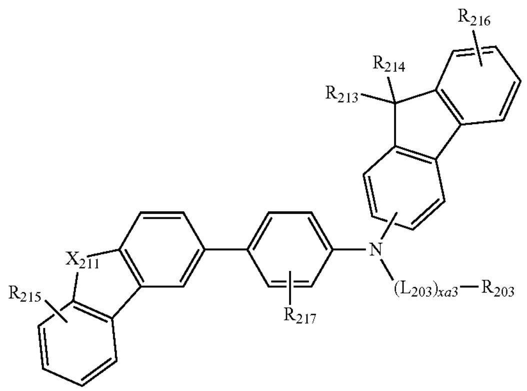

The compound represented by Formula 201 may be represented by Formula 201A:

<Formula 201A>

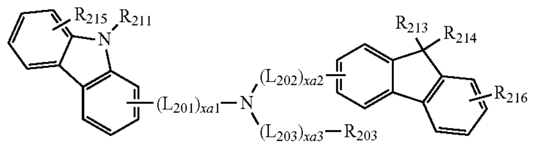

In some exemplary embodiments, the compound represented by Formula 201 may be represented by Formula 201A(1) below, but the exemplary embodiments are not limited thereto:

<Formula 201A(1)>

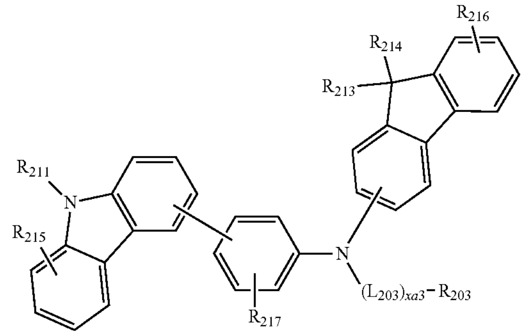

In some exemplary embodiments, the compound represented by Formula 201 may be represented by Formula 201A-1 below, but the exemplary embodiments are not limited thereto:

<Formula 201A-1>

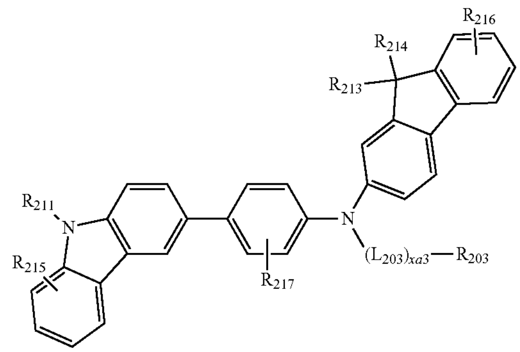

In one or more exemplary embodiments, the compound represented by Formula 202 may be represented by Formula 202-1:

<Formula 202-1>

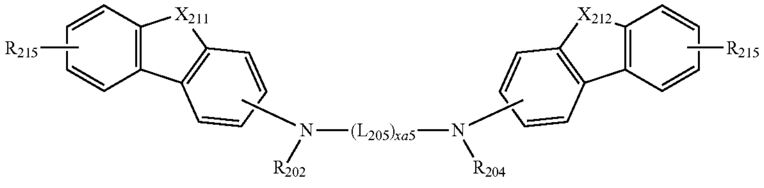

In one or more exemplary embodiments, the compound represented by Formula 202 may be represented by Formula 202-1(1) below:

<Formula 202-1(1)>

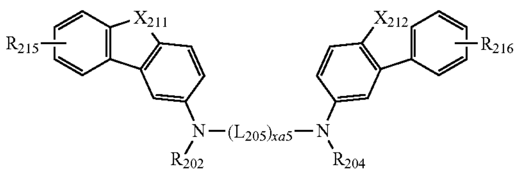

In some exemplary embodiments, the compound represented by Formula 202 may be represented by Formula 202A:

a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

<Formula 202A>

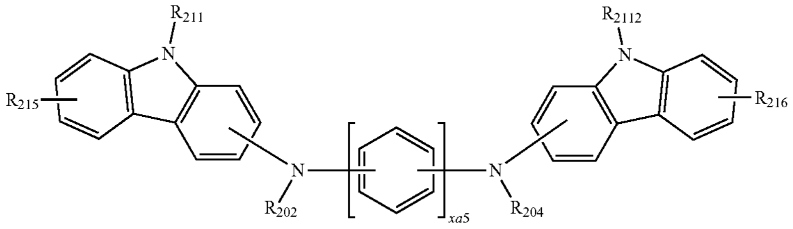

In one or more exemplary embodiments, the compound represented by Formula 202 may be represented by Formula 202A-1:

<Formula 202A-1>

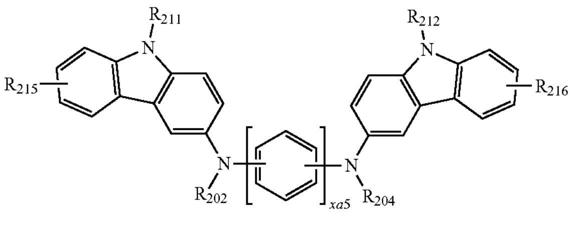

In Formulae 201-1, 201-2, 201-2(1), 201A, 201A(1), 201A-1, 202-1, 202-1(1), 202A, and 202A-1, $L_{201}$ to $L_{203}$, xa1 to xa3, xa5, and $R_{202}$ to $R_{204}$ are the same as described above, $L_{205}$ may be selected from a phenylene group, and a fluorenylene group, $X_{211}$ may be selected from O, S, and $N(R_{211})$, $X_{212}$ may be selected from O, S, and $N(R_{212})$, $R_{211}$ and $R_{212}$ may be the same as defined in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, The hole transport region may include at least one compound selected from Compounds HT1 to HT48 below, but the exemplary embodiments are not limited thereto:

HT1

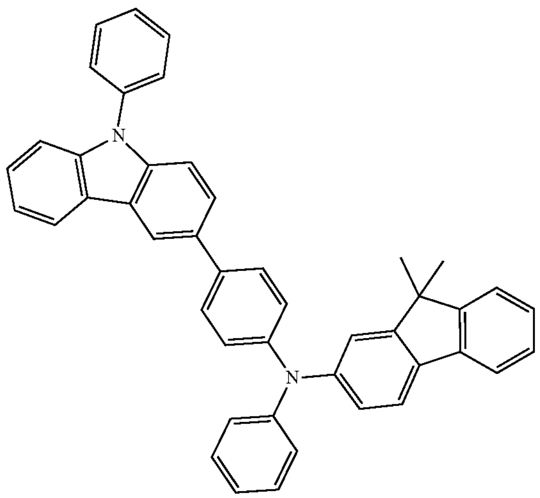

-continued
HT2
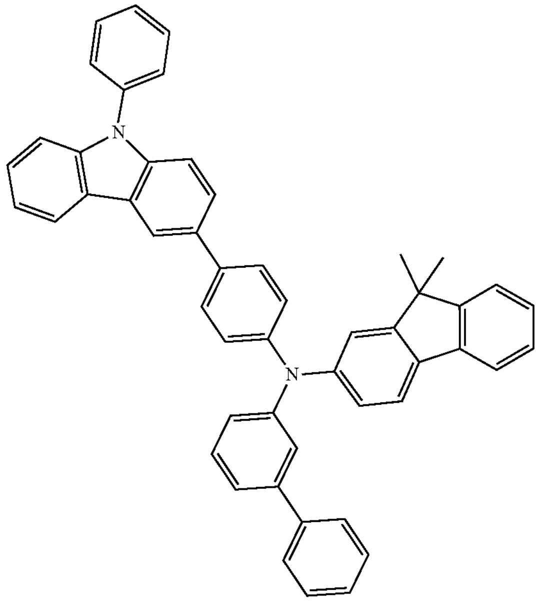
HT3
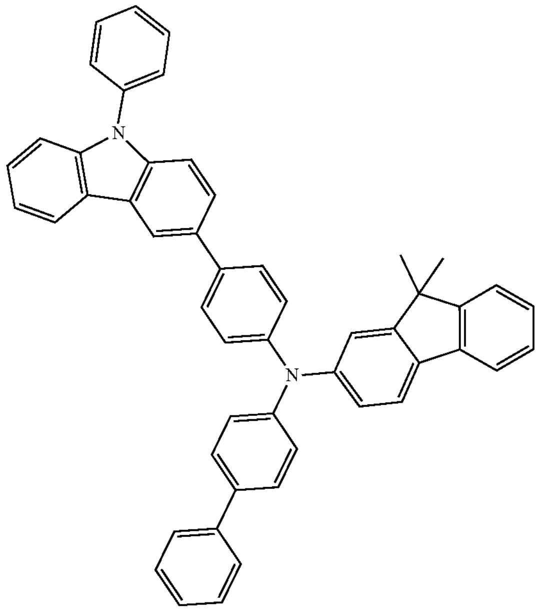
-continued
HT4
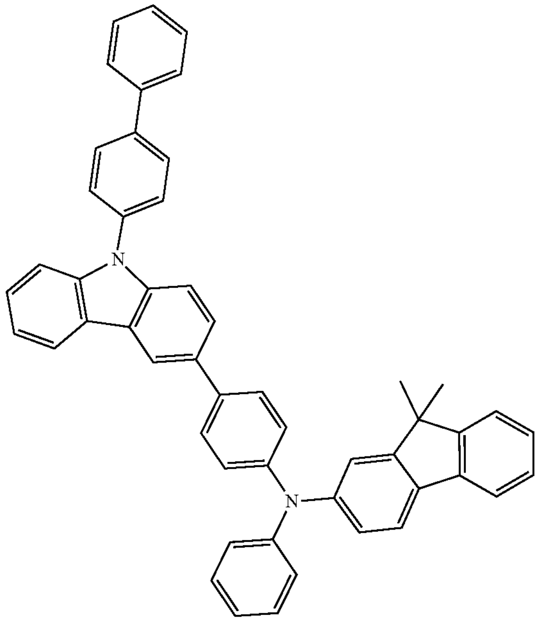
HT5
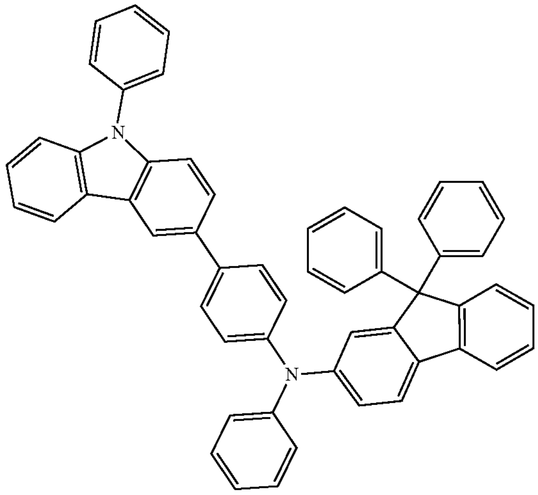

-continued
HT6
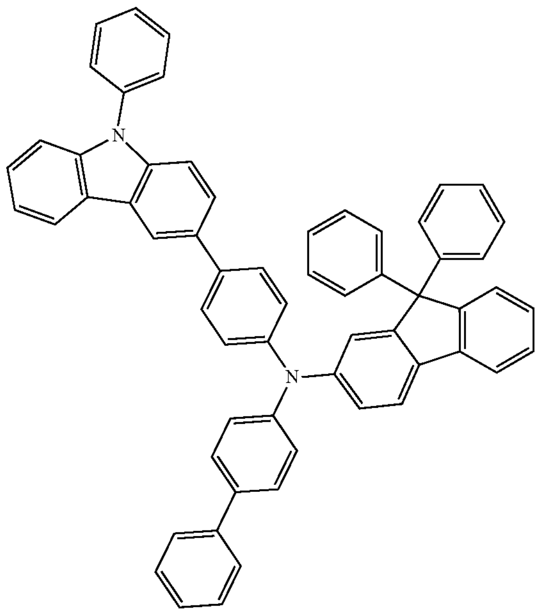
HT7
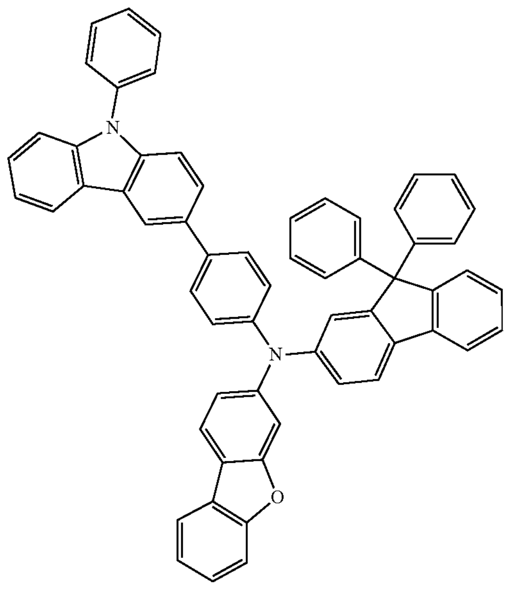
-continued
HT8
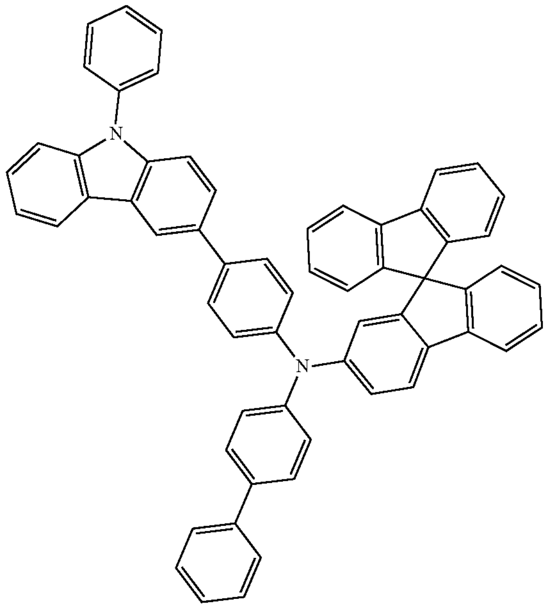
HT9
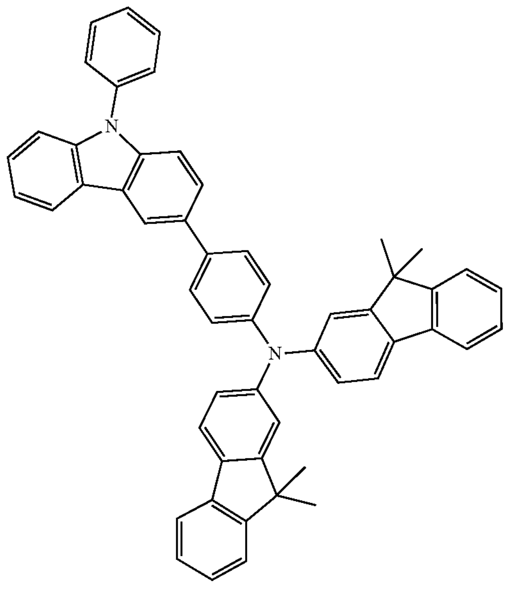

-continued
HT10
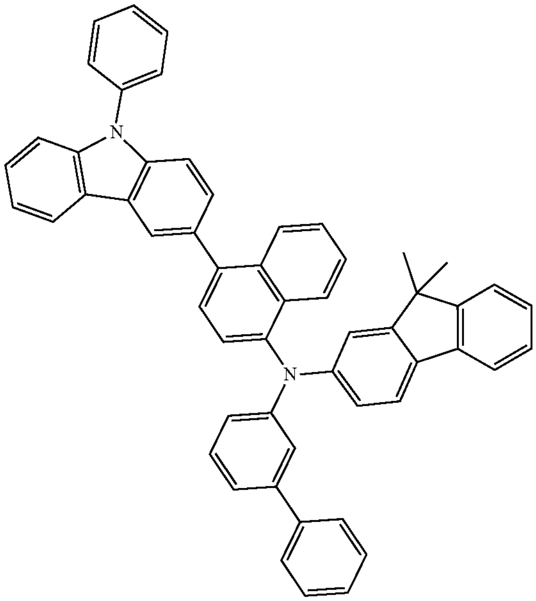
HT11
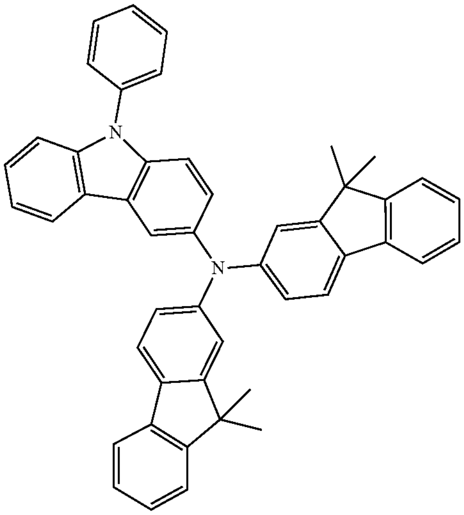
HT12
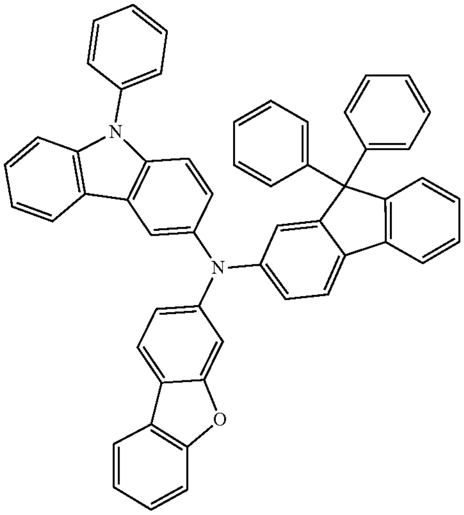
-continued
HT13
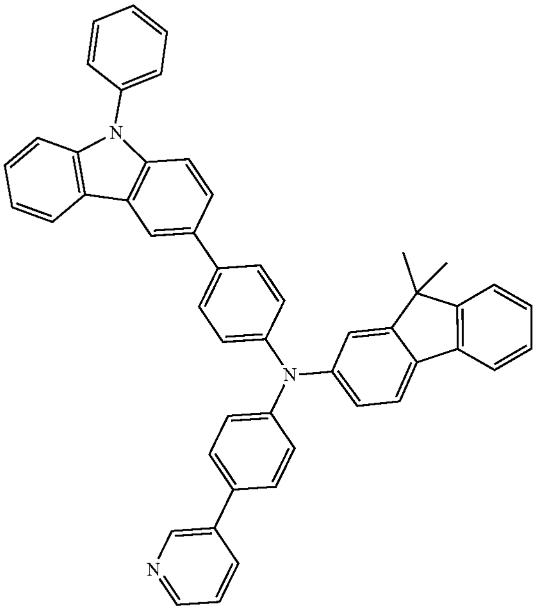
HT14
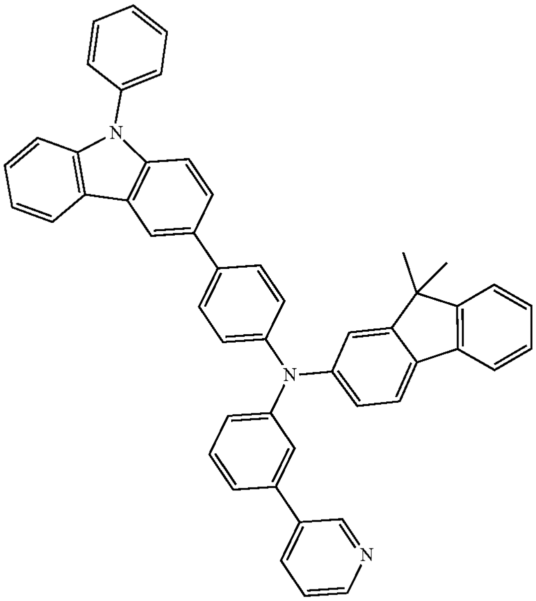

-continued
HT15
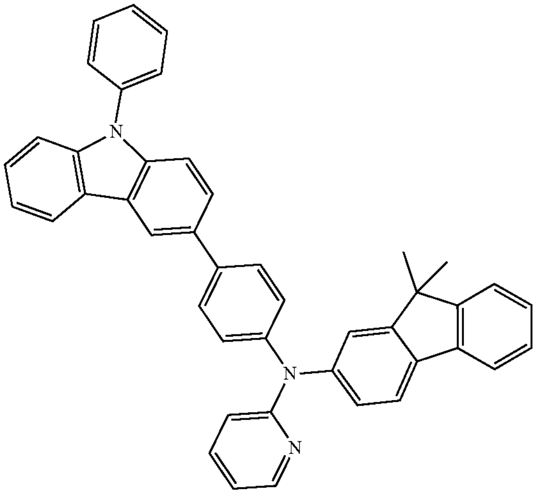
HT16
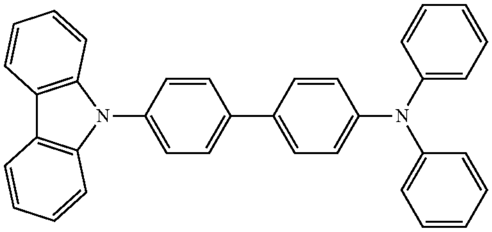
HT17
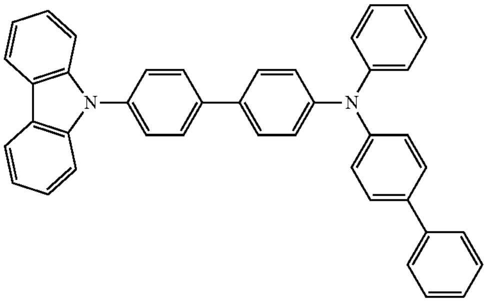
HT18
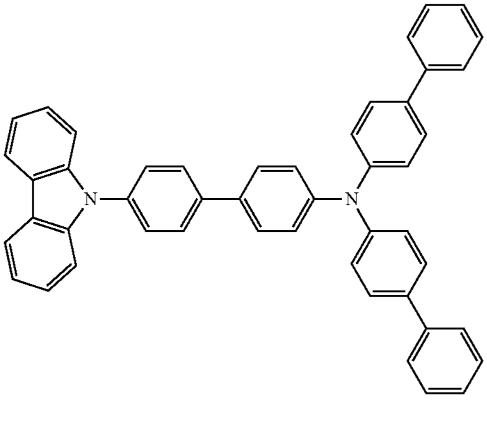
-continued
HT19
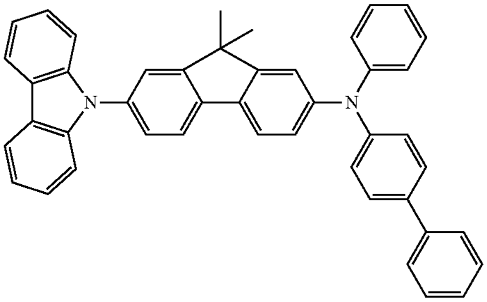
HT20
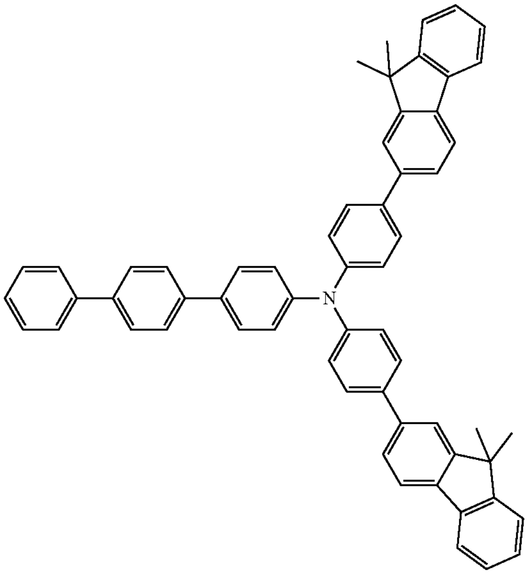
HT21
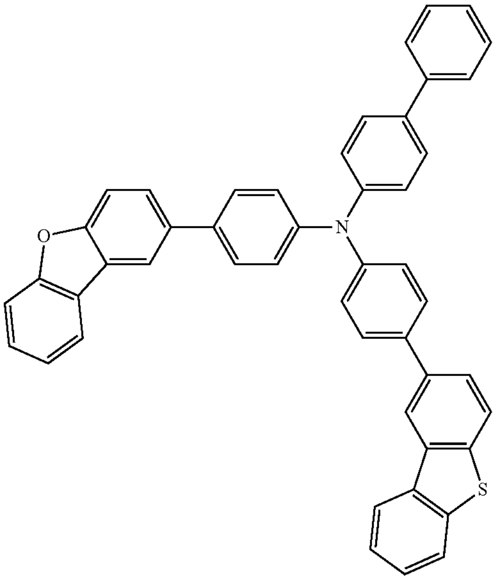

-continued
HT22
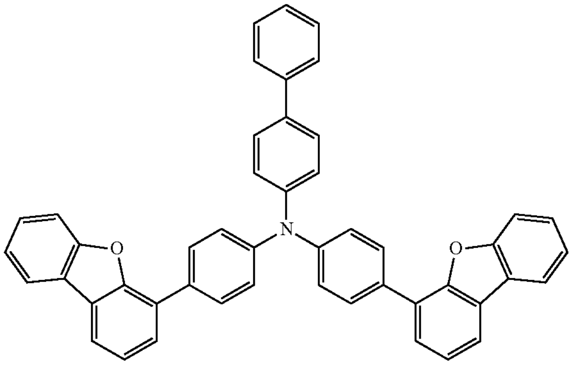
HT23
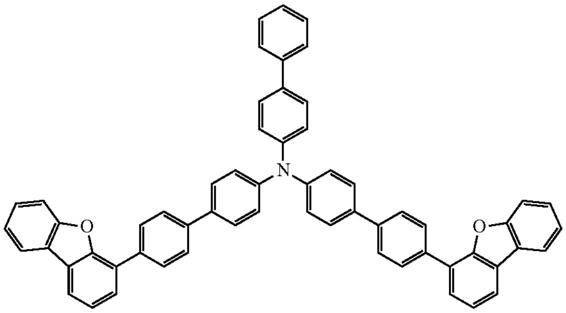
HT24
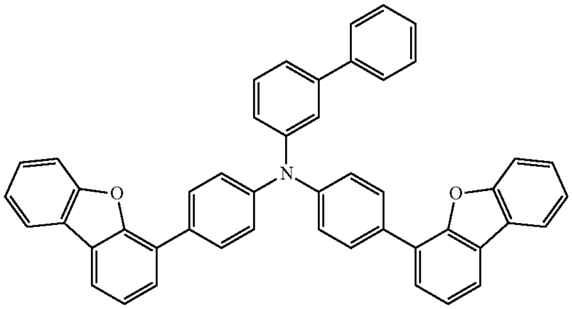
HT25
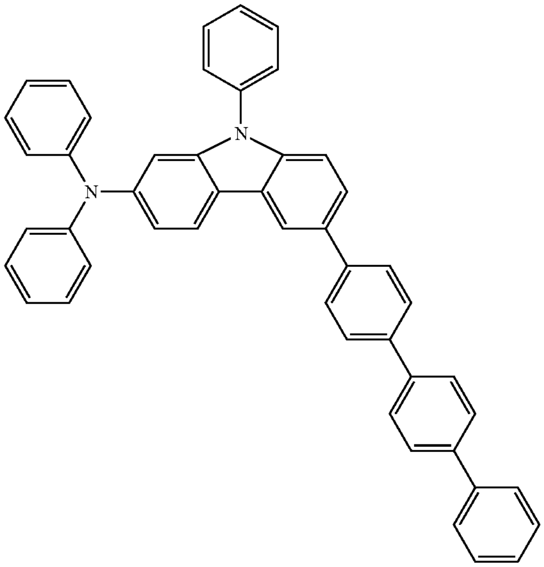
-continued
HT26
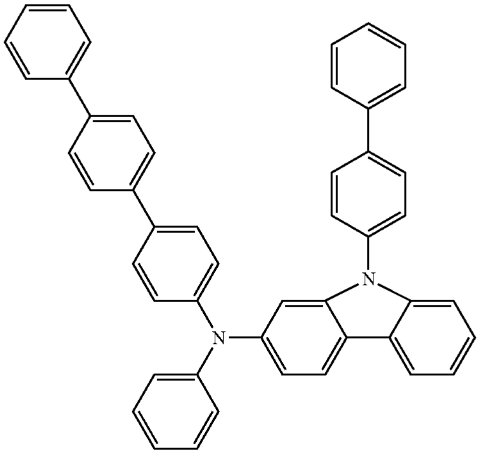
HT27
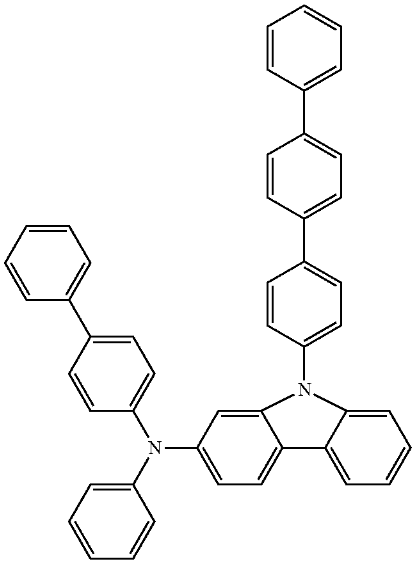
HT28
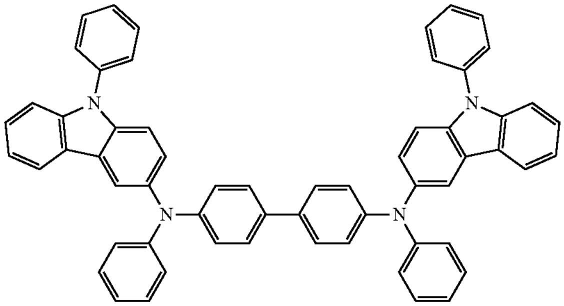

-continued
HT29
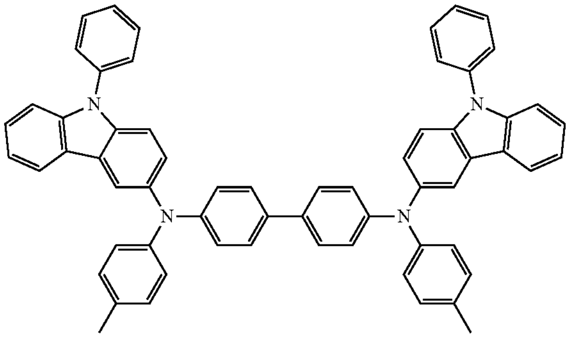
HT30
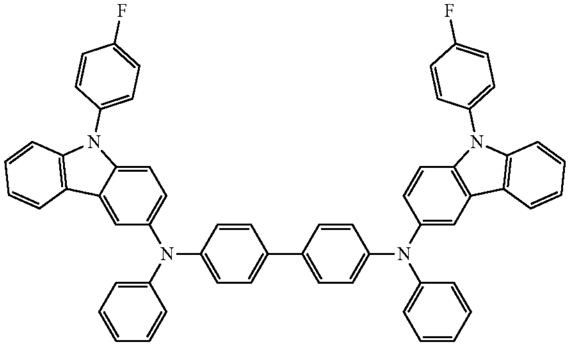
HT31
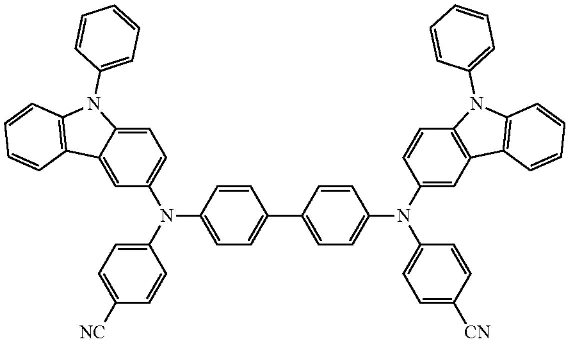
HT32
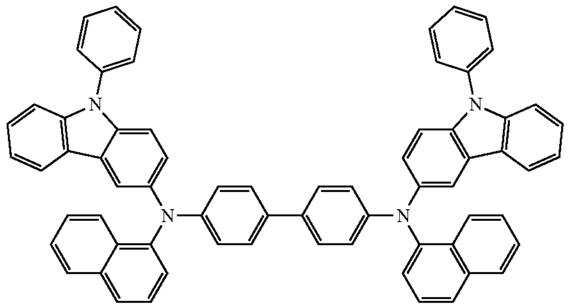
-continued
HT33
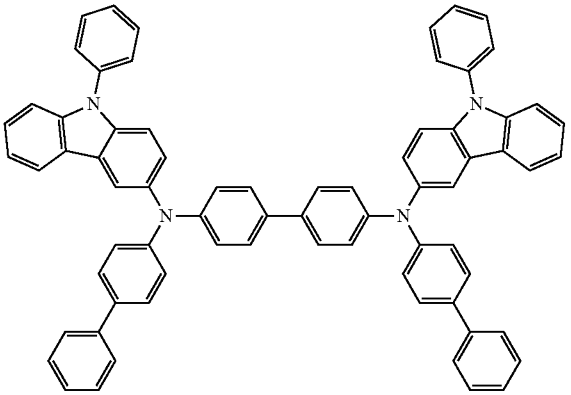
HT34
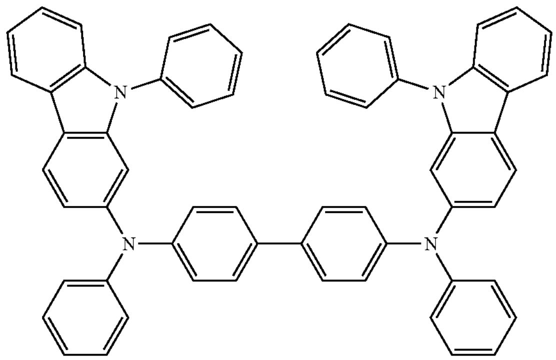
HT35
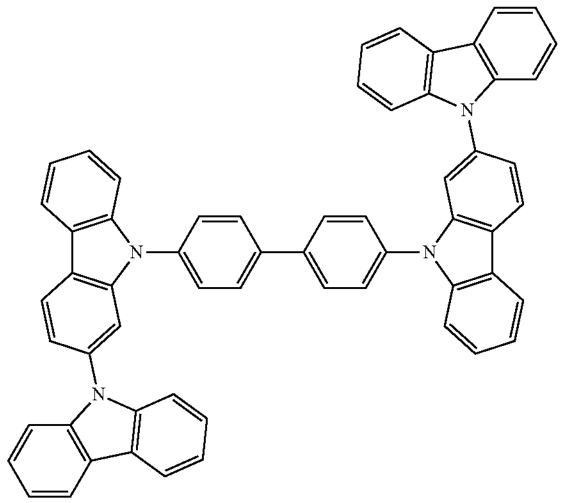

-continued
HT36
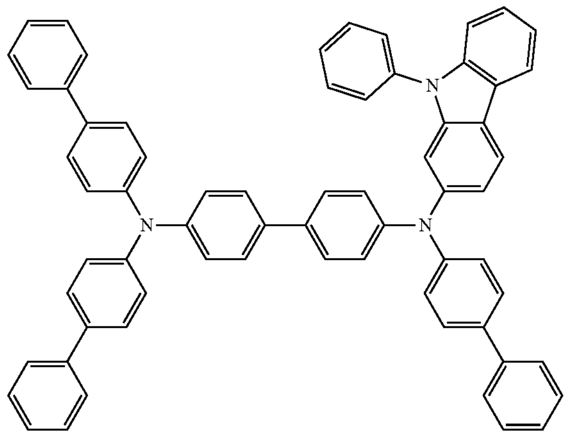
HT37
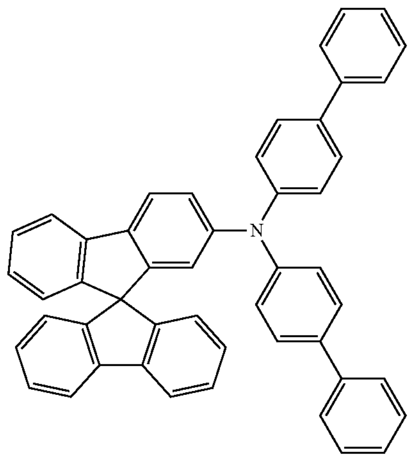
HT38
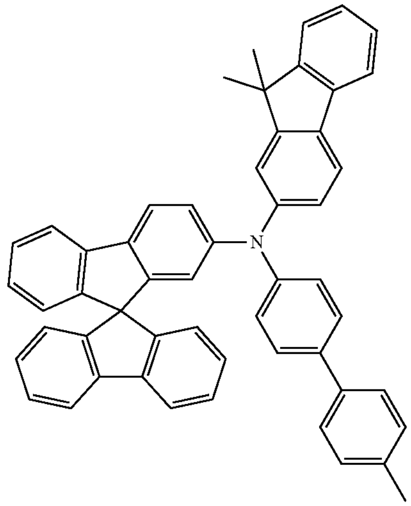
-continued
HT39
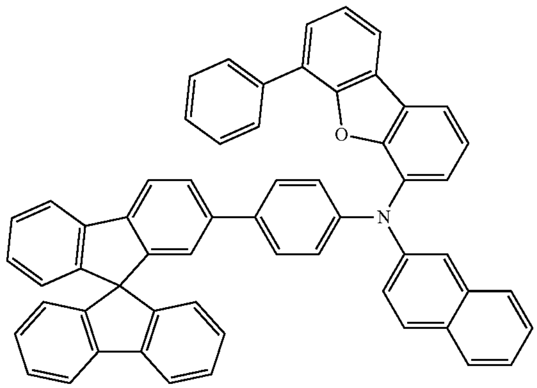
HT40
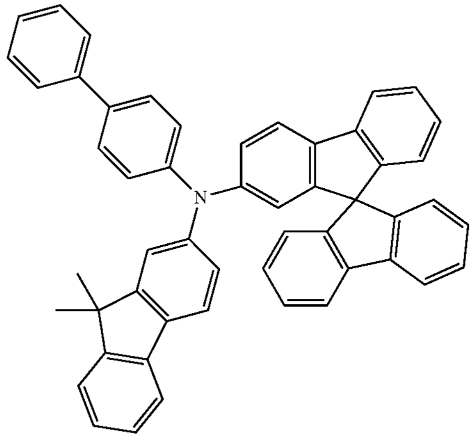
HT41
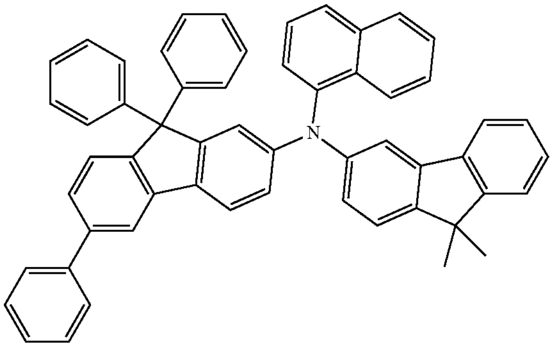
HT42
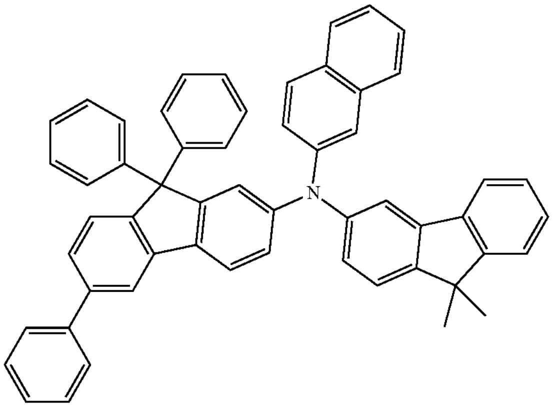

-continued
HT43
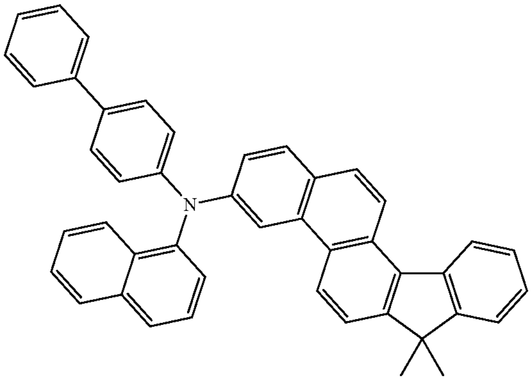
HT44
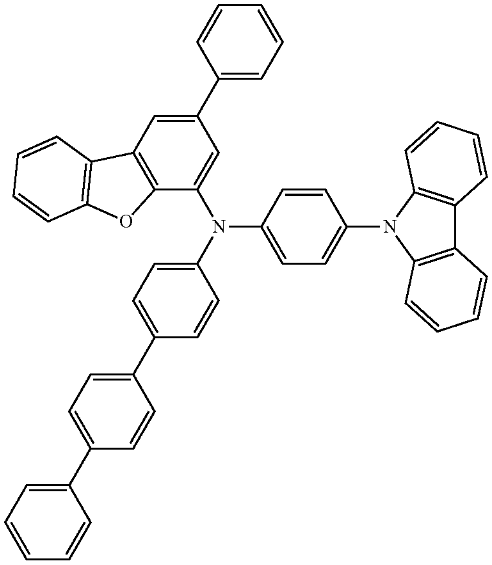
HT45
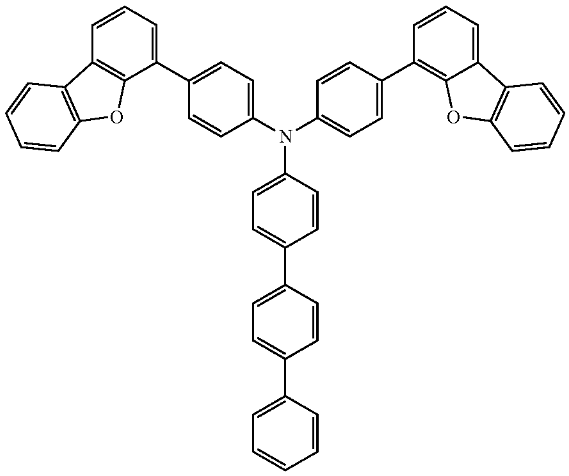
-continued
HT46
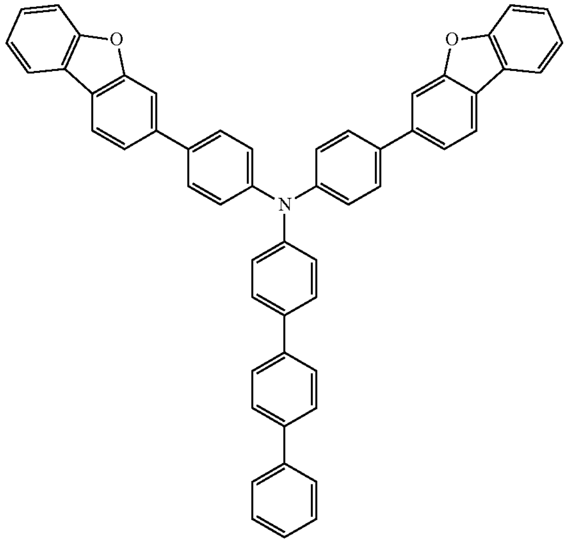
HT47
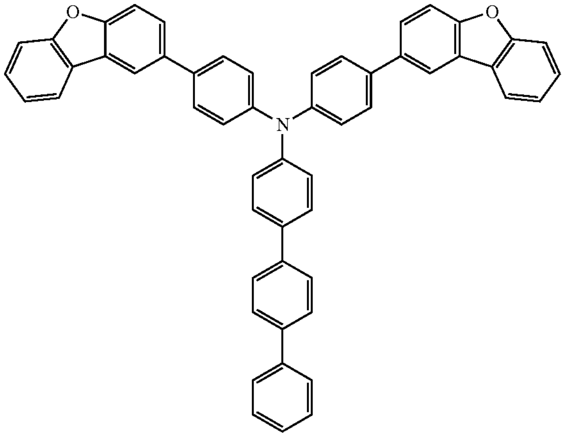
HT48
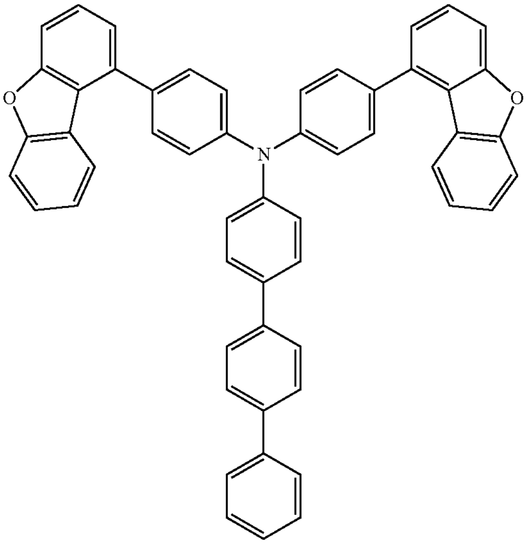
The thickness of the hole transport region may be from about 100 Å to about 10,000 Å, for example, about 100 Å to about 1,000 Å. When the hole transport region includes at least one of a hole injection layer and a hole transport layer, the thickness of the hole injection layer may be in a range of about 100 Å to about 9,000 Å, for example, about 100 Å to about 1,000 Å, and the thickness of the hole transport layer may be in a range of about 50 Å to about 2,000 Å, for example about 100 Å to about 1,500 Å. When the thicknesses of the hole transport region, the hole injection layer, and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

p-Dopant

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant.

In some exemplary embodiments, a LUMO energy level of the p-dopant may be about −3.5 eV or less.

The p-dopant may include at least one selected from a quinone derivative, a metal oxide, and a cyano group-containing compound, but the exemplary embodiments are not limited thereto.

In some exemplary embodiments, the p-dopant may include:

a quinone derivative, such as tetracyanoquinodimethane (TCNQ) or 2,3,5,6-tetrafluoro-7,7,8,8-tetracyanoquinodimethane (F4-TCNQ);

a metal oxide, such as tungsten oxide and molybdenum oxide;

1,4,5,8,9,12-hexaazatriphenylene-hexacarbonitrile (HAT-CN); and a compound represented by Formula 221, but the exemplary embodiments are not limited thereto:

<HAT-CN>

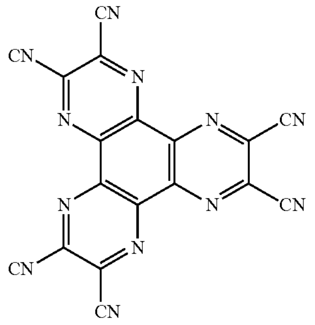

<F4-TCNQ>

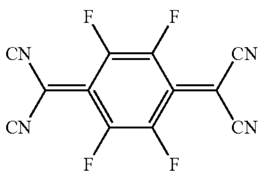

-continued

<Formula 221>

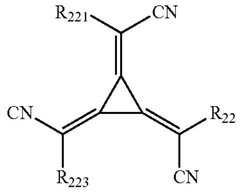

In Formula 221, $R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and at least one selected from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

Emission Layers EML1 and EML2

The first and second emission layers EML1 and EML2 of the organic light-emitting device 10 are the same as described above.

The thicknesses the first and second emission layers EML1 and EML2 may each independently be in the range of about 100 Å to about 1000 Å, for example, about 150 Å to about 600 Å. When the thicknesses of the emission layers are within these ranges, excellent light-emission characteristics may be obtained without a substantial increase in driving voltage.

The first emission layer EML1 may include a first dopant as described above, and the second emission layer EML2 may include a second dopant as described above. The first and second emission layers EML1 and EML2 may optionally further include a fluorescent dopant.

The fluorescent dopant may include an arylamine compound or a styrylamine compound.

Electron Transport Region in Organic Layer 150

The electron transport region may have i) a single-layered structure including a single layer including a single material, ii) a single-layered structure including a single layer including a plurality of different materials, or iii) a multi-layered structure having a plurality of layers including a plurality of different materials.

The electron transport region may include at least one selected from a buffer layer, a hole blocking layer, an electron control layer, an electron transport layer, and an electron injection layer, but the exemplary embodiments are not limited thereto.

For example, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, wherein for each structure, constituting layers are sequentially stacked from an emission layer. However, the exemplary embodiments of the structure of the electron transport region are not limited thereto.

The electron transport region (for example, a buffer layer, a hole blocking layer, an electron control layer, or an electron transport layer in the electron transport region) may include a metal-free compound containing at least one 7 electron-deficient nitrogen-containing ring.

The "π electron-deficient nitrogen-containing ring" indicates a $C_1$-$C_{60}$ heterocyclic group having at least one *—N=*' moiety as a ring-forming moiety, as described above for the cyclic group. For example, the "π electron-deficient nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is fused with at least one $C_5$-$C_{60}$ carbocyclic group. Examples of the π electron-deficient nitrogen-containing ring include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, a thiadiazole, an imidazopyridine, an imidazopyrimidine, and an azacarbazole, but are not limited thereto.

For example, the electron transport region may include a compound represented by Formula 601:

$$[Ar_{601}]_{xe11}\text{-}[(L_{601})_{xe1}\text{-}R_{601}]_{xe21}$$ <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted C1-C10 heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $—Si(Q_{601})(Q_{602})(Q_{603})$, $—C(=O)(Q_{601})$, $—S(=O)_2(Q_{601})$, and $—P(=O)(Q_{601})(Q_{602})$, $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In some exemplary embodiments, at least one selected from $Ar_{601}$ in the number of xe11 and $R_{601}$ in the number of xe21 may include the π electron-deficient nitrogen-containing ring described above.

In some exemplary embodiments, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group; and a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an isobenzothiazole group, a benzoxazole group, an isobenzoxazole group, a triazole group, a tetrazole group, an oxadiazole group, a triazine group, a thiadiazole group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, $—Si(Q_{31})(Q_{32})(Q_{33})$, $—S(=O)_2(Q_{31})$, and $—P(=O)(Q_{31})(Q_{32})$, wherein $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is 2 or more, two or more $Ar_{601}$(s) may be linked together via a single bond.

In one or more exemplary embodiments, $Ar_{601}$ in Formula 601 may be an anthracene group.

In one or more exemplary embodiments, the compound represented by Formula 601 may be represented by Formula 601-1 below:

<Formula 601-1>

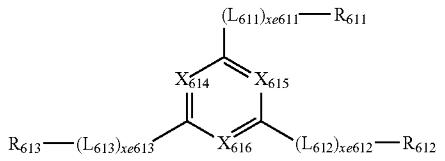

In Formula 601-1, $X_{614}$ may be N or $C(R_{614})$, $X_{615}$ may be N or $C(R_{615})$, $X_{616}$ may be N or $C(R_{616})$, at least one selected from $X_{614}$ to $X_{616}$ may be N, $L_{611}$ to $L_{613}$ may each independently be the same as described in connection with the $L_{601}$, xe611 to xe613 may each independently be the same as described in connection with xe1, $R_{614}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In some exemplary embodiments, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but the exemplary embodiments are not limited thereto.

In one or more exemplary embodiments, xe1 and xe611 to xe613 in Formulae 601 and 601-1 may each independently be 0, 1, or 2.

In one or more exemplary embodiments, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and $—S(=O)_2(Q_{601})$ and $—P(=O)(Q_{601})(Q_{602})$, wherein $Q_{601}$ and $Q_{602}$ are the same as described above.

The electron transport region may include at least one compound selected from Compounds ET1 to ET36, but the exemplary embodiments are not limited thereto:

ET1

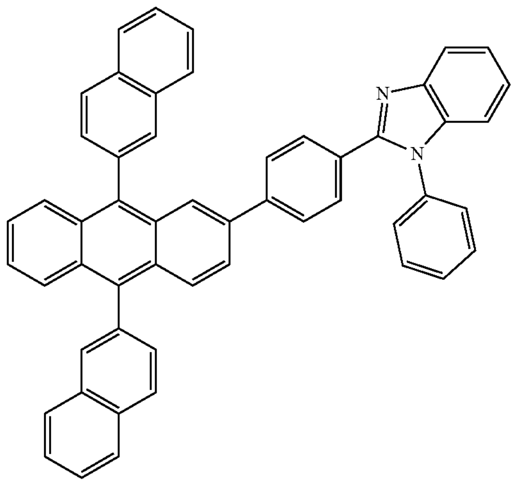

-continued
ET2
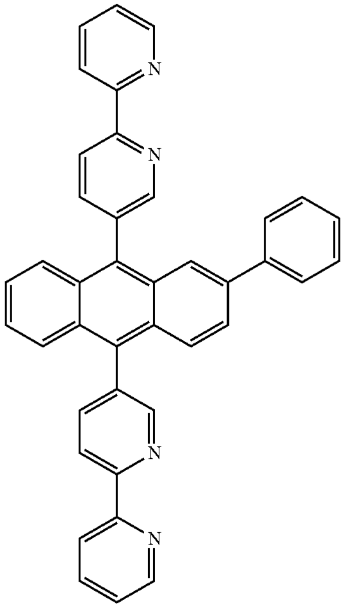
ET3
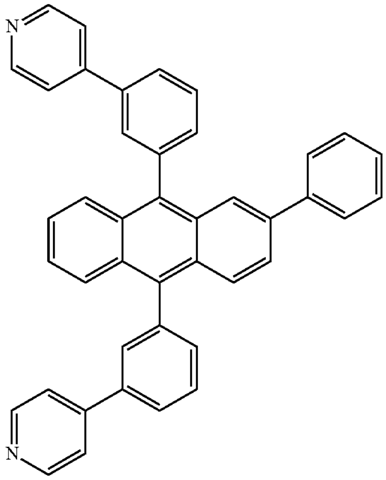
ET4
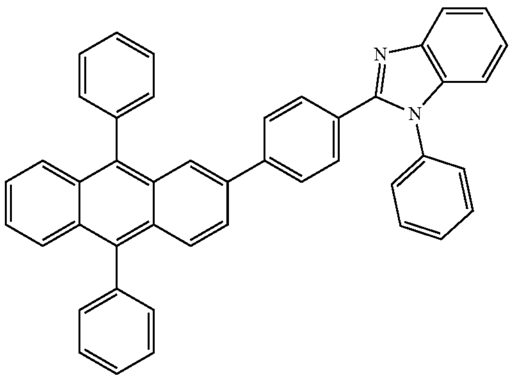
-continued
ET5
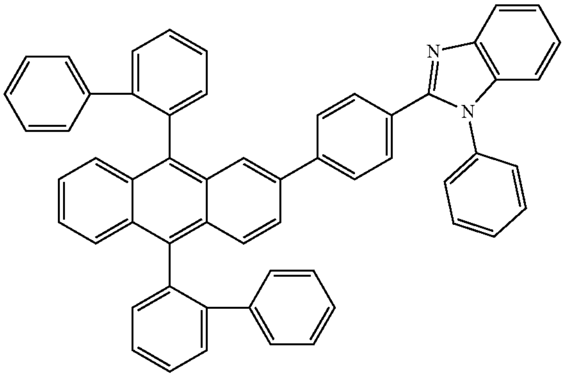
ET6
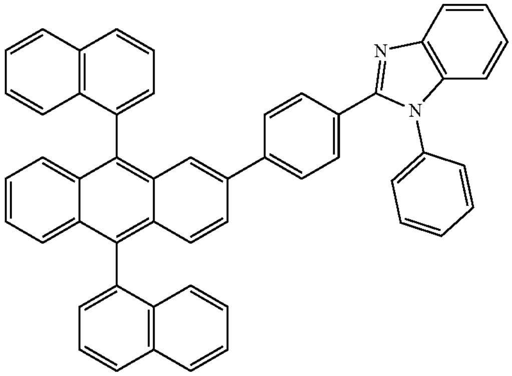
ET7
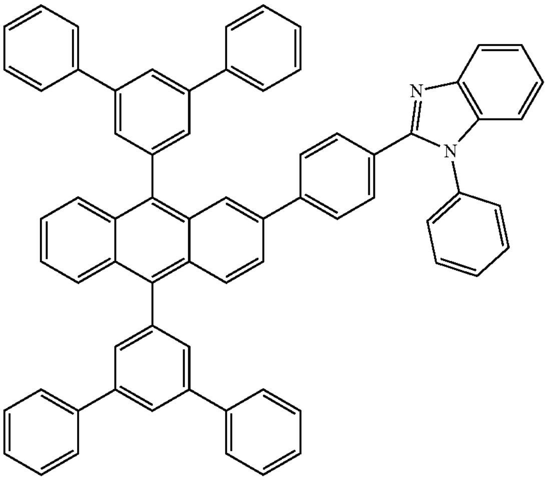

-continued
ET8
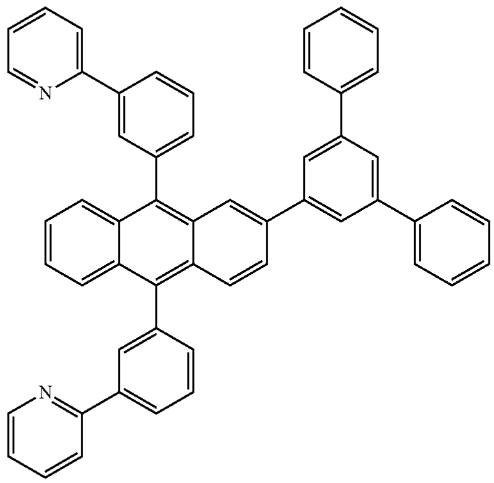
ET9
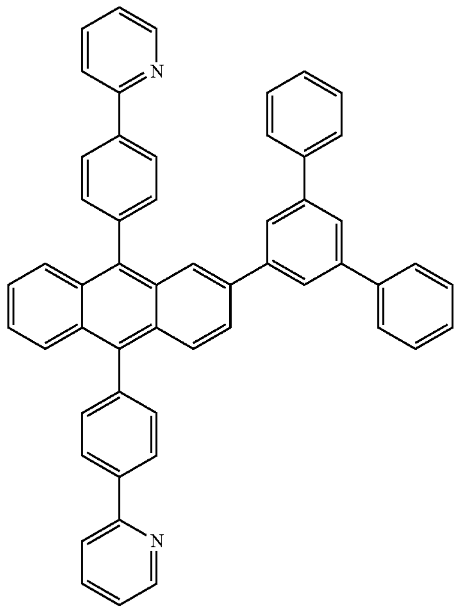
-continued
ET10
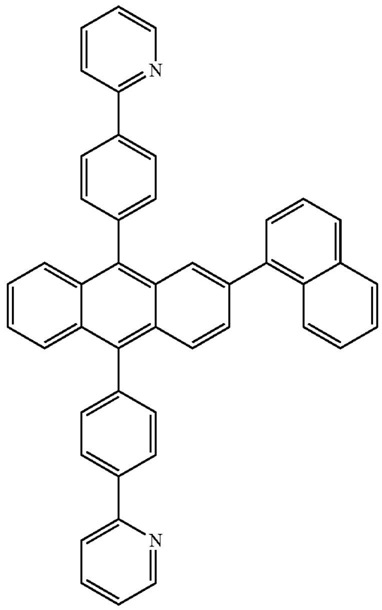
ET11
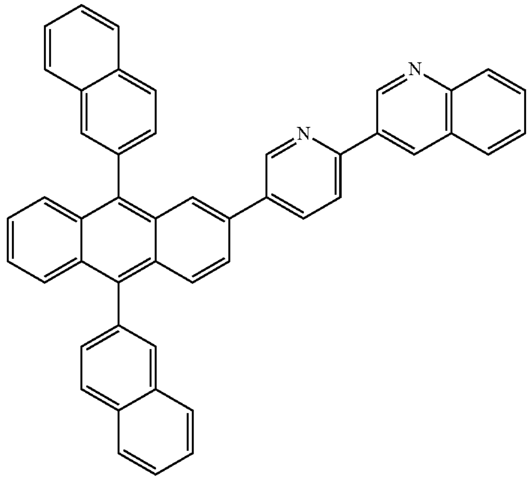
ET12
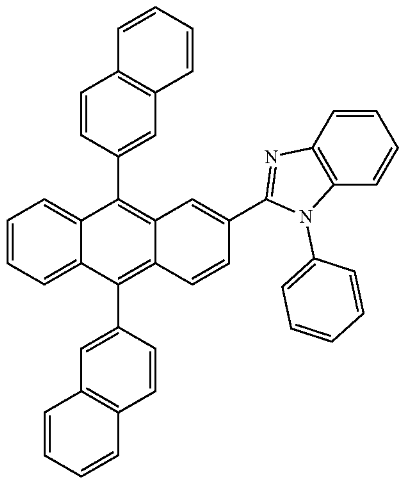

-continued
ET13
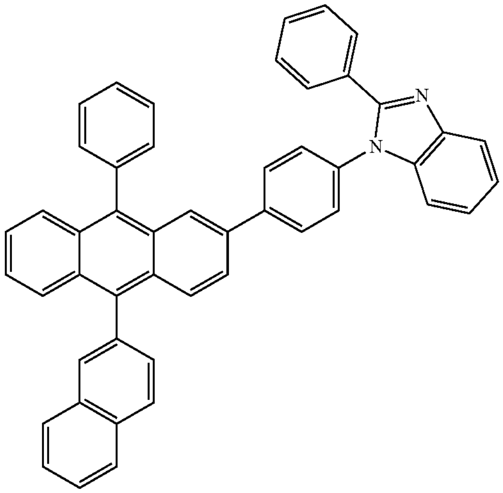
ET14
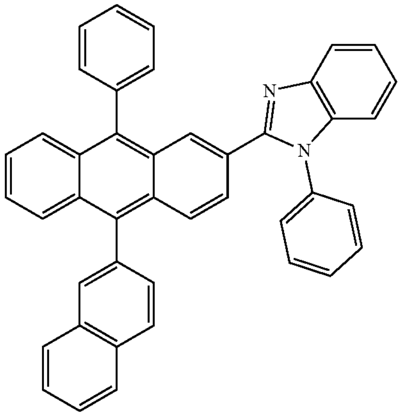
ET15
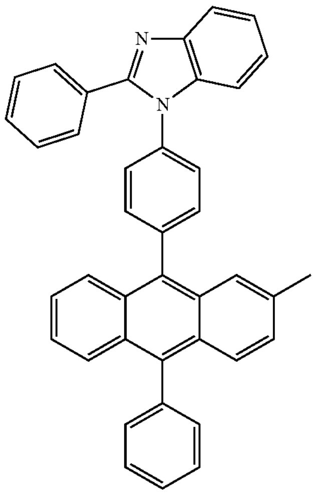
-continued
ET16
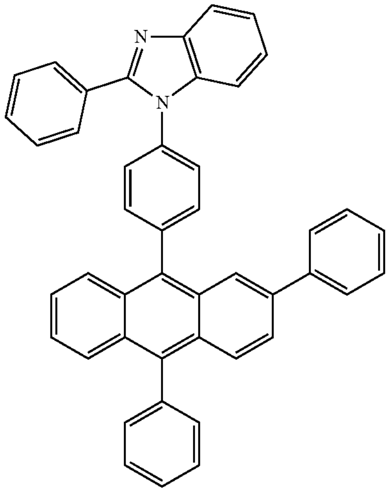
ET17
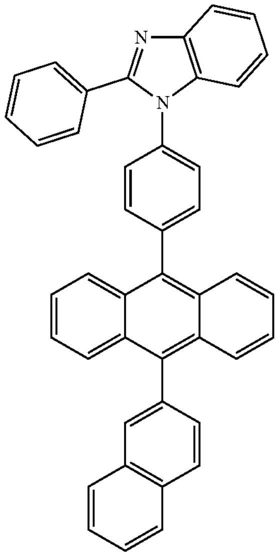
ET18
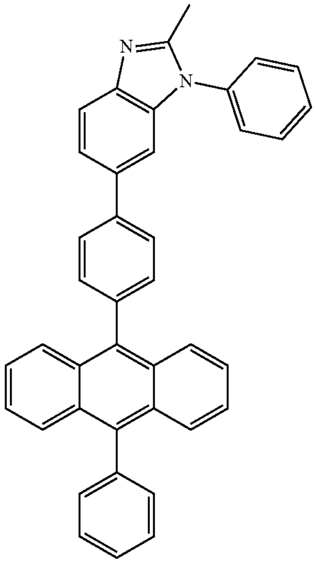

-continued
ET19
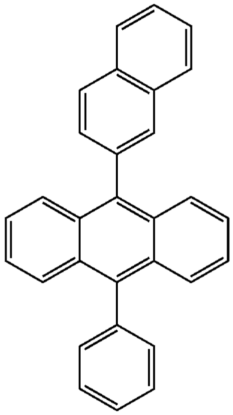
ET20
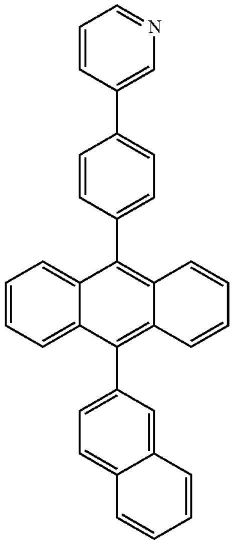
ET21
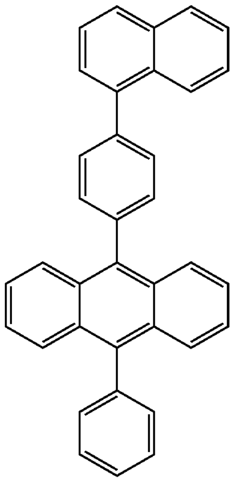
-continued
ET22
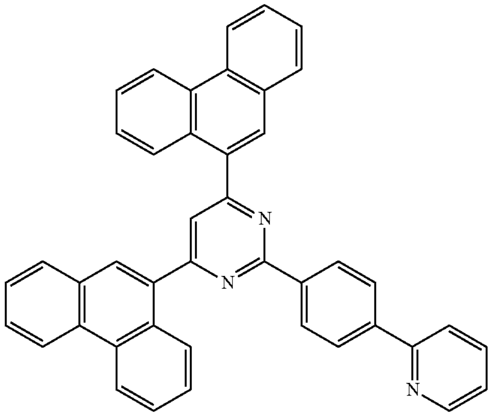
ET23
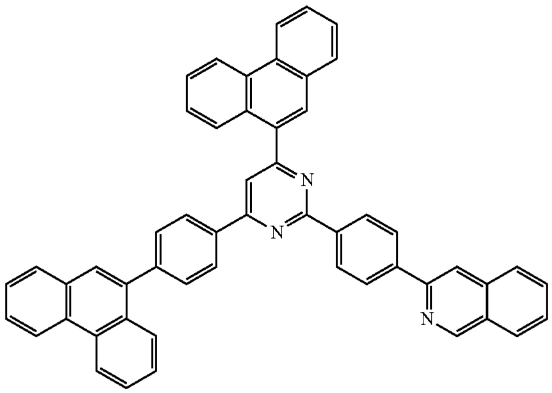
ET24
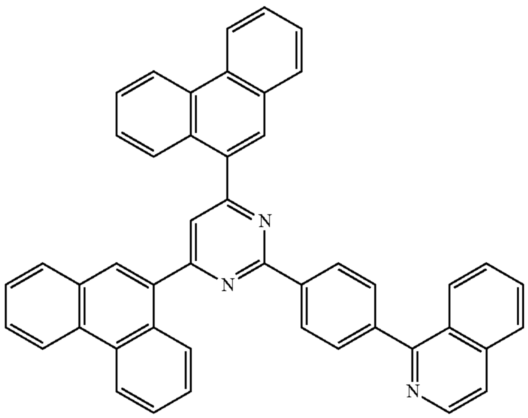

ET25
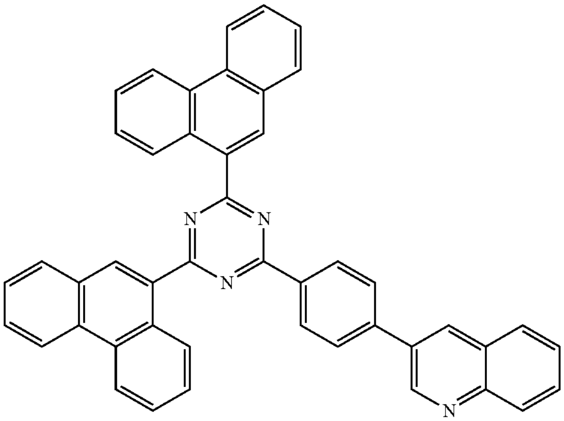
ET26
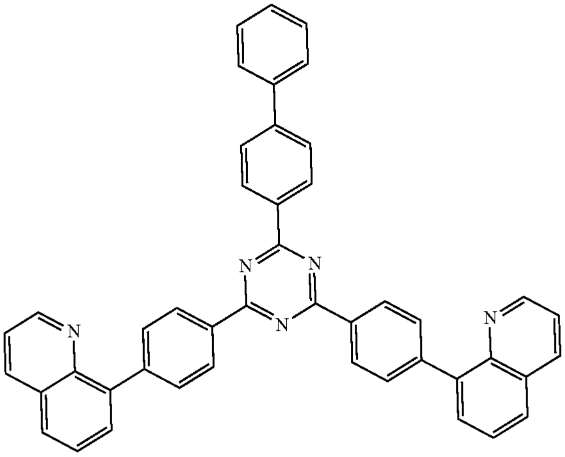
ET27
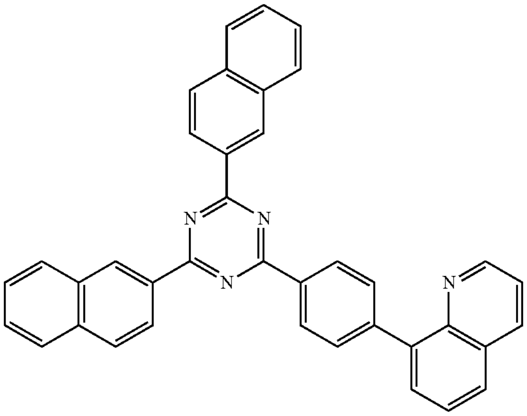
ET28
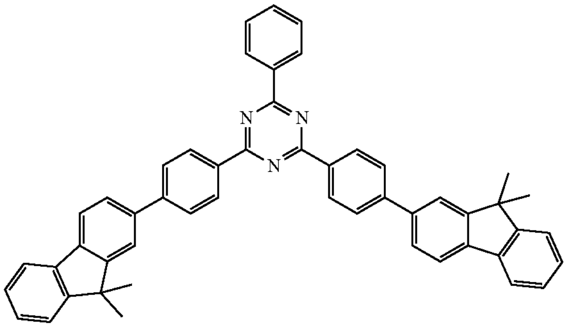
ET29
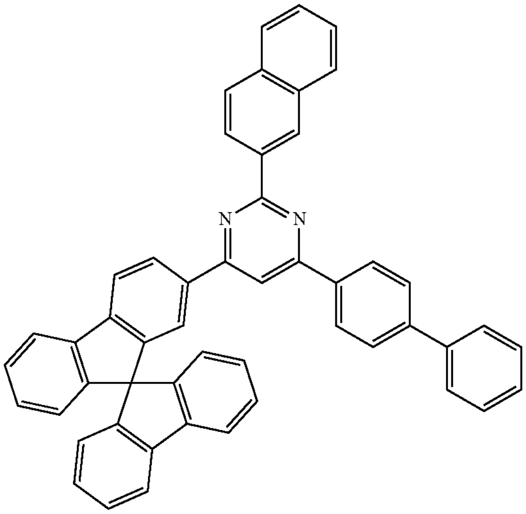
ET30
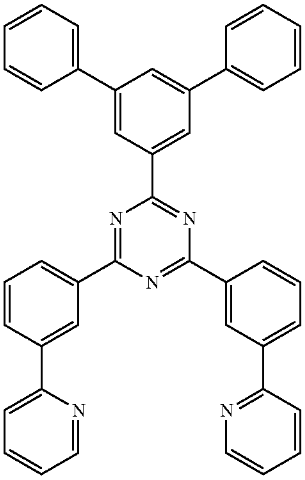

-continued

ET31

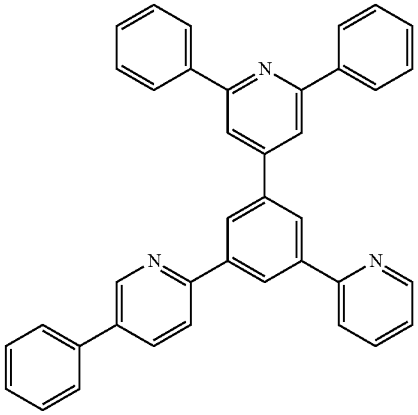

ET32

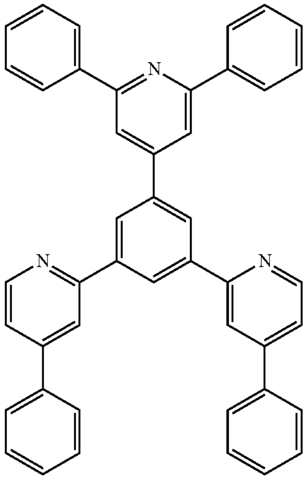

ET33

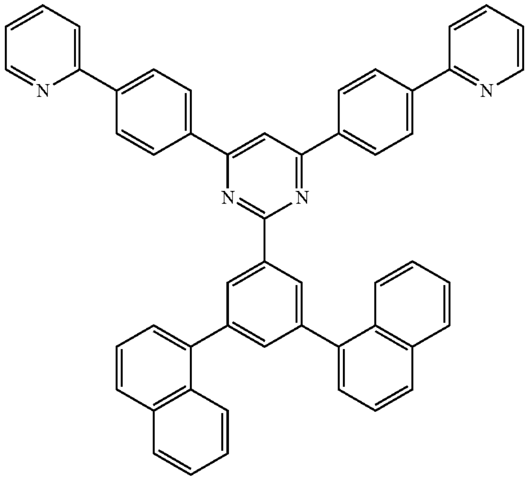

-continued

ET34

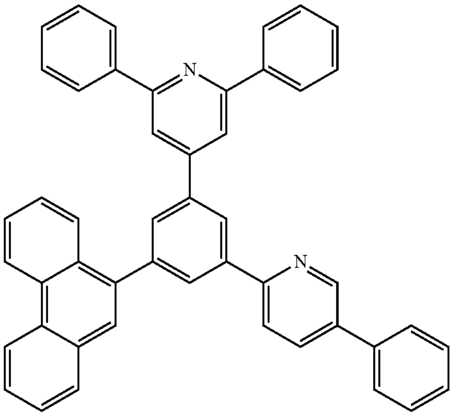

ET35

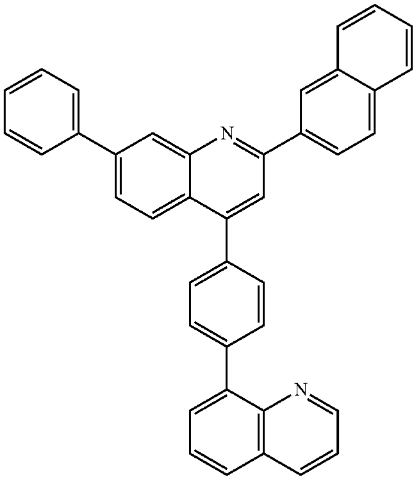

ET36

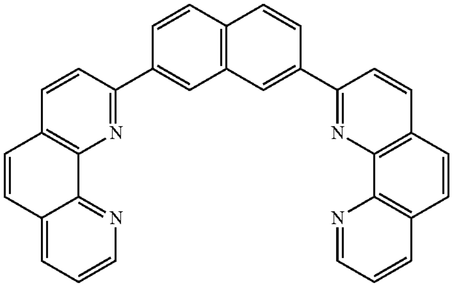

In one or more exemplary embodiments, the electron transport region may include at least one compound selected from 2,9-dimethyl-4,7-diphenyl-1,10-phenanthroline (BCP), 4,7-diphenyl-1,10-phenanthroline (Bphen), tris-(8-hydroxyquinoline)aluminum ($Alq_3$), bis(8-hydroxy-2-methylquinoline)-(4-phenylphenoxy)aluminum (BAlq), 3-(biphenyl-4-yl)-5-(4-tert-butylphenyl)-4-phenyl-4H-1,2,4-triazole (TAZ), and (4-naphthalen-1-yl-3,5-diphenyl-1,2,4-triazole) (NTAZ).

Alq3

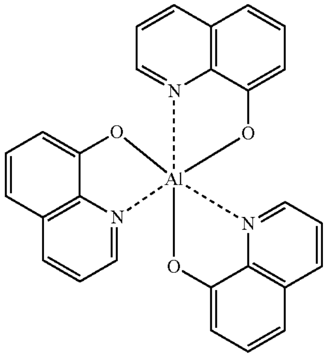

BAlq

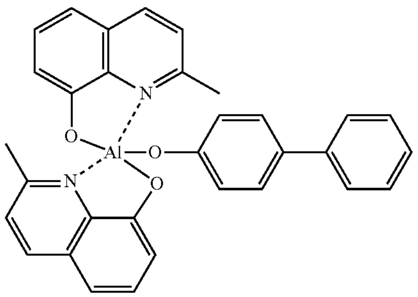

TAZ

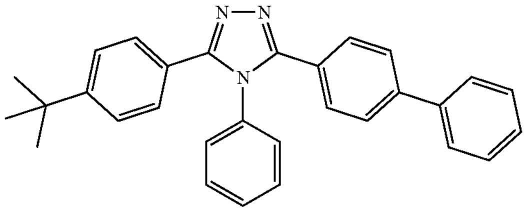

NTAZ

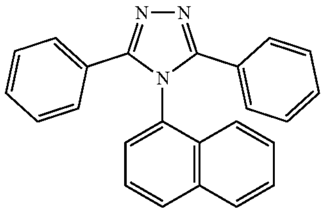

Thicknesses of the buffer layer, the hole blocking layer, and the electron control layer may each be in a range of about 20 Å to about 1,000 Å, for example, about 30 Å to about 300 Å. When the thicknesses of the buffer layer, the hole blocking layer, and the electron control layer are within these ranges, excellent hole blocking characteristics or excellent electron control characteristics may be obtained without a substantial increase in driving voltage.

The thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from a Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenyloxazole, a hydroxy phenylthiazole, a hydroxy diphenyloxadiazole, a hydroxy diphenylthiadiazole, a hydroxy phenylpyridine, a hydroxy phenylbenzimidazole, a hydroxy phenylbenzothiazole, a bipyridine, a phenanthroline, and a cyclopentadiene, but the exemplary embodiments are not limited thereto.

For example, the metal-containing material may include a Li complex. The Li complex may include, for example, Compound ET-D1 (lithium 8-hydroxyquinolate, LiQ) or ET-D2.

ET-D1

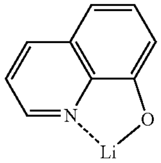

ET-D2

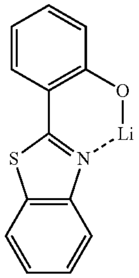

The electron transport region may include an electron injection layer that allows electrons to be easily provided from the second electrode 190. The electron injection layer may directly contact the second electrode 190.

The electron injection layer may have i) a single-layered structure including a single layer including a single material, ii) a single-layered structure including a single layer including a plurality of different materials, or iii) a multi-layered structure having a plurality of layers including a plurality of different materials.

The electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or any combination thereof.

The alkali metal may be selected from Li, Na, K, Rb, and Cs. In some exemplary embodiments, the alkali metal may be Li, Na, or Cs. In one or more exemplary embodiments, the alkali metal may be Li or Cs, but the exemplary embodiments are not limited thereto.

The alkaline earth metal may be selected from Mg, Ca, Sr, and Ba.

The rare earth metal may be selected from Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal, and the rare earth metal.

The alkali metal compound may be selected from alkali metal oxides, such as $Li_2O$, $Cs_2O$, or $K_2O$, and alkali metal halides, such as LiF, NaF, CsF, KF, LiI, NaI, CsI, or KI. In some exemplary embodiments, the alkali metal compound may be selected from LiF, $Li_2O$, NaF, LiI, NaI, CsI, and KI, but the exemplary embodiments are not limited thereto.

The alkaline earth metal compound may be selected from BaO, SrO, CaO, $Ba_xSr_{1-x}O$ ($0<x<1$), and $Ba_xCa_{1-x}O$ ($0<x<1$). In some exemplary embodiments, the alkaline earth metal compound may be selected from BaO, SrO, and CaO, but the exemplary embodiments are not limited thereto.

The rare earth metal compound may be selected from $YbF_3$, $ScF_3$, $Sc_2O_3$, $Y_2O_3$, $Ce_2O_3$, $GdF_3$, and $TbF_3$. In some exemplary embodiments, the rare earth metal compound may be selected from $YbF_3$, $ScF_3$, $TbF_3$, $YbI_3$, $ScI_3$, and $TbI_3$, but the exemplary embodiments are not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, or the rare earth metal complex may be selected from hydroxy quinoline, hydroxy isoquinoline, hydroxy benzoquinoline, hydroxy acridine, hydroxy phenanthridine, hydroxy phenyloxazole, hydroxy phenylthiazole, hydroxy diphenyloxadiazole, hydroxy diphenylthiadiazole, hydroxy phenylpyridine, hydroxy phenylbenzimidazole, hydroxy phenylbenzothiazole, bipyridine, phenanthroline, and cyclopentadiene, but the exemplary embodiments are not limited thereto.

The electron injection layer may consist of an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In one or more exemplary embodiments, the electron injection layer may further include an organic material. When the electron injection layer further includes an organic material, an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

The thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

Second Electrode 190

The second electrode 190 is disposed on the organic layer 150 having such a structure. The second electrode 190 may be a cathode which is an electron injection electrode, and in this regard, a material for forming the second electrode 190 may be selected from metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but the exemplary embodiments are not limited thereto. The second electrode 190 may be a transmissive electrode, a semi-transmissive electrode, or a reflective electrode.

The second electrode 190 may have a single-layered structure, or a multi-layered structure including two or more layers.

Description of FIGS. 2 and 3

Referring again to FIG. 2, an organic light-emitting device 20 according to another exemplary embodiment includes a first electrode 110, a second electrode 190, and an organic layer 150 disposed between the first electrode and the second electrode and including the first emission layer EML1, the second emission layer EML2 disposed between the first emission layer EML1 and the second electrode 190, and the second auxiliary layer AXL2 disposed between the second emission layer EML2 and the second electrode 190 and directly contacting the second emission layer EML2.

The second auxiliary layer AXL2 of the organic light-emitting device 20 may include a second host. The second host included in the second auxiliary layer AXL2 may be the same as described above.

For example, the second auxiliary layer AXL2 may consist of the second host, but the exemplary embodiments are not limited thereto.

Referring again to FIG. 3, an organic light-emitting device 30 according to another exemplary embodiment includes a first electrode 110, a second electrode 190, and an organic layer 150 disposed between the first electrode 110 and the second electrode 190 and including the first emission layer EML1, the second emission layer EML2 disposed between the first emission layer EML1 and the second electrode 190, and the third auxiliary layer AXL3 between the first emission layer EML1 and the second emission layer EML2.

The third auxiliary layer AXL3 of the organic light-emitting device 30 may include the first host or the second host. The first host or the second host included in the third auxiliary layer AXL3 may be the same as described above.

Referring to FIGS. 2 and 3, the first electrode 110, the second electrode 190, the first emission layer EML1, and the second emission layer EML2 are the same as described in connection with FIG. 1.

Hereinbefore, the organic light-emitting device according to some exemplary embodiments has been described in connection with FIGS. 1 to 3, but the exemplary embodiments are not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, the deposition may be performed at a deposition temperature of about 100° C. to about 500° C., a vacuum degree of about $10^{-8}$ torr to about $10^{-3}$ torr, and a deposition speed of about 0.01 Å/sec to about 100 Å/sec by taking into account a material to be included in a layer to be formed and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account a material to be included in a layer to be formed and the structure of a layer to be formed.

Apparatus

One or more of the organic light-emitting devices 10, 20, or 30 may be included in various apparatuses. Accordingly, another aspect of the invention provides an apparatus including: a thin-film transistor including a source electrode, a drain electrode, and an activation layer; and the organic light-emitting device, wherein the first electrode of the organic light-emitting device is electrically connected with one of the source electrode and the drain electrode of the thin-film transistor. The thin-film transistor may further include a gate electrode, a gate insulation layer, or the like.

The activation layer may include a crystalline silicon, an amorphous silicon, an organic semiconductor, an oxide semiconductor, or the like, but the exemplary embodiments are not limited thereto.

The apparatus may further include a sealing part for sealing the organic light-emitting device. The sealing part may allow an image from the organic light-emitting device to be implemented and may block outside air and moisture from penetrating into the organic light-emitting device. The sealing part may be a sealing substrate including a transparent glass or a plastic substrate. The sealing part may be a thin film encapsulation layer including a plurality of organic layers and/or a plurality of inorganic layers. When the sealing part is a thin-film encapsulation layer, the entire apparatus may be flexible. For example, the apparatus may be a light-emitting apparatus, an authentication apparatus, or an electronic apparatus.

The light-emitting apparatus may be used as various displays, light sources, and the like. The authentication apparatus may be, for example, a biometric authentication apparatus for authenticating an individual by using biometric information of a biometric body (for example, a finger tip, a pupil, or the like). The authentication apparatus may further include, in addition to the organic light-emitting device, a biometric information collector. The electronic apparatus may be applied to personal computers (for example, a mobile personal computer), mobile phones, digital cameras, electronic organizers, electronic dictionaries, electronic game machines, medical instruments (for example, electronic thermometers, sphygmomanometers, blood glucose meters, pulse measurement devices, pulse wave measurement devices, electrocardiogram (ECG) displays, ultrasonic diagnostic devices, or endoscope displays), fish finders, various measuring instruments, meters (for example, meters for a vehicle, an aircraft, and a vessel), projectors, and the like, but the exemplary embodiments are not limited thereto.

General Definition of Substituents

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group" used herein refers to a divalent group having a structure corresponding to the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" used herein refers to a divalent group having a structure corresponding to the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having a structure corresponding to the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having a structure corresponding to the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group" as used herein refers to a divalent group having a structure corresponding to $C_1$-$C_{10}$ heterocycloalkyl group.

The term $C_3$-$C_{10}$ cycloalkenyl group used herein refers to a monovalent monocyclic group that has 3 to 10 carbon atoms and at least one carbon-carbon double bond in the ring thereof and no aromaticity, and examples thereof include a cyclopentenyl group, a cyclohexenyl group, and a cycloheptenyl group. The term "$C_3$-$C_{10}$ cycloalkenylene group" as used herein refers to a divalent group having a structure corresponding to the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, Si, P, and S as a ring-forming atom, 1 to 10 carbon atoms, and at least one carbon-carbon double bond in its ring. Examples of the $C_1$-$C_{10}$ heterocycloalkenyl group include a 4,5-dihydro-1,2,3,4-oxatriazolyl group, a 2,3-dihydrofuranyl group, and a 2,3-dihydrothiophenyl group. The term "$C_1$-$C_{10}$ heterocycloalkenylene group" as used herein refers to a divalent group having a structure corresponding to the $C_1$-$C_{11}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, Si, P, and S as a ring-forming atom, in addition to 1 to 60 carbon atoms. The term "$C_1$-$C_{60}$ heteroarylene group" as used herein refers to a divalent group having a heterocyclic aromatic system that has at least one heteroatom selected from N, O, Si, P, and S as a ring-forming atom, in addition to 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, two or more rings may be fused to each other.

The term "$C_6$-$C_{60}$ aryloxy group" as used herein indicates —$OA_{102}$ (wherein $A_{102}$ is the $C_6$-$C_{60}$ aryl group), and the term "$C_6$-$C_{60}$ arylthio group" as used herein indicates —$SA_{103}$ (wherein $A_{103}$ is the $C_6$-$C_{60}$ aryl group).

The term "monovalent non-aromatic fused polycyclic group" as used herein refers to a monovalent group (for example, having 8 to 60 carbon atoms) having two or more rings fused with each other, only carbon atoms as ring-forming atoms, and no aromaticity in its entire molecular structure. A detailed example of the monovalent non-aromatic fused polycyclic group is a fluorenyl group. The term "divalent non-aromatic fused polycyclic group" as used herein refers to a divalent group having a structure corresponding to the monovalent non-aromatic fused polycyclic group.

The term "monovalent non-aromatic fused heteropolycyclic group" as used herein refers to a monovalent group (for example, having 1 to 60 carbon atoms) having two or more rings fused to each other, at least one heteroatom selected from N, O, Si, P, and S, other than carbon atoms, as a ring-forming atom, and no aromaticity in its entire molecular structure. An example of the monovalent non-aromatic fused heteropolycyclic group is a carbazolyl group. The term "divalent non-aromatic fused heteropolycyclic group" as used herein refers to a divalent group having a structure corresponding to monovalent non-aromatic fused heteropolycyclic group.

The term "$C_5$-$C_{60}$ carbocyclic group" as used herein refers to a monocyclic or polycyclic group that includes only carbon as a ring-forming atom and consists of 5 to 60 carbon atoms. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more exemplary embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group" as used herein refers to a group having a structure corresponding to the $C_5$-$C_{60}$ carbocyclic group, except that as a ring-forming atom, at least one heteroatom selected from N, O, Si, P, and S is used in addition to carbon (the number of carbon atoms may be in a range of 1 to 60).

The terms "hydrogen" and "deuterium" refer to their respective atoms and corresponding radicals, and the terms "—F, —Cl, —Br, and —I" are radicals of, respectively, fluorine, chlorine, bromine, and iodine.

As used herein, the term "atom" may mean an element or its corresponding radical bonded to one or more other atoms.

In the exemplary embodiments, at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic fused polycyclic group, the substituted divalent non-aromatic fused heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —$Si(Q_{11})(Qu)(Q_{13})$, —$N(Q_{11})(Q_{11})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group, each optionally substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, wherein $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic fused polycyclic group, a monovalent non-aromatic fused heteropolycyclic group, a biphenyl group, and a terphenyl group.

As used herein, a substituent for a monovalent group, e.g., alkyl, may also be, independently, a substituent for a corresponding divalent group, e.g., alkylene.

The term "Ph" used herein refers to a phenyl group, the term "Me" used herein refers to a methyl group, the term "Et" used herein refers to an ethyl group, the term "ter-Bu" or "$Bu^t$" used herein refers to a tert-butyl group, and the term "OMe" used herein refers to a methoxy group.

The term "biphenyl group" as used herein refers to "a phenyl group substituted with a phenyl group." In other words, the "biphenyl group" is a substituted phenyl group having a $C_6$-$C_{60}$ aryl group as a substituent.

The term "terphenyl group" as used herein refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

As used herein, the term "transition element or metal" can mean any of a number of elements in which the filling of the outermost shell to eight electrons within a period is interrupted to bring the penultimate shell from 8 to 18 or 32 electrons. Only these elements can use penultimate shell orbitals as well as outermost shell orbitals in bonding. Transition elements include elements 21 through 29 (scandium through copper), 39 through 47 (yttrium through silver), 57 through 79 (lanthanum through gold), and all known elements from 89 (actinium) on. All of these elements are metals.

* and *' used herein, unless defined otherwise, each refer to a binding site to a neighboring atom in a corresponding formula.

Hereinafter, an organic light emitting device according to some exemplary embodiments will be described in more detail with reference to Examples.

EXAMPLES

Example 1

A 15 Ω/$cm^2$ (1,200 Å) ITO glass substrate (anode) from Corning, Inc. of Corning, New York was cut to the size of 50 mm×50 mm×0.5 mm, sonicated with isopropyl alcohol and pure water, each for 15 minutes, and then cleaned by exposure to ultraviolet rays and ozone for 30 minutes. Then, the ITO glass substrate was provided to a vacuum deposition apparatus.

Compound HT1 was vacuum-deposited on the ITO glass substrate to form a hole transport layer having a thickness of 120 nm.

Compounds 1-3 was vacuum-deposited on the hole transport layer to form a first auxiliary layer having a thickness of 5 nm.

Compound 1-3 (first host), Compound 2-16 (second host), and Compound 3-18 (first dopant) were co-deposited at a weight ratio of 7:3:1 on the first auxiliary layer to form a first emission layer having a thickness of 15 nm.

Compound 1-3 (first host), Compound 2-16 (second host), and Compound 3-11 (second dopant) were co-deposited at a weight ratio of 7:3:1 on the first emission layer to form a second emission layer having a thickness of 15 nm.

Compound ET1 was deposited on the second emission layer to form a first electron transport layer having a thickness of 5 nm, and Compound ET2 and LiQ were co-deposited at a weight ratio of 5:5 on the first electron transport layer to form a second electron transport layer having a thickness of 20 nm.

LiQ was vacuum-deposited on the second electron transport layer to form an electron injection layer having a thickness of 1 nm, and then Mg and Ag were co-deposited at a weight ratio of 5:5 on the electron injection layer to form a cathode having a thickness of 10 nm, thereby completing the manufacture of an organic light-emitting device of Example 1.

HT1

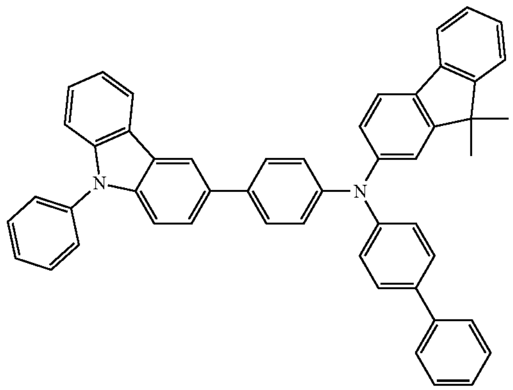

ET1

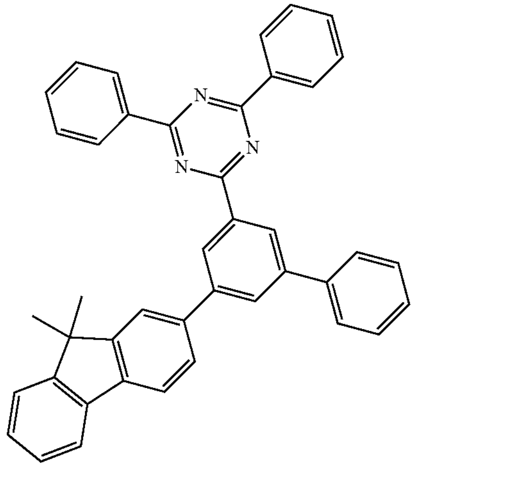

-continued

ET2

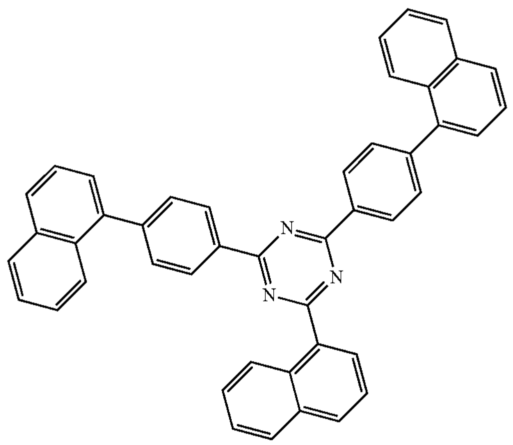

Example 2

An organic light-emitting device was manufactured in the same manner as in Example 1, except that, as a first dopant, Compound 3-11 was used instead of Compound 3-14 in forming a first emission layer, and as a second dopant, Compound 3-18 was used instead of Compound 3-11 in forming a second emission layer.

Example 3

An organic light-emitting device was manufactured in the same manner as in Example 1, except that a first host, a second host, and a first dopant were co-deposited at a weight ratio of 5:5:1 in forming a first emission layer, and a first host, a second host, and a second dopant were co-deposited at a weight ratio of 5:5:1 in forming a second emission layer.

Example 4

An organic light-emitting device was manufactured in the same manner as in Example 1, except that a first host, a second host, and a first dopant were co-deposited at a weight ratio of 5:5:1 by using, as a first dopant, Compound 3-11 instead of Compound 3-18 in forming a first emission layer, and a first host, a second host, and a second dopant were co-deposited at a weight ratio of 5:5:1 by using, as a second dopant, Compound 3-18 instead of Compound 3-11 in forming a second emission layer.

Example 5

An organic light-emitting device was manufactured in the same manner as in Example 1, except that a first host, a second host, and a first dopant were co-deposited at a weight ratio of 5:5:1 by using, as a first dopant, Compound 3-11 instead of Compound 3-18 in forming a first emission layer, and a first host, a second host, and a second dopant were co-deposited at a weight ratio of 5:5:1 by using, as a second dopant, Compound 4-13 instead of Compound 3-11 in forming a second emission layer.

Example 6

An organic light-emitting device was manufactured as in Example 1, except that a first host, a second host, and a first dopant were co-deposited at a weight ratio of 5:5:1 by using, as a first dopant, Compound 3-11 instead of Compound 3-18 in forming a first emission layer, a first host, a second host, and a second dopant were co-deposited at a weight ratio of 5:5:1 by using, as a second dopant, Compound 3-18 instead of Compound 3-11 in forming a second emission layer, and Compound 2-30 was deposited on the second emission layer to form a second auxiliary layer having a thickness of 5 nm.

Example 7

An organic light-emitting device was manufactured as in Example 1, except that a first host, a second host, and a first dopant were co-deposited at a weight ratio of 5:5:1 by using, as a first dopant, Compound 3-11 instead of 3-18 in forming a first emission layer, a first host, a second host, and a second dopant were co-deposited at a weight ratio of 5:5:1 by using, as a second dopant, Compound 3-18 instead of Compound 3-11 in forming a second emission layer, Compound 1-3 was deposited between the first emission layer and the second emission layer to form a third auxiliary layer having a thickness of 5 nm, and Compound 2-30 was deposited on the second emission layer to form a second auxiliary layer having a thickness of 5 nm.

Example 8

An organic light-emitting device was manufactured as in Example 1, except that a first host, a second host, and a first dopant were co-deposited at a weight ratio of 5:5:1 by using, as a first dopant, Compound 3-11 instead of Compound 3-18 in forming a first emission layer, a first host, a second host, and a second dopant were co-deposited at a weight ratio of 5:5:1 by using, as a second dopant, Compound 3-18 instead of Compound 3-11 in forming a second emission layer, and Compound 2-30 was deposited on the second emission layer to form a second auxiliary layer having a thickness of 5 nm instead of forming a first auxiliary layer.

Comparative Example 1

An organic light-emitting device was manufactured in the same manner as in Example 1, except that, without formation of a second emission layer, an emission layer was formed as a single layer that is a first emission layer.

Comparative Example 2

An organic light-emitting device was manufactured in the same manner as in Example 2, except that, without formation of a second emission layer, an emission layer was formed as a single layer that is a first emission layer.

Comparative Example 3

An organic light-emitting device was manufactured in the same manner as in Example 1, except that, without formation of a second emission layer, Compound cmp1 (first host), Compound cmp2 (second host), and Compound Pt-2(dopant) were co-deposited at a weight ratio of 5:5:1 to form an emission layer as a single layer that is a first emission layer, and Compound cmp2 was deposited on the first emission layer to form a second auxiliary layer having a thickness of 5 nm instead of forming a first auxiliary layer.

<cmp1>

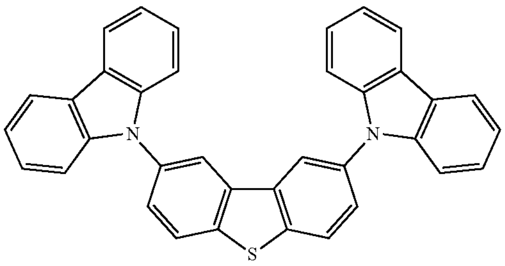

<cmp2>

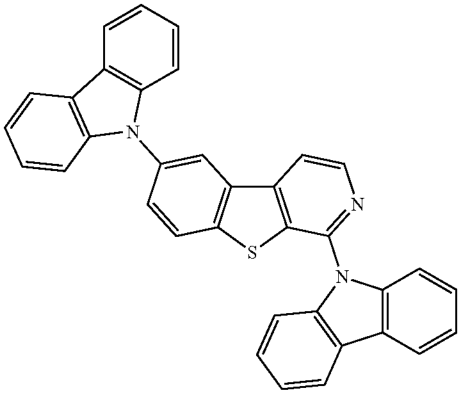

<Pt-2>

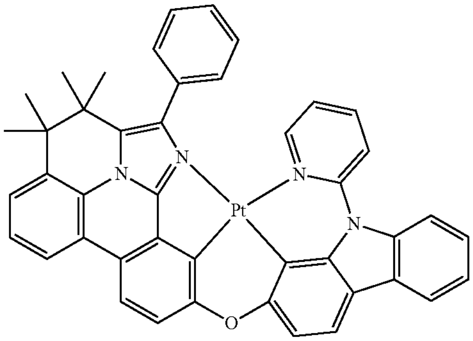

Comparative Example 4

An organic light-emitting device was manufactured in the same manner as in Example 1, except that, without formation of a second emission layer, Compound D1 (first host), Compound A1 (second host), and PD79 were co-deposited at a weight ratio of 5:5:1 to form an emission layer as a single layer that is a first emission layer, and Compound A4 was deposited on the first emission layer to form a second auxiliary layer having a thickness of 5 nm instead of forming a first auxiliary layer.

D1

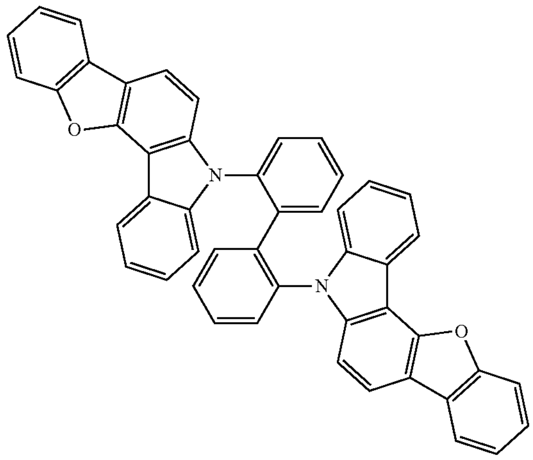

A1

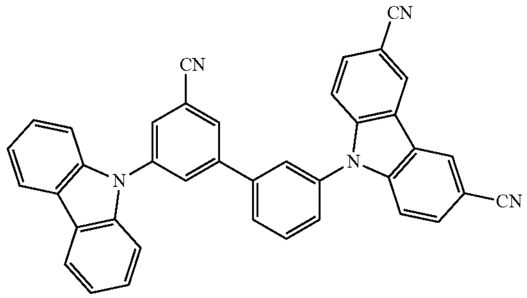

PD79

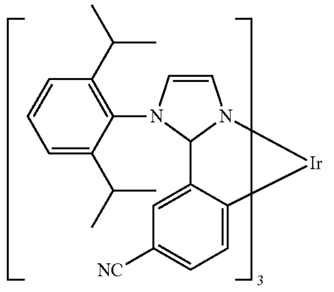

A4

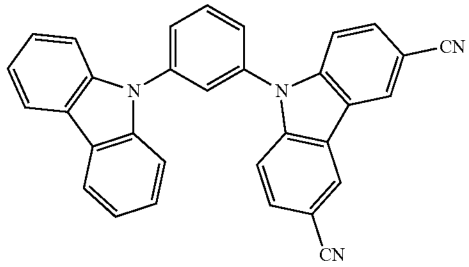

Evaluation Example 1

Lifespan and driving voltage of organic light-emitting devices manufactured according to Examples 1 to 8 and Comparative Examples 1 to 4 were measured at a current density of 10 mA/$cm^2$ by using a source-measure unit sold under the trade designation Keithley SMU 236 by Tektronix, Inc., of Beaverton, Oregon and a luminance meter sold under the trade designation PR650 from Konica Minolta, Inc. of Tokyo, Japan, and results thereof are shown in Table 1. The lifespan indicates an amount of time that lapsed when luminance was 90% of initial luminance (100%). The lifespan was measured based on Comparative Example 1 as 100%.

In detail, the organic light-emitting devices manufactured according to Examples 1 to 5 have improved lifespans, compared to the organic light-emitting devices manufactured according to Comparative Examples 1 and 2, and the organic light-emitting devices manufactured according to Examples 6 and 8 have improved lifespan, compared to the organic light-emitting devices manufactured according to Comparative Examples 3 and 4. Accordingly, by including a double emission layer in an organic light-emitting device, lifespan characteristics may be improved.

Furthermore, the organic light-emitting device manufactured according to Example 7, in which a first auxiliary layer, a second auxiliary layer, and a third auxiliary layer are formed at each interface of a first emission layer and a second emission layer, has much significantly improved lifespan, compared to the organic light-emitting devices manufactured according to Comparative Examples.

TABLE 1

| | | Emission layer | | | | | |
|---|---|---|---|---|---|---|---|
| | First auxiliary layer | First emission layer | Third auxiliary layer | Second emission layer | Second auxiliary layer | Lifespan | Driving voltage (V) |
| Example 1 | Compound 1-3 | Compound 1-3:Compound 2-16:Compound 3-18 (7:3:1) | | Compound 1-3:Compound 2-16:Compound 3-11 (7:3:1) | — | 120% | 5.3 V |
| Example 2 | Compound 1-3 | Compound 1-3:Compound 2-16:Compound 3-11 (7:3:1) | | Compound 1-3:Compound 2-16:Compound 3-18 (7:3:1) | — | 125% | 5.6 V |
| Example 3 | Compound 1-3 | Compound 1-3:Compound 2-16:Compound 3-18 (5:5:1) | | Compound 1-3:Compound 2-16:Compound 3-11 (5:5:1) | | 130% | 5.1 V |
| Example 4 | Compound 1-3 | Compound 1-3:Compound 2-16:Compound 3-11 (5:5:1) | | Compound 1-3:Compound 2-16:Compound 3-18 (5:5:1) | | 150% | 5.3 V |
| Example 5 | Compound 1-3 | Compound 1-3:Compound 2-16:Compound 3-11 (5:5:1) | | Compound 1-3:Compound 2-16:Compound 4-13 (5:5:1) | | 130% | 4.9 |
| Example 6 | Compound 1-3 | Compound 1-3:Compound 2-16:Compound 3-11 (5:5:1) | | Compound 1-3:Compound 2-16:Compound 3-18 (5:5:1) | Compound 2-30 | 140% | 5.4 V |
| Example 7 | Compound 1-3 | Compound 1-3:Compound 2-16:Compound 3-11 (5:5:1) | Compound 1-3 | Compound 1-3:Compound 2-16:Compound 3-18 (5:5:1) | Compound 2-30 | 155% | 5.3 V |
| Example 8 | | Compound 1-3:Compound 2-16:Compound 3-11 (5:5:1) | | Compound 1-3:Compound 2-16:Compound 3-18 (5:5:1) | Compound 2-30 | 125% | 5.1 V |
| Comparative Example 1 | Compound 1-3 | Compound 1-3:Compound 2-16:Compound 3-18 (7:3:1) | | — | | 100% | 5.0 V |
| Comparative Example 2 | Compound 1-3 | Compound 1-3:Compound 2-16:Compound 3-11 (7:3:1) | | — | | 110% | 4.8 V |
| Comparative Example 3 | | Compound cmp1:Compound cmp2:Compound Pt-2 (5:5:1) | | — | Compound cmp2 | 70% | 5.5 |
| Comparative Example 4 | | Compound D1:Compound A1:Compound PD79 (5:5:1) | | — | Compound A4 | 80% | 5.3 |

The results in Table 1 show that organic light-emitting devices manufactured according to Examples 1 to 8 have significantly and unexpectedly improved lifespan, compared to organic light-emitting devices manufactured according to Comparative Examples 1 to 4.

Some of the advantages that may be achieved by exemplary implementations/embodiments of the invention and/or exemplary methods of the invention include an improved charge balance in an emission layer, and the organic light-emitting device may have high efficiency and long lifespan.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An organic light-emitting device comprising:

a first electrode;

a second electrode; and an organic layer disposed between the first electrode and the second electrode, the organic layer comprising a first emission layer, a second emission layer disposed between the first emission layer and the second electrode, and at least one auxiliary layer, wherein the at least one auxiliary layer comprises an optional first auxiliary layer having a first host disposed between the first electrode and the first emission layer and directly contacting the first emission layer, a second auxiliary layer having a second host disposed between the second emission layer and the second electrode and directly contacting the second emission layer, and a third auxiliary layer comprising either a first host or a second host disposed between the first emission layer and the second emission layer;

wherein the organic layer further comprises a hole transport region disposed between the first electrode and the first emission layer or the first auxiliary layer and directly contacting the first electrode, and an electron transport region disposed between the second emission layer or the second auxiliary layer and the second electrode and directly contacting the second electrode, wherein the hole transport region comprises a hole transport layer and the electron transport region comprises an electron transport layer and an electron injection layer, wherein the electron transport layer comprises a first electron transport layer and a second electron transport layer, the first emission layer comprises a first host, a second host, and a first dopant and emits blue light; and the second emission layer comprises a first host, a second host, and a second dopant and emits blue light; wherein:

the first hosts included in the first emission layer, the second emission layer, and the at least one auxiliary layer comprise a compound of Formula 1-1 and are identical to or different from each other, when the third auxiliary layer comprises a first host, a first host included in the third auxiliary layer and a first host included in the first emission layer are identical to or different from each other, and a first host included in the third auxiliary layer and a first host included in the second emission layer are identical to or different from each other; and when the third auxiliary layer comprises a second host, a second host included in the third auxiliary layer and a second host included in the first emission layer are identical to or different from each other, and a second host included in the third auxiliary layer and a second host included in the second emission layer are identical to or different from each other:

<Formula 1-1>

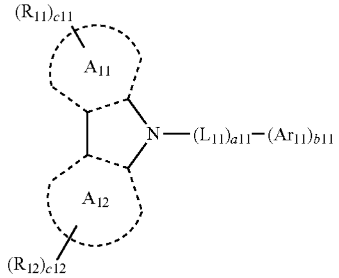

wherein, in Formula 1-1, $A_{11}$ and $A_{12}$ are each, independently from one another, benzene, naphthalene, anthracene, phenanthrene, fluoranthene, triphenylene, pyrene, chrysene, indene, fluorene, spiro-bifluorene, benzofluorene, dibenzofluorene, carbazole, benzocarbazole, dibenzocarbazole, dibenzofuran, or a dibenzothiophene;

$R_{11}$ and $R_{12}$ are each, independently from one another, hydrogen, deuterium, —F, —Cl, —Br, —I, a hydroxyl group, a cyano group, a nitro group, an amidino group, a hydrazine group, a hydrazone group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, —Si($Q_1$)($Q_2$)($Q_3$), —N($Q_1$)($Q_2$), or —B($Q_1$)($Q_2$);

c11 to c12 are each, independently from one another, an integer from 1 to 8;

$L_{11}$ is a single bond or a r electron-deficient nitrogen-free cyclic group;

a π electron-deficient nitrogen-free cyclic group substituted with at least one, independently from one another, deuterium, a cyano group, a $C_1$-$C_{60}$ alkyl group, a $C_1$-$C_{60}$ alkoxy group, and a π electron-deficient nitrogen-free cyclic group;

a11 is an integer from 1 to 3;

Ar11 is:

a π electron-deficient nitrogen-free cyclic group;

a π electron-deficient nitrogen-free cyclic group substituted with at least one of deuterium, a cyano group, a $C_1$-$C_{60}$ alkyl group, a $C_1$-$C_{60}$ alkoxy group, and a π electron-deficient nitrogen-free cyclic group; or —Si($Q_1$)($Q_2$)($Q_3$) or —N($Q_1$)($Q_2$); and b11 is an integer from 1 to 5;

wherein $Q_1$ to $Q_3$ are each, independently from one another, hydrogen, deuterium, a $C_1$-$C_{60}$ alkyl group, a $C_2$-$C_{60}$ alkenyl group, a $C_2$-$C_{60}$ alkynyl group, a $C_1$-$C_{60}$ alkoxy group, a r electron-deficient nitrogen-free cyclic group, a biphenyl group, or a terphenyl group, and the second hosts included in the first emission layer, the second emission layer and the at least one auxiliary layer comprise at least one of an electron transport host and a bipolar host and are identical to or different from each other;

the first dopant and the second dopant, each comprise, independently from one another, at least one of a phosphorescent organometallic compound and a thermally activated delayed fluorescence ("TADF") compound satisfying Equation 1 below, and the first dopant and the second dopant are different from each other:

$$\Delta E_{ST}=S_1-T_1\leq 0.3\text{ eV}$$ <Equation 1> wherein, in Equation 1, $S_1$ is a lowest excitation singlet energy level (eV) of the TADF compound, and $T_1$ is a lowest excitation triplet energy level (eV) of the TADF compound.

2. The organic light-emitting device of claim 1, wherein the electron transport host comprises at least one electron withdrawing group, and the bipolar host comprises at least one electron withdrawing group and at least one electron donating group.

3. The organic light-emitting device of claim 2, wherein the electron withdrawing group is:

—F, —$CFH_2$, —$CF_2H$, —$CF_3$, —CN, or —$NO_2$;

a $C_1$-$C_{60}$ alkyl group substituted with at least one of —F, —$CFH_2$, —$CF_2H$, —$CF_3$, —CN, and —$NO_2$; or a substituted or unsubstituted IT electron-deficient nitrogen-containing cyclic group; and the electron donating group is a substituted or unsubstituted carbazole group, a substituted or unsubstituted dibenzofuran group, a substituted or unsubstituted dibenzothiophene group, a substituted or unsubstituted indolocarbazole group, a substituted or unsubstituted benzofurocarbazole group, a substituted or unsubstituted benzothienocarbazole group, a substituted or unsubstituted acridine group, a substituted or unsubstituted phenoxazine group, a substituted or unsubstituted phenothiazine group, a substituted or unsubstituted phenazine group, or —$N(Q_1)(Q_2)$;

wherein $Q_1$ and $Q_2$ are each, independently from one another, hydrogen, deuterium, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $\pi$ electron-deficient nitrogen-free cyclic group, a biphenyl group, or a terphenyl group.

4. The organic light-emitting device of claim 1, wherein the second hosts included in the first emission layer, the second emission layer, and the at least one auxiliary layer comprise at least one of compounds of Formulae 2-1, 2-2, and 2-3:

<Formula 2-1>

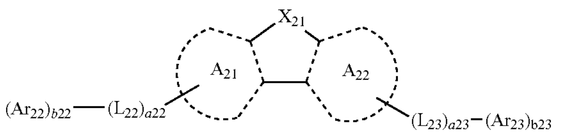

<Formula 2-2>

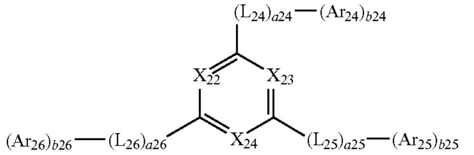

<Formula 2-3>

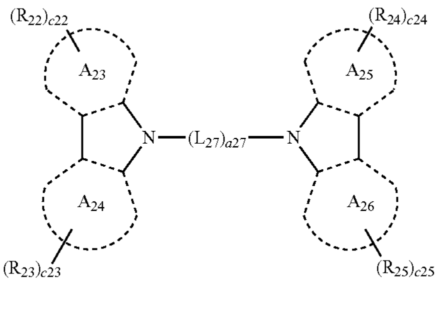

wherein, in Formulae 2-1 to 2-3, $A_{21}$ to $A_{26}$ are each, independently from one another, a $C_5$-$C_{60}$ carbocyclic group or a $C_1$-$C_{60}$ heterocyclic group;

$X_{21}$ is N-[$(L_{21})_{a21}$—$(Ar_{21})_{b21}$], O, or S;

$X_{22}$ to $X_{24}$ are each, independently from one another N or C($R_{21}$), wherein at least one of $X_{22}$ to $X_{24}$ is N;

$L_{21}$ to $L_{27}$ are each, independently from one another, a single bond, a substituted or unsubstituted $C_5$-$C_{60}$ carbocyclic group, or a substituted or unsubstituted $C_1$-$C_{60}$ heterocyclic group;

a21 to a27 are each, independently from one another an integer from 1 to 3;

$Ar_{21}$ to $Ar_{26}$ and $R_{21}$ to $R_{25}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent nonaromatic fused heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)_2$ $(Q_1)$, or —$P(=O)(Q_1)(Q_2)$;

b21 to b26 are each, independently from one another, an integer from 1 to 5;

c22 to c25 are each, independently from one another, an integer from 1 to 8;

in Formula 2-1, at least one of $A_{21}$, $A_{22}$, $L_{21}$ to $L_{23}$, and $Ar_{21}$ to $Ar_{23}$, each independently from one another, comprises a TT electron-deficient nitrogen-containing cyclic group;

in Formula 2-3, at least one of $R_{22}$ to $R_{25}$, each independently from one another, comprises an electron withdrawing group; and at least one substituent of the substituted $C_5$-$C_{60}$ carbocyclic group, the substituted $C_1$-$C_{60}$ heterocyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent non-aromatic fused heteropolycyclic group is:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each, independently from one another, optionally substituted with at least one of deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group, each, independently from one another, optionally substituted with at least one of deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$), and —P(=O)($Q_{21}$)($Q_{22}$); and —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$);

wherein $Q_1$ to $Q_3$, $Q_{11}$ to $Q_{13}$, $Q_{21}$ to $Q_{23}$, and $Q_{31}$ to $Q_{33}$ are each, independently from one another, hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, a biphenyl group, or a terphenyl group.

5. The organic light-emitting device of claim 1, wherein the phosphorescent organometallic compound of the first dopant, the second dopant, or both the first dopant and the second dopant is a compound of Formula 3:

$M_{31}(L_{31})_{n31}(L_{32})_{n32}$ <Formula 3> wherein, in Formula 3, $M_{31}$ is a transition metal;

$L_{31}$ is a ligand of Formula 3A, a ligand of Formula 3B, or a ligand of Formula 3C:

<Formula 3A>

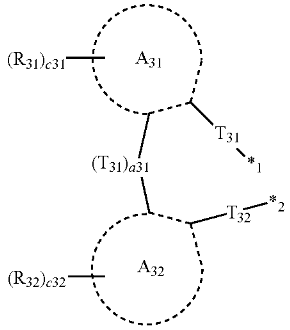

<Formula 3B>

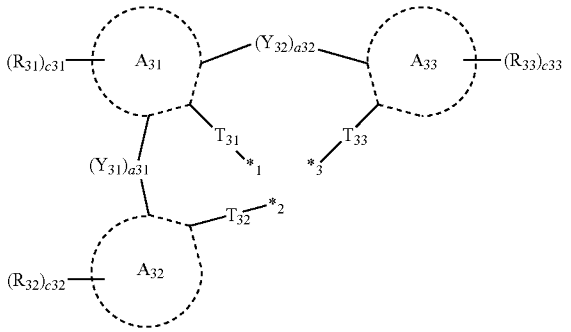

<Formula 3C>

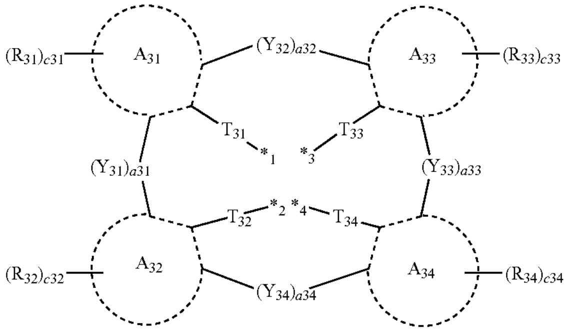

$L_{32}$ is a monodentate ligand, a bidentate ligand, or a tridentate ligand;

n31 is 1 or 2;

n32 is 0, 1, 2, 3, or 4;

$A_{31}$ to $A_{34}$ are, independently from one another, a $C_5$-$C_{30}$ carbocyclic group or a $C_1$-$C_{30}$ heterocyclic group;

each of $T_{31}$ to $T_{34}$ is a single bond;

$Y_{31}$ to $Y_{34}$ are each, independently from one another, a single bond, a double bond, a substituted or unsubstituted $C_6$-$C_{30}$ arylene group, a substituted or unsubstituted $C_1$-$C_{30}$ heteroarylene group, *—O—*', *—S—*', *—C(=O)—*', *—S(=O)—*', *—C($R_{35}$)($R_{36}$)—*', *—C($R_{35}$)=C($R_{36}$)—*', *—C($R_{35}$)=**, *—Si($R_{35}$)($R_{36}$)—*', *—B($R_{35}$)—*', *—N($R_{35}$)—*', or *—P($R_{35}$)—*';

a31 to a33 are each, independently from one another, 1, 2, or 3;

a34 is 0, 1, 2, or 3, wherein when a34 is 0, $A_{32}$ and $A_{34}$ are not linked to each other;

$*_1$, $*_2$, $*_3$, and $*_4$ are each indicating a binding site to $M_{31}$;

$R_{31}$ to $R_{36}$ are each, independently from one another, hydrogen, deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, —$C(Q_1)(Q_2)(Q_3)$, —$Si(Q_1)(Q_2)(Q_3)$, —$B(Q_1)(Q_2)$, —$N(Q_1)(Q_2)$, —$P(Q_1)(Q_2)$, —$C(=O)(Q_1)$, —$S(=O)(Q_1)$, —$S(=O)_2(Q_1)$, —$P(=O)(Q_1)(Q_2)$, or —$P(=S)(Q_1)(Q_2)$, wherein adjacent groups among $R_{31}$ to $R_{36}$ are optionally linked to each other to form a substituted or unsubstituted $C_5$-$C_{60}$ carbocyclic group or a substituted or unsubstituted $C_1$-$C_{60}$ heterocyclic group;

adjacent groups among $R_{31}$ to $R_{36}$ and $Y_{31}$ to $Y_{34}$ are optionally linked to each other to form a substituted or unsubstituted $C_5$-$C_{60}$ carbocyclic group or a substituted or unsubstituted $C_1$-$C_{60}$ heterocyclic group;

c31 to c34 are each, independently from one another, an integer of 0 to 10; and at least one substituent of the substituted $C_6$-$C_{30}$ arylene group, the substituted $C_1$-$C_{30}$ heteroarylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, the substituted monovalent non-aromatic fused heteropolycyclic group, the substituted $C_5$-$C_{60}$ carbocyclic group, and the substituted $C_1$-$C_{60}$ heterocyclic group is:

deuterium, —F, —Cl, —Br, —I, a hydroxyl group, a cyano group, a nitro group, an amidino group, a hydrazino group, and a hydrazono group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each, independently from one another, optionally substituted with at least one of deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group, each, independently from one another, optionally substituted with at least one of deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$;

wherein $Q_1$ to $Q_3$, $Q_{11}$ to $Q_{13}$, $Q_{21}$ to $Q_{23}$, and $Q_{31}$ to $Q_{33}$ are each, independently from one another, hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, a biphenyl group, or a terphenyl group.

6. The organic light-emitting device of claim 1, wherein the TADF compound of the first dopant, the second dopant, or both the first dopant and the second dopant comprises at least one of compounds of Formulae 4-1 to 4-8:

<Formula 4-1>

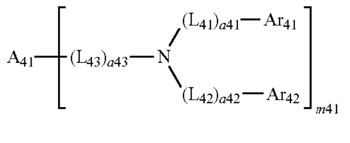

<Formula 4-2>

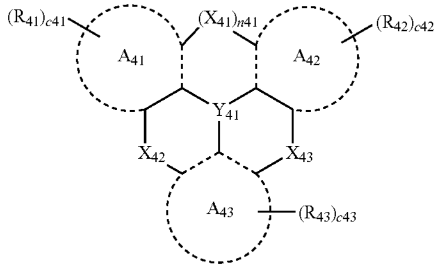

-continued

<Formula 4-3>

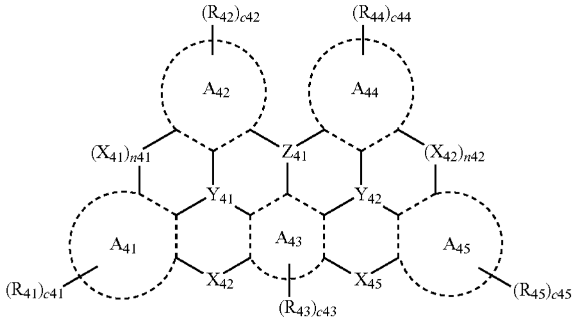

<Formula 4-4>

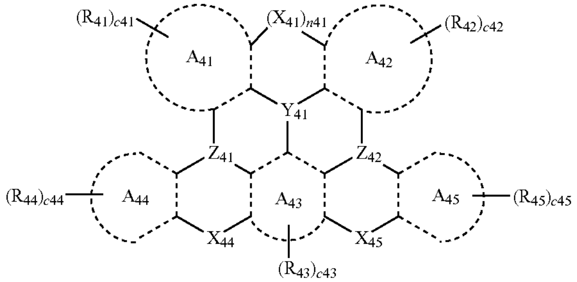

<Formula 4-5>

$$(EDG)_{b41}—[(L_{44})_{a44}-(EWG)_{t42}]_{s41}$$

<Formula 4-6>

$$(EWG)_{t42}—[(L_{44})_{a44}-(EDG)_{b41}]_{s42}$$

<Formula 4-7>

$$(EDG)_{b411}—[(L_{44})_{a44}-(EWG)_{t42}-(L_{45})_{a45}-(EDG)_{b412}$$

<Formula 4-8>

$$(EWG)_{t421}—[(L_{44})_{a44}-(EDG)_{b41}-(L_{45})_{a45}-(EWG)_{t422}$$

wherein, in Formula 4-1, $A_{41}$ is a substituted or unsubstituted $C_5$-$C_{60}$ carbocyclic group or a substituted or unsubstituted $C_1$-$C_{60}$ heterocyclic group;

$L_{41}$ to $L_{43}$ are each, independently from one another, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic fused polycyclic group, or a substituted or unsubstituted divalent non-aromatic fused heteropolycyclic group;

a41 to a43 are each, independently from one another, 0, 1, 2, or 3;

$Ar_{41}$ and $Ar_{42}$ are each, independently from one another, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, or a substituted or unsubstituted monovalent non-aromatic fused heteropolycyclic group;

m41 is 1, 2, 3, 4, 5, or 6;

in Formulae 4-2 to 4-4, $X_{41}$ to $X_{45}$ are each, independently from one another, a single bond, O, S, $N(R_{46})$, $B(R_{46})$, $C(R_{46})(R_{47})$, or $Si(R_{46})(R_{47})$;

n41 and n42 are each, independently from one another, 0, 1, or 2, wherein when n41 is 0, $A_{41}$ and $A_{42}$ are not linked to each other, and when n42 is 0, $A_{44}$ and $A_{45}$ are not linked to each other;

$Y_{41}$ and $Y_{42}$ are each, independently from one another, N, B, or P;

$Z_{41}$ and $Z_{42}$ are each, independently from one another, N, $C(R_{46})$, or $Si(R_{46})$;

$A_{41}$ to $A_{45}$ are each, independently from one another, a $C_5$-$C_{30}$ carbocyclic group or a $C_1$-$C_{30}$ heterocyclic group;

$R_{41}$ to $R_{47}$ are each, independently from one another, hydrogen, deuterium, —F, —Cl, —Br, —I, a hydroxyl group, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic fused polycyclic group, a substituted or unsubstituted monovalent non-aromatic fused heteropolycyclic group, $—Si(Q_1)(Q_2)(Q_3)$, $—B(Q_1)(Q_2)$, $—C(=O)(Q_1)$, $—N(Q_1)(Q_2)$, $—P(=O)(Q_1)(Q_2)$, or $—S(=O)_2(Q_1)(Q_2)$;

c41 to c45 are each, independently from one another, an integer from 1 to 8;

in Formulae 4-5 to 4-8,

EDG is an electron donating group, and EWG is an electron withdrawing group;

b41, b411, b412, t42, t421, and t422 are each, independently from one another, 1, 2, or 3;

$L_{44}$ to $L_{45}$ are each, independently from one another, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic fused polycyclic group, or a substituted or unsubstituted divalent non-aromatic fused heteropolycyclic group;

a44 and a45 are each, independently from one another, 0, 1, 2, or 3;

s41 and s42 are each, independently from one another, 1, 2, or 3;

at least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic fused polycyclic group, the substituted divalent non-aromatic fused heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic fused polycyclic group, and the substituted monovalent nonaromatic fused heteropolycyclic group is:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, $—Si(Q_{11})(Q_{12})(Q_{13})$, $—N(Q_{11})(Q_{12})$, $—B(Q_{11})(Q_{12})$, $—C(=O)(Q_{11})$, $—S(=O)_2(Q_{11})$, and $—P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, and a monovalent non-aromatic fused heteropolycyclic group, each optionally substituted, independently from one another, with at least one of deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_6$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, $—Si(Q_{21})(Q_{22})(Q_{23})$, $—N(Q_{21})(Q_{22})$, $—B(Q_{21})(Q_{22})$, $—C(=O)(Q_{21})$, $—S(=O)_2(Q_{21})$, and $—P(=O)(Q_{21})(Q_{22})$; and $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$;

wherein $Q_1$ to $Q_3$, $Q_{11}$ to $Q_{13}$, $Q_{21}$ to $Q_{23}$, and $Q_{31}$ to $Q_{33}$ are each, independently from one another, hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic fused polycyclic group, a monovalent non-aromatic fused heteropolycyclic group, a biphenyl group, or a terphenyl group.

7. The organic light-emitting device of claim 1, wherein the first hosts included in the first emission layer, the second emission layer, and the at least one auxiliary layer are each, independently from one another, a compound of Compounds 1-1 to 1-10 and 1-19 to 1-22;

the second hosts included in the first emission layer, the second emission layer, and the at least one auxiliary layer are each, independently from one another, a compound of Compounds 2-1 to 2-30:

the phosphorescent organometallic compound of the first dopant, the second dopant, or both the first dopant and the second dopant is a compound of Compounds 3-11 to 3-18; and the TADF compound of the first dopant, the second dopant, or both the first dopant and the second dopant is one of Compounds 4-1 to 4-13:

1-1

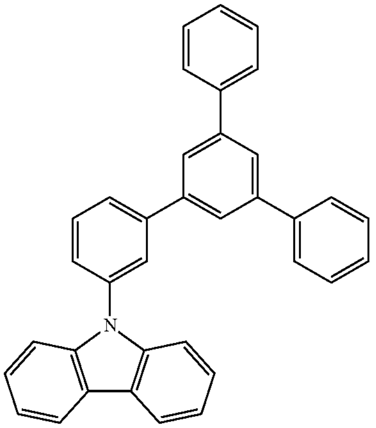

1-2

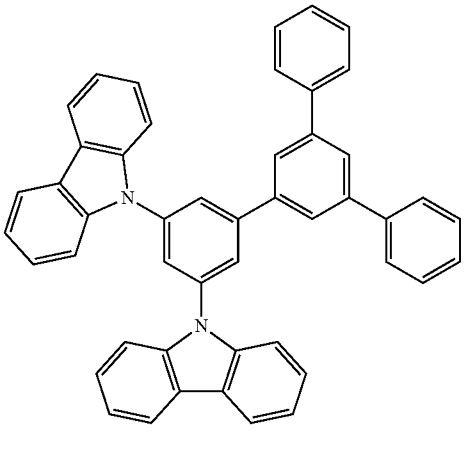

-continued
1-3
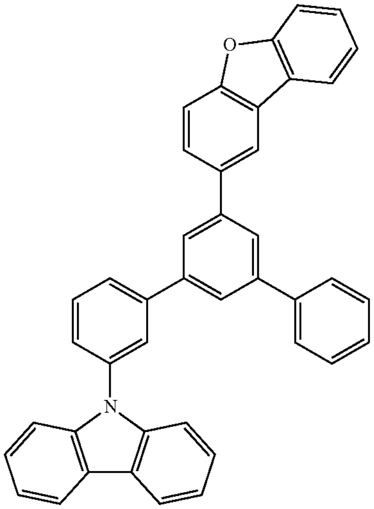
1-4
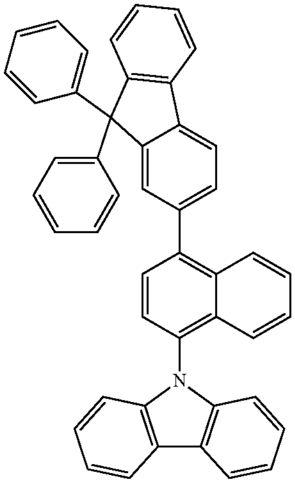
1-5
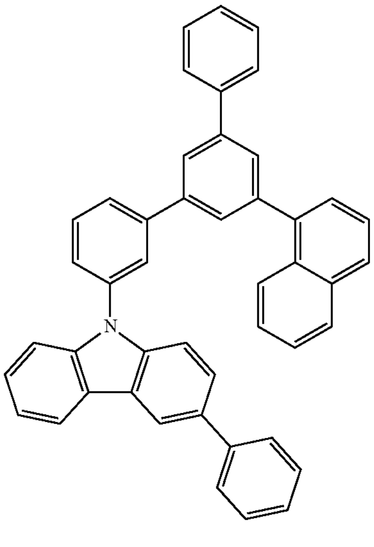
-continued
1-6
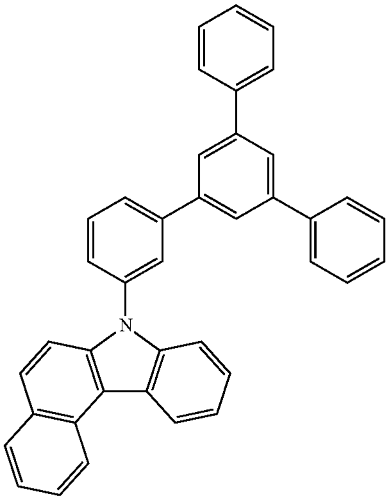
1-7
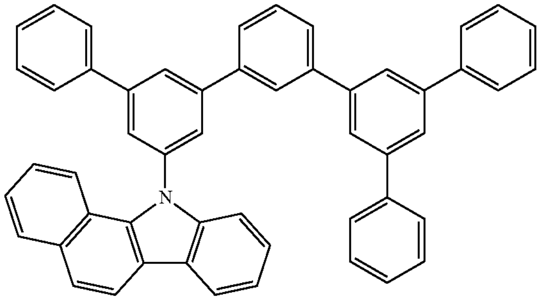
1-8
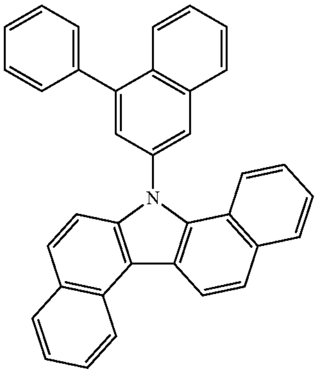
1-9
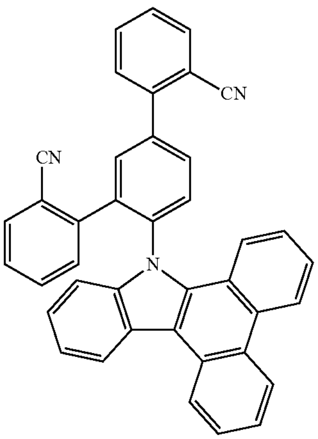

-continued
1-10
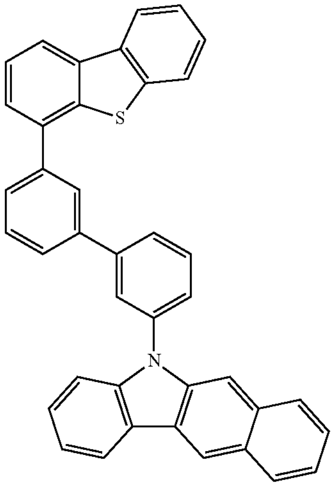
1-11
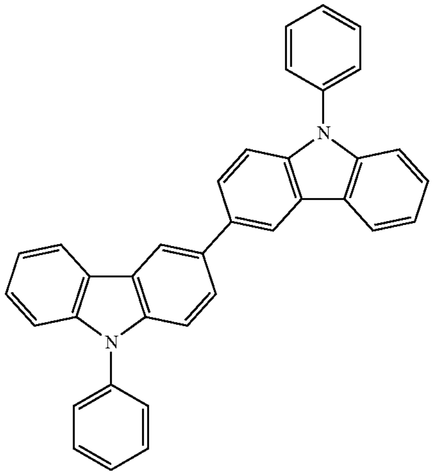
1-12
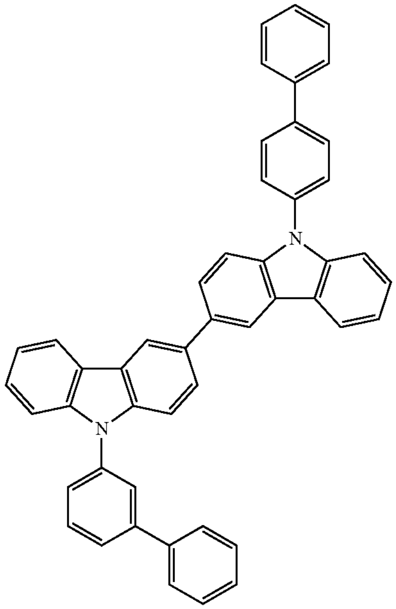
-continued
1-13
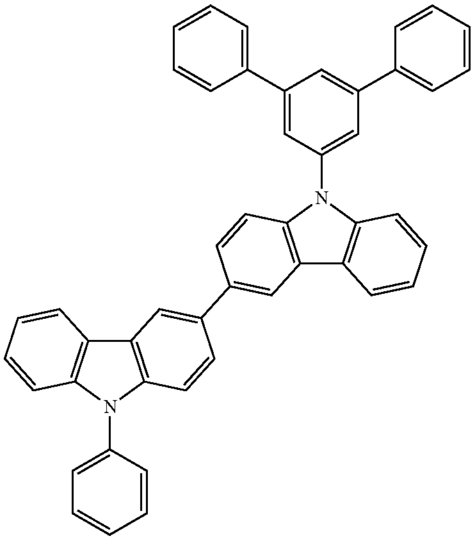
1-14
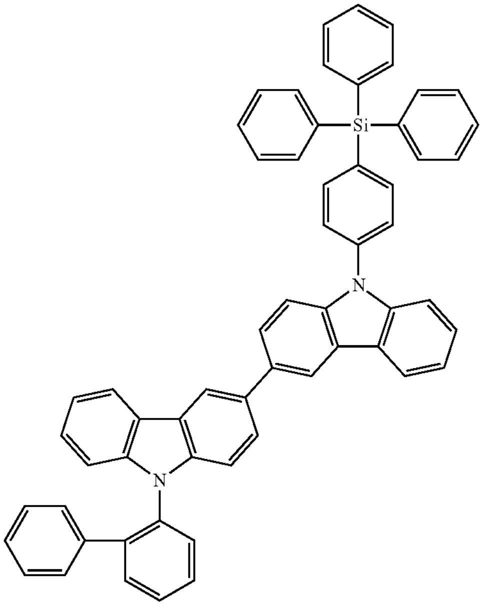

-continued
1-15
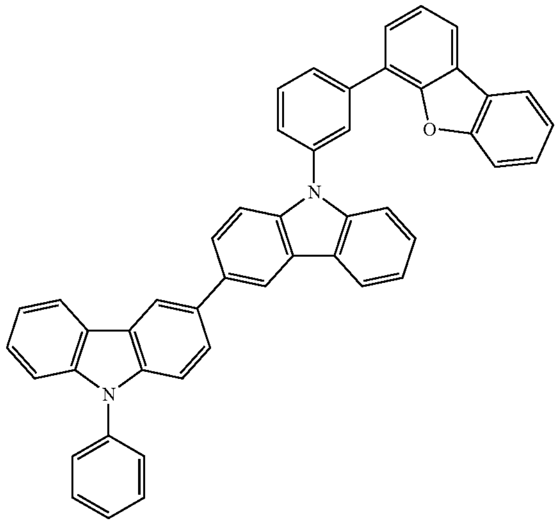
1-16
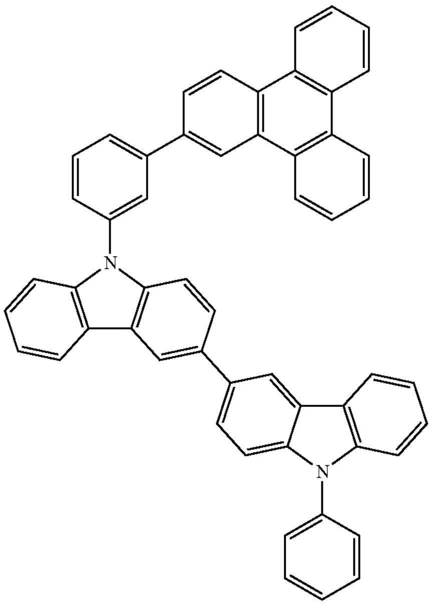
1-17
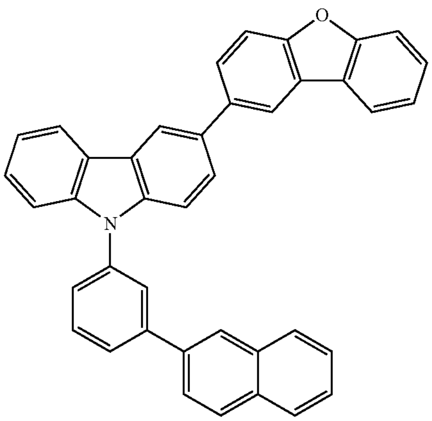
-continued
1-18
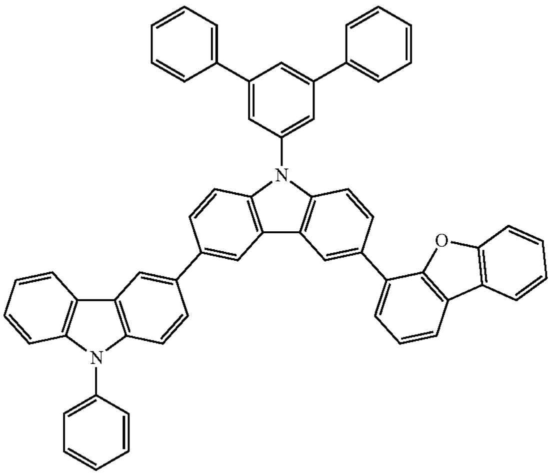
1-19
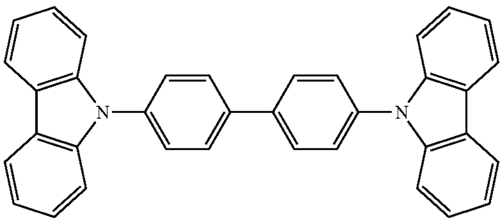
1-20
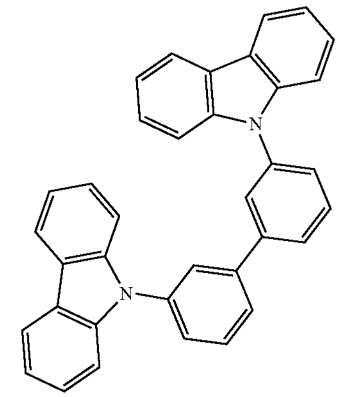
1-21
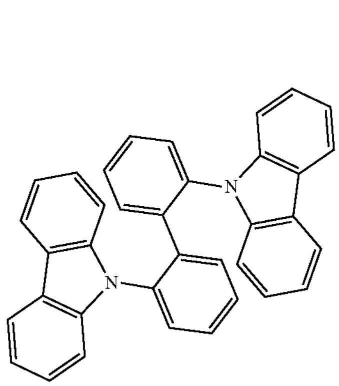

-continued
1-22
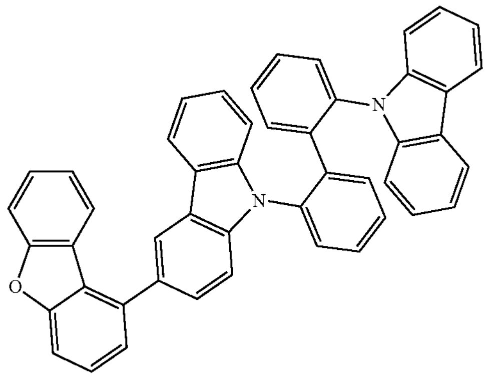
2-1
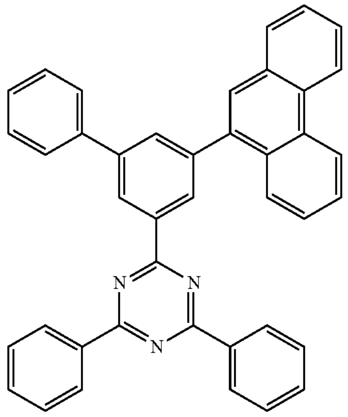
2-2
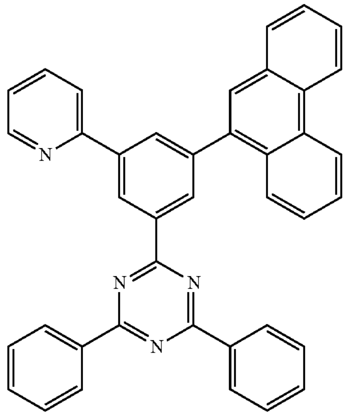
2-3
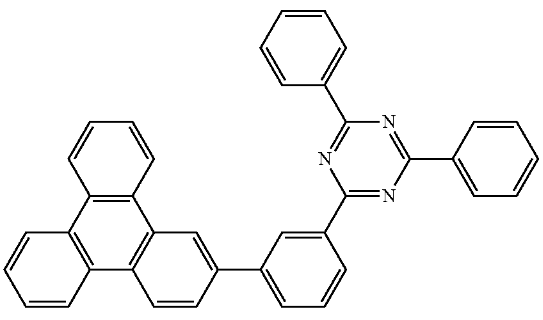
-continued
2-4
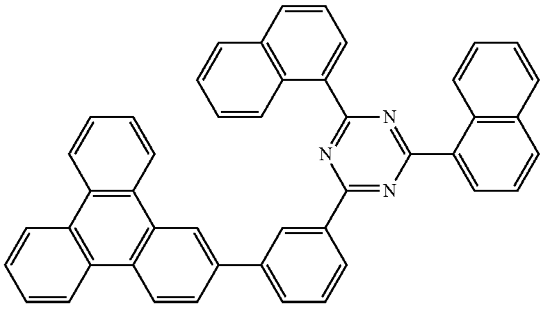
2-5
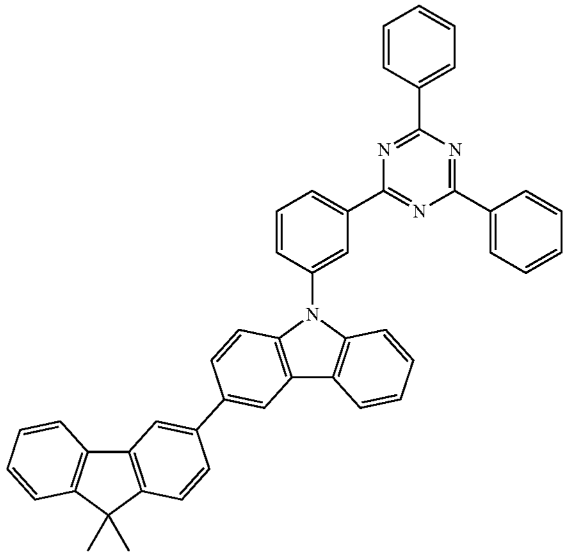
2-6
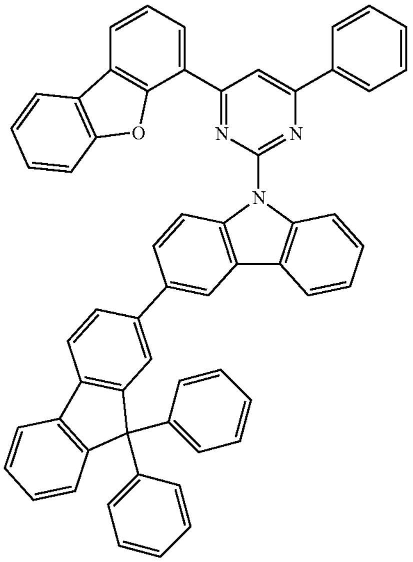

-continued
2-7
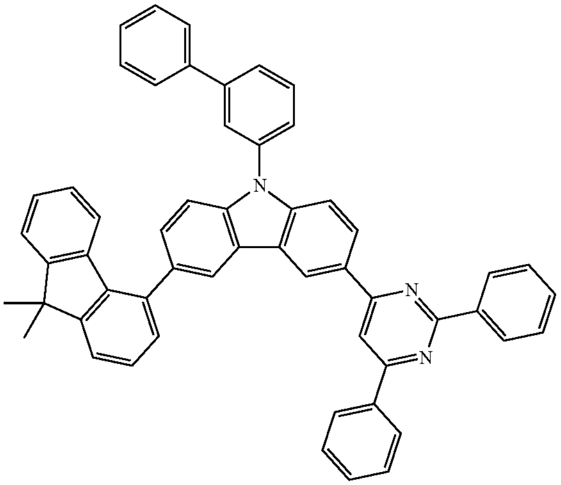
2-8
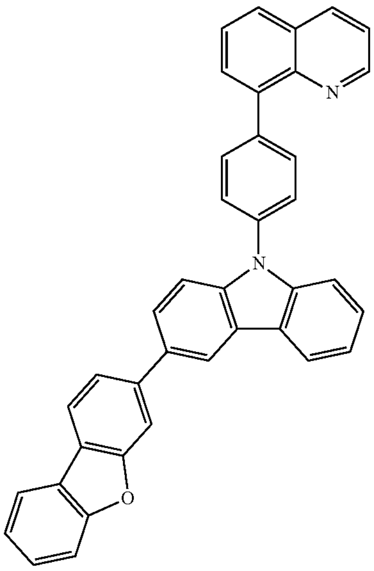
2-9
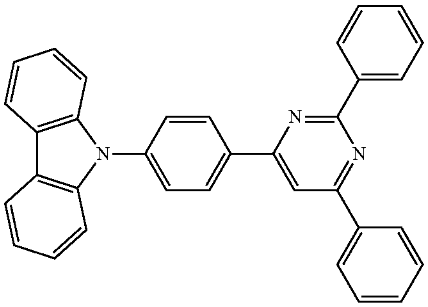
-continued
2-10
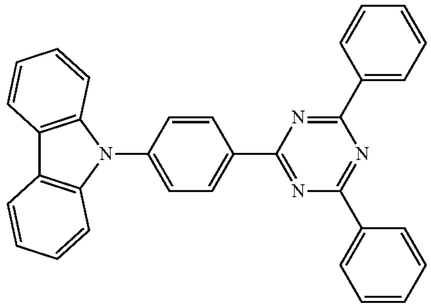
2-11
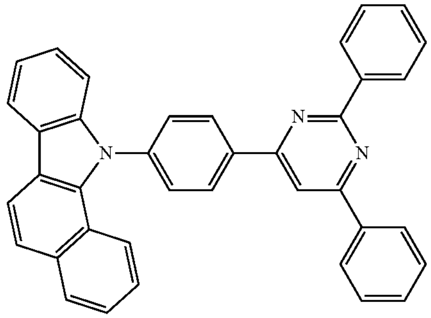
2-12
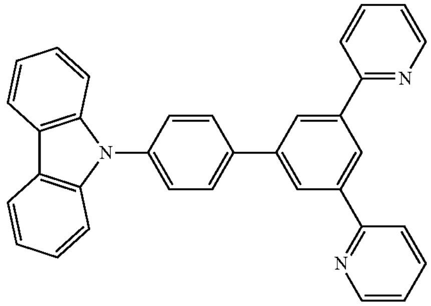
2-13
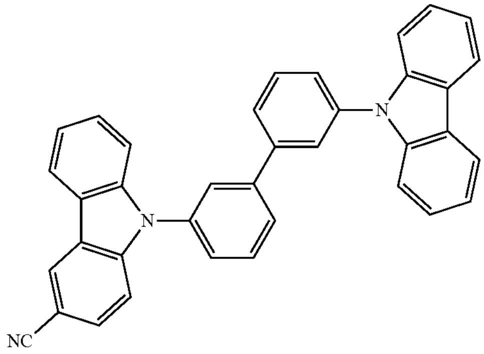

-continued
2-14
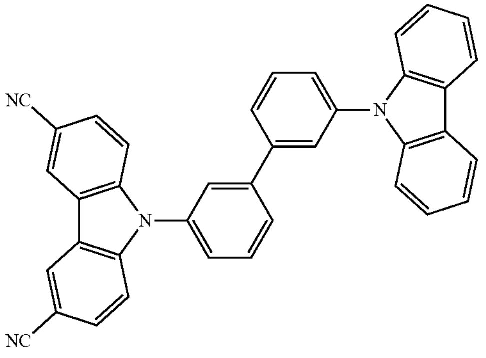
2-15
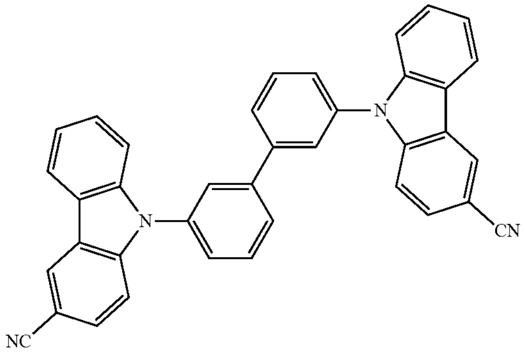
2-16
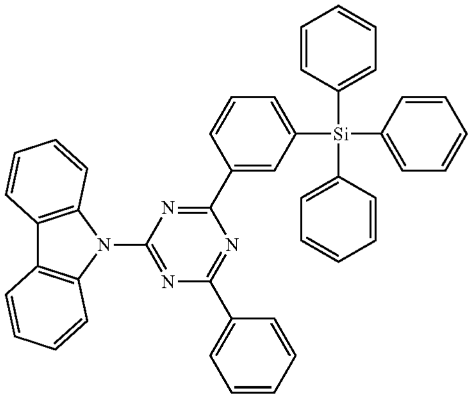
-continued
2-17
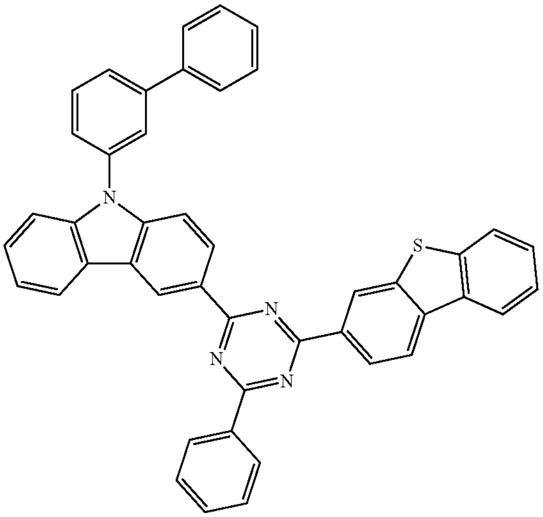
2-18
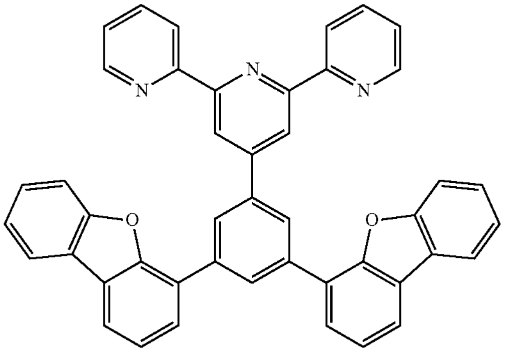
2-19
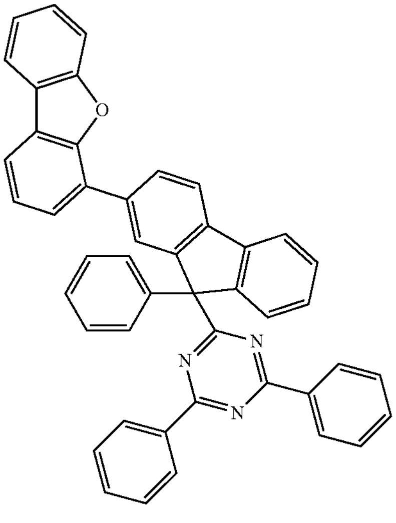

-continued
2-20
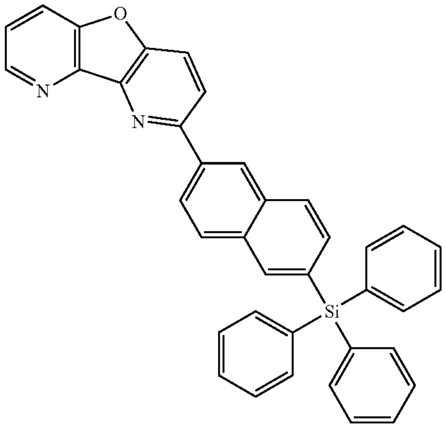
2-21
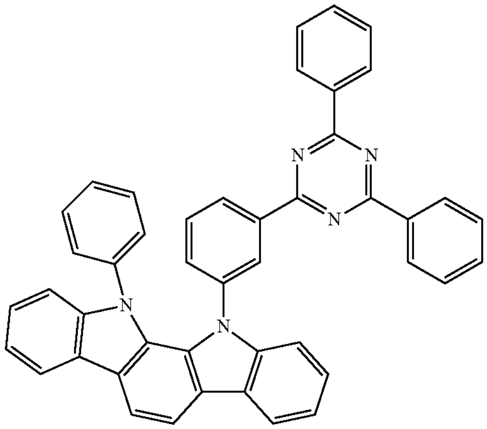
2-22
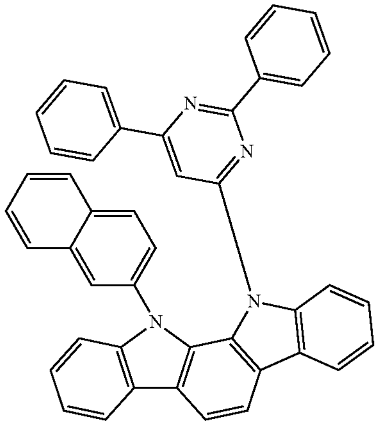
-continued
2-23
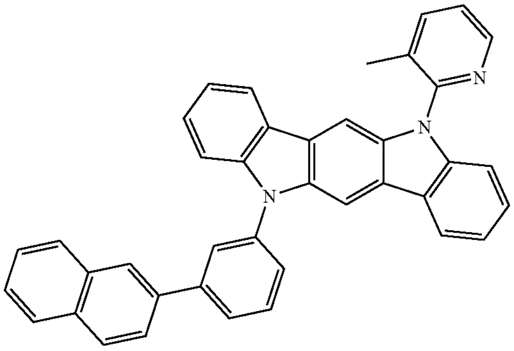
2-24
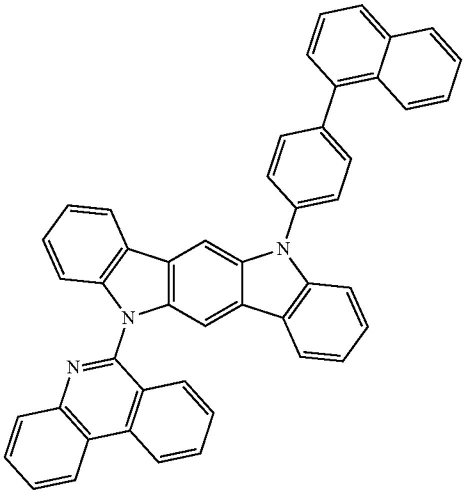
2-25
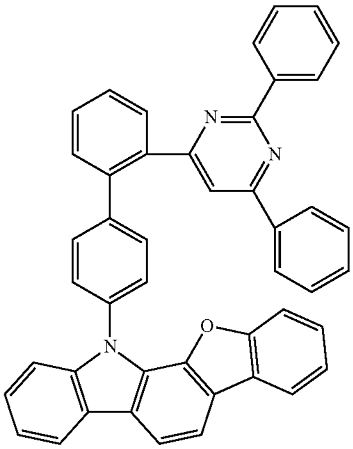

-continued
2-26
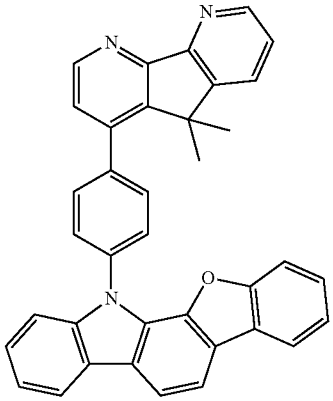
2-27
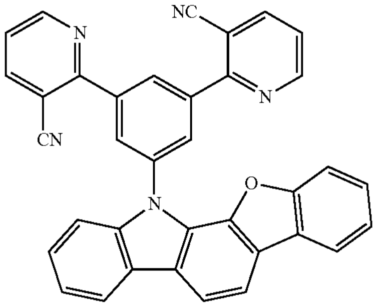
2-28
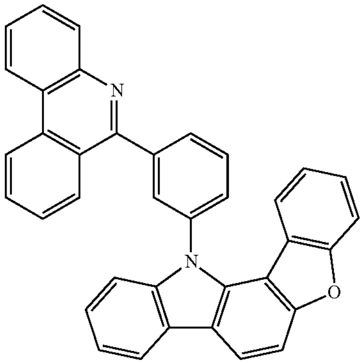
2-29
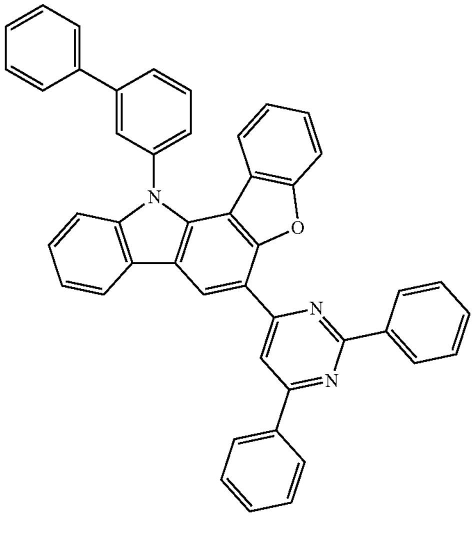
-continued
2-30
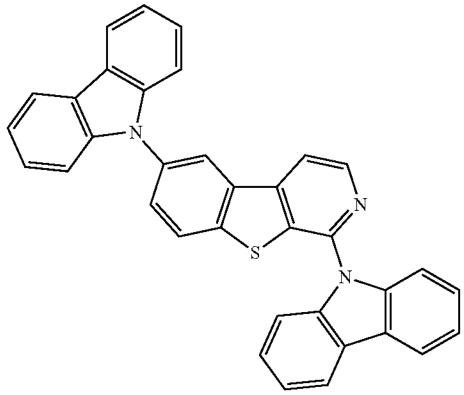
3-11
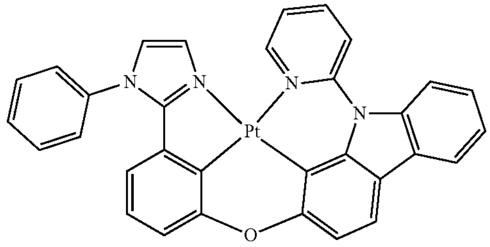
3-12
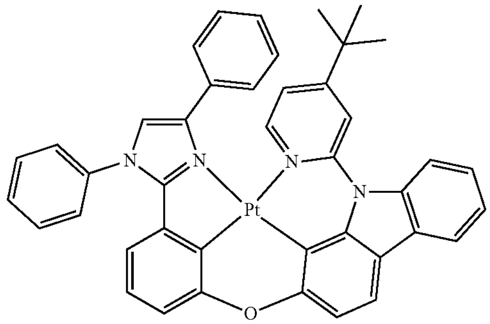
3-13
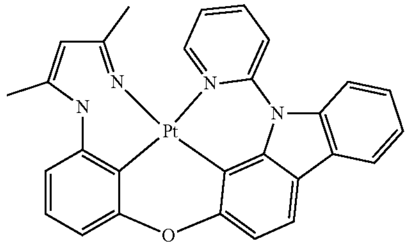
3-14
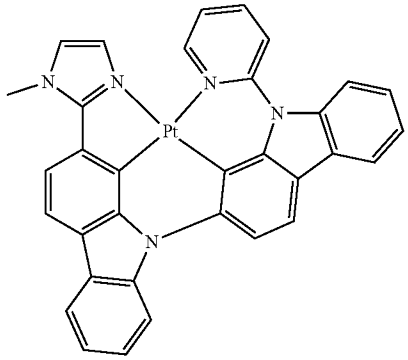

-continued
3-15
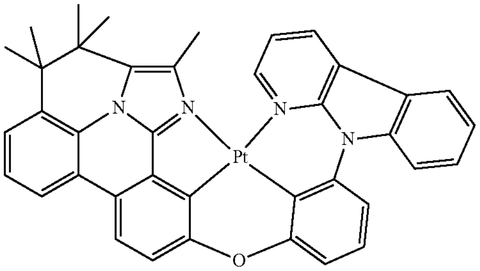
3-16
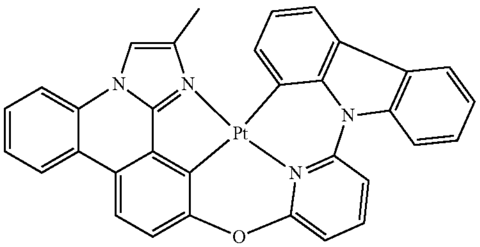
3-17
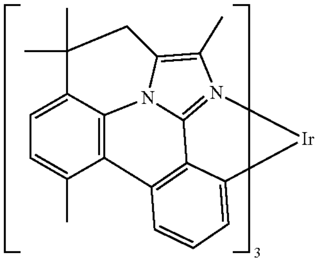
3-18
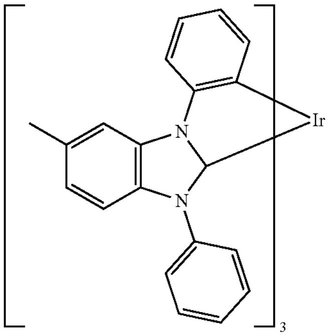
4-1
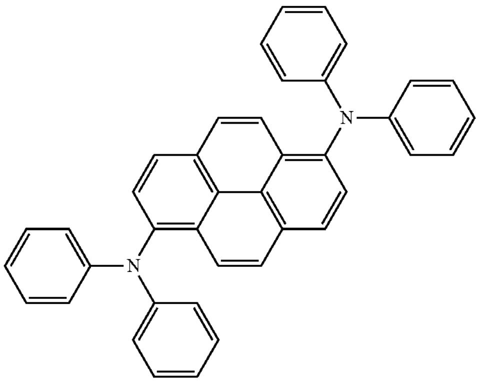
-continued
4-2
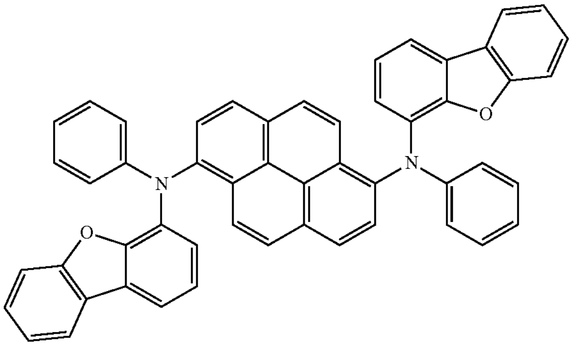
4-3
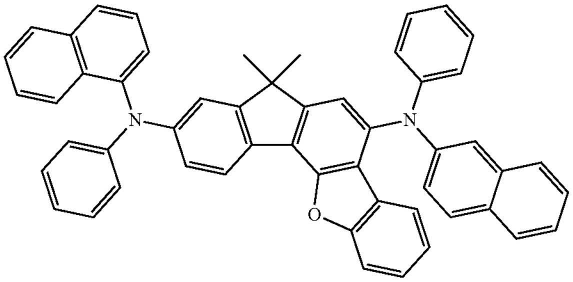
4-4
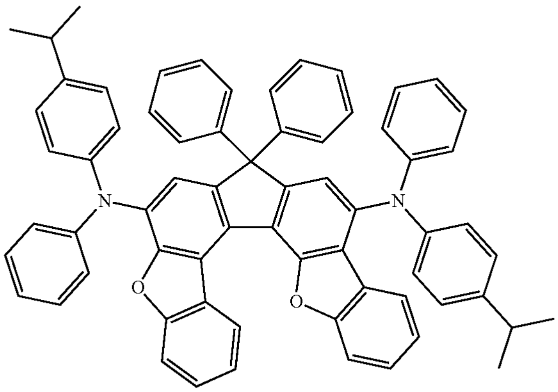
4-5
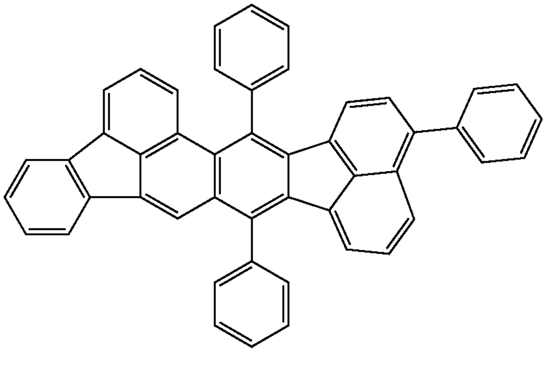

-continued
4-6
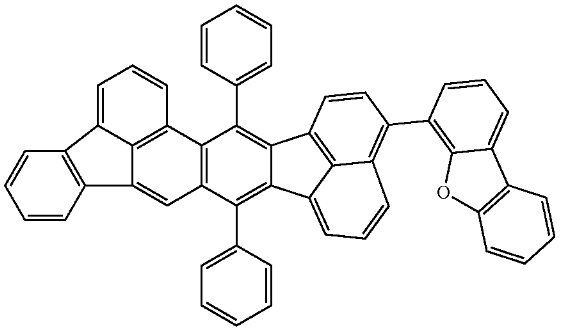
4-7
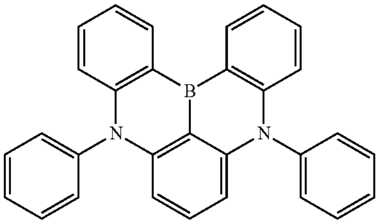
4-8
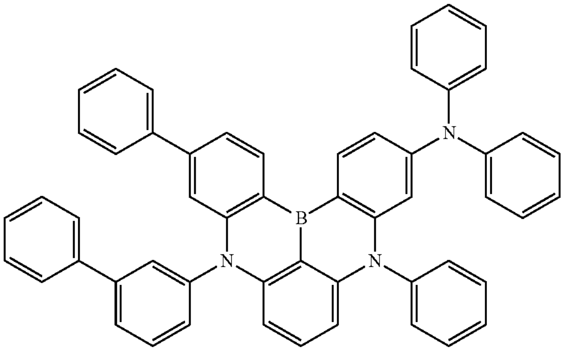
4-9
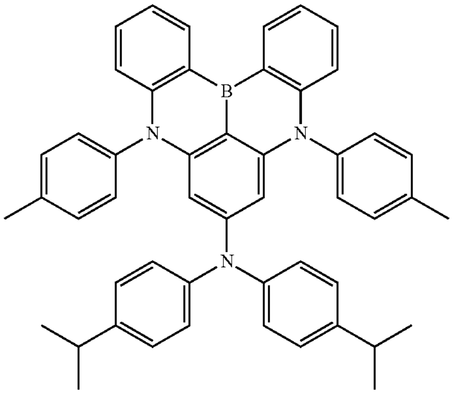
-continued
4-10
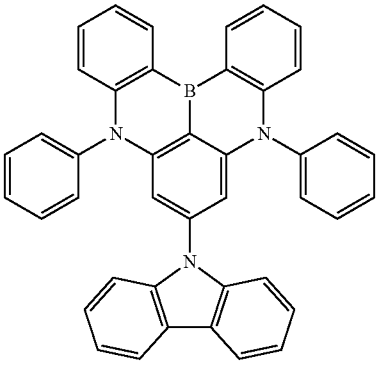
4-11
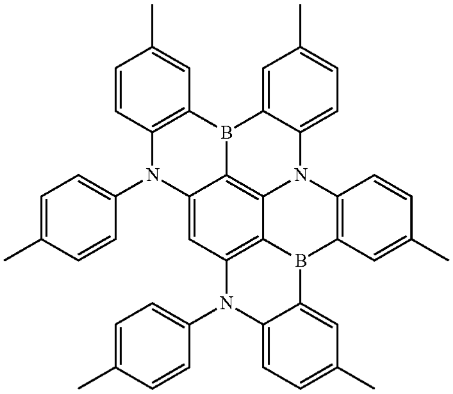
4-12
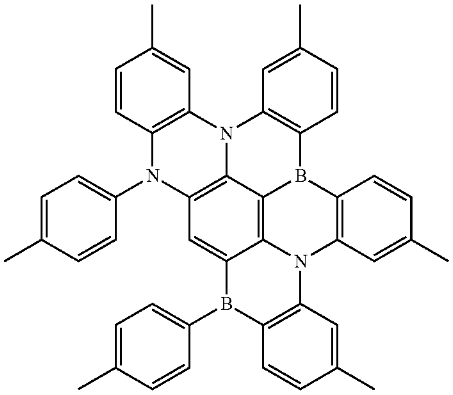

-continued 4-13

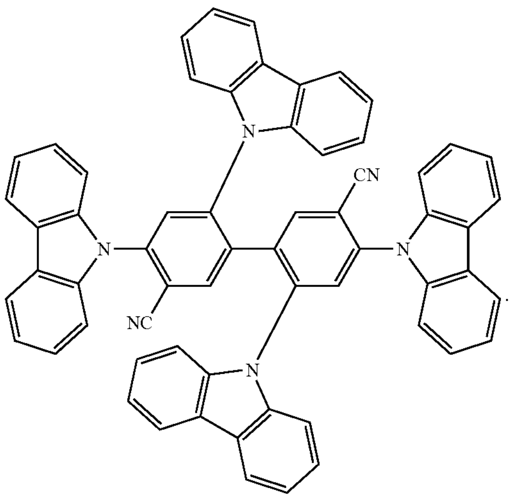

8. The organic light-emitting device of claim 1, wherein the at least one auxiliary layer comprises a first auxiliary layer disposed between the first electrode and the first emission layer and directly contacting the first emission layer;

the first auxiliary layer comprises a first host; and a first host included in the first auxiliary layer and a first host included in the first emission layer are identical to or different from each other.

9. The organic light-emitting device of claim 8, wherein the first auxiliary layer consists of the first host.

10. The organic light-emitting device of claim 1, wherein the second auxiliary layer consists of the second host.

11. The organic light-emitting device of claim 1, wherein the first dopant and the second dopant are each, independently from one another, a phosphorescent organometallic compound.

12. The organic light-emitting device of claim 1, wherein the first dopant has a first maximum emission wavelength and the second dopant has a second maximum emission wavelength different from the first maximum emission wavelength.

13. The organic light-emitting device of claim 1, wherein the first emission layer satisfies Equations 2 and 3:

$$|HOMO(D1)-HOMO(EML1(H1))| \leq \text{about } 0.3 \text{ eV}$$ <Equation 2>

$$|HOMO(D1)-HOMO(EML1(H2))| \leq \text{about } 0.3 \text{ eV}$$ <Equation 3> wherein, in Equations 2 and 3,

HOMO(D1) is a highest occupied molecular orbital (HOMO) energy level (eV) of the first dopant, HOMO (EML1 (H1)) is a HOMO energy level (eV) of a first host included in the first emission layer, and HOMO (EML1 (H2)) is a HOMO energy level (eV) of a second host included in the first emission layer.

14. The organic light-emitting device of claim 1, wherein the second emission layer satisfies Equations 4 and 5:

$$|LUMO(D2)-LUMO(EML2(H1))| \leq \text{about } 0.3 \text{ eV}$$ <Equation 4>

$$|LUMO(D2)-LUMO(EML2(H2))| \leq \text{about } 0.3 \text{ eV}$$ <Equation 5> wherein, in Equations 4 and 5,

LUMO(D2) is a lowest unoccupied molecular orbital (LUMO) energy level (eV) of the second dopant, LUMO(EML2 (H1)) is a LUMO energy level (eV) of a first host included in the second emission layer, and LUMO(EML2 (H2)) is a LUMO energy level (eV) of a second host included in the second emission layer.

15. An apparatus comprising a thin-film transistor comprising a source electrode, a drain electrode, and an activation layer; and the organic light-emitting device of claim 1, wherein the first electrode of the organic light-emitting device is electrically connected to one of the source electrode and the drain electrode of the thin-film transistor.

* * * * *